US006455681B1

(12) United States Patent
Dean et al.

(10) Patent No.: US 6,455,681 B1
(45) Date of Patent: Sep. 24, 2002

(54) DNA MOLECULES ENCODING SINGLE STRAND GAP RESPONSE PROTEINS INVOLVED IN ACTIVATION OF A DNA REPAIR/CELL CYCLE CHECKPOINT PATHWAY

(75) Inventors: Frank Dean, New York; Michael E. O'Donnell, Hastings-on-Hudson, both of NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/292,858

(22) Filed: Apr. 16, 1999

Related U.S. Application Data

(60) Provisional application No. 60/082,020, filed on Apr. 16, 1998.

(51) Int. Cl.$^7$ .................. C07H 71/04; C12D 21/02; C07K 14/00

(52) U.S. Cl. ............ 536/23.1; 435/71.1; 435/69.1; 435/471; 435/455; 435/320.1; 435/252.3; 435/325; 530/350; 514/44; 424/93.1

(58) Field of Search .................. 530/350; 435/325, 435/252.3, 320.1, 455, 471, 69.1, 71.1; 536/23.1; 514/44; 424/93.1

(56) References Cited

U.S. PATENT DOCUMENTS

| | | | |
|---|---|---|---|
| 5,688,641 A | | 11/1997 | Sager et al. |
| 5,843,737 A | * | 12/1998 | Chen et al. |
| 5,965,427 A | | 10/1999 | Dolganov et al. |

OTHER PUBLICATIONS

<http://www.ncbi.nlm.nih.gov:80/entrez> Accession No. AF058932; accessed May 15, 2000, Apr. 1998.*
<http://www.ncbi.nlm.nih.gov:80/entrez> Accession No. AJ004974; accessed May 5, 2000, Mar. 1998.*
<http://www.ncbi.nlm.nih.gov:80/entrez> Accession No. AF030933; accessed May 5, 2000, Oct. 1997.*
<http://www.ncbi.nlm.nih.gov:80/entrez> Accession No. AJ004977; accessed May 5, 2000, Mar. 1998.*
<http://www.ncbi.nlm.nih.gov:80/entrez> Accession No. Y16893; accessed May 5, 2000, Mar. 1998.*
<http://www.ncbi.nlm.nih.gov:80/entrez> Accession No. AJ004976; accessed May 5, 2000, Mar. 1998.*
<http://www.ncbi.nlm.nih.gov:80/entrez> Accession No. Y16894; accessed May 5, 2000, Mar. 1998.*
<http://www.ncbi.nlm.nih.gov:80/entrez> Accession No. AF05894; accessed May 5, 2000, Apr. 1998.*
Kostrub et al., EMBO J. 17: 2055–2066, Hus1p, a conserved fission yeast checkpoint protein, interacts with Rad1p and is phosphorylated in response to DNA damage, Apr. 1998.*
Verma et al., Nature 389: 239–242, Gene therapy—promises, problems and prospects, Sep. 1997.*

Anderson et al., Nature 392: 25–30, Human gene therapy, Apr. 1998.*
The New York Times, vol. CXLIX, No. 51, 372, "Scientists report the first success of gene therapy" A1, cont. A16, Apr. 1998.*
Lydall et al., "From DNA damage to Cell Cycle Arrest and Suicide: A Budding Yeast Perspective," *Curr. Opin. in Genet. & Dev.* 6:4–11 (1996).
Savitsky et al., "A Single Ataxia Telangiectasia Gene with a Product Similar to PI–3 Kinase," *Science* 268:1749–1753 (1995).
Hartwell et al., "Cell Cycle Control and Cancer," *Science* 266:1821–1828 (1994).
Hartwell, L., "Defects in a Cell Cycle Checkpoint May Be Responsible for the Genomic Instability of Cancer Cells," *Cell* 71:543–546 (1992).
Hartwell et al., "Checkpoints: Controls that Ensure the Order of Cell Cycle Events," *Science* 246:629–634 (1989).
Donehower et al., "Mice Deficient for p53 are Developmentally Normal but Susceptible to Spontaneous Tumours," *Nature* 356:215–221 (1992).
Hann et al., "The Dominating Effect of Mutant p53," *Nature Genetics* 9:221–222 (1995).
Hupp et al., "Small Peptides Activate the Latent Sequence–Specific DNA Binding Function of p53," *Cell* 83:237–245 (1995).
Mackett et al., "Vaccinia Virus: A Selectable Eukaryotic Cloning and Expression Vector," *Proc. Natl. Acad. Sci. USA* 79:7415–7419 (1982).
Askew et al., "Site–Directed Point Mutations in Embryonic Stem Cells: A Gene–Targeting Tag–and–Exchange Strategy," *Mol. Cell. Biol.* 13(7):4115–4124 (1993).
Jonveaux et al., "Deletion of (7p13p14) in Non–Hodgkin's Lymphoma," *Cancer Genet Cytogenet* 50:53–56 (1990).
Uckun et al., "Heterogeneity of Cultured Leukemic Lymphoid Progenitor Cells from B Cell Precursor Acute Lymphoblastic Leukemia (ALL) Patients," *J. Clin. Invest.* 80:639–646 (1987).
Uckun et al., "Immunophenotype–Karyotype Associations in Human Acute Lymphoblastic Leukemia," *Blood* 73(1):271–280 (1989).

(List continued on next page.)

*Primary Examiner*—James Ketter
*Assistant Examiner*—Daniel Sullivan
(74) *Attorney, Agent, or Firm*—Nixon Peabody LLP

(57) ABSTRACT

The present invention relates to isolated DNA molecules encoding mammalian single strand gap response proteins involved in activation of a DNA repair/cell cycle checkpoint pathway. Expression systems and host cells containing those DNA molecules as well as the proteins themselves and antibodies raised against them are also disclosed. The DNA molecules, proteins, and antibodies can be used for diagnostic purposes, while the DNA molecules also have therapeutic utility. In addition, transgenic animals can be produced where the gene encoding a single strand gap response protein is disrupted or deleted. As a result, these animals are characterized by spontaneous tumor development.

23 Claims, 15 Drawing Sheets 4

OTHER PUBLICATIONS

Conley et al., "A Chromosomal Breakage Syndnrome With Profound Immunodeficiency," *Blood* 67(5):1251–1255 (1986).

Hecht et al., "Chromosome Changes Connect Immunodeficiency and Cancer in Ataxia–Telangiectasia," *Am J Pediatr Hematol Oncol* 9(2):185–188 (1987).

Taalman et al., "Further Delineation of the Nijmegen Breakage Syndrome," *American Journal of Medical Genetics* 32:425–431 (1989).

Barbi et al., "Chromosome Instability and X–Ray Hypersensitivity in a Microencephalic and Growth–Retarded Child," *American Journal of Medical Genetics* 40:44–50 (1991).

Green et al., "Severe Microencephaly with Normal Intellectual Development: The Nijmegen Breakage Syndrome," *Arch Dis Child* 73:431–434 (1995).

Renedo et al., "Cytogenetic and Molecular Studies of Siblings with Ataxia Telangiectasia Followed for 7 Years," *Cancer Genet Cytogenet* 95:178–181 (1997).

Dewald et al., "T–Lymphocytes with 7;14 Translocations: Frequency of Occurrence, Breakpoints, and Clinical and Biological Significance," *Am J Hum Genet* 38:520–532 (1986).

Hecht et al., "Fragile Sites Limited to Lymphocytes: Molecular Recombination and Malignancy," *Cancer Genet Cytogenet* 26:95–104 (1987).

Lindsay et al., "S–phase–specific Activation of Cds1 Kinase Defines a Subpathway of the Checkpoint Response in *Schizosaccharomyces pombe*," *Genes & Development* 12:382–395 (1998).

Nugent et al., "Cdc13p: A Single–Strand Telomeric DNA–Binding Protein with a Dual Role in Yeast Telomere Maintenance," *Science* 274:249–251 (1996).

Walworth et al., "rad–Dependent Response of the chk1–Encoded Protein Kinase at the DNA Damage Checkpoint," *Science* 271:353–356 (1996).

Lin et al., "The Saccharomyces CDC13 Protein is a Single–Strand $TG_{1-3}$ Telomeric DNA–Binding Protein In Vitro That Affects Telomere Behavior In Vivo," *Proc. Natl. Acad. Sci. USA* 93:13760–13765 (1996).

Garvik et al., "Single–Stranded DNA Arising at Telomeres in cdc13 Mutants May Constitute a Specific Signal for the RAD9 Checkpoint," *Mol. Cell. Biol.* 15(11):6128–6137 (1995).

Harvey et al., "A Mutant p53 Transgene Accelerates Tumour Development in Heterozygous but not Nullizygous P53–Deficient Mice," *Nature Genetics* 9:305–311 (1995).

Al–Khodairy et al., "DNA Repair Mutants Defining $G_2$ Checkpoint Pathways in *Schizosaccharomyces pombe*," *The EMBO Journal* 11(4):1343–1350 (1992).

Al–Khodairy et al., "Identification and Characterization of New Elements Involved in Checkpoint and Feedback Controls In Fission Yeast," *Molecular Biology of the Cell* 5:147–160 (1994).

Carr, A.M., "Control of Cell Cycle Arrest by the $Mec1^{sc}/Rad3^{sp}$ DNA Structure Checkpoint Pathway," *Current Opinions in Genetics & Development* 7:93–98 (1997).

Collins et al., "The Cell Cycle and Cancer," *Proc. Natl. Acad. Sci. USA* 94:2776–2778 (1997).

Enoch et al., "Mutation of Fission Yeast Cell Cycle Control Genes Abolishes Dependence of Mitosis on DNA Replication," *Cell* 60:665–673 (1990).

Enoch et al., "Fission Yeast Genes Involved in Coupling Mitosis to Completion of DNA Replication," *Genes & Development* 6:2035–2046 (1992).

Enoch et al., "Cellular Responses to DNA Damage: Cell–Cycle Checkpoints, Apoptosis and the Roles of p53 and ATM," *Trends Biochem. Sci.* 20:426–430 (1995).

Griffiths et al., "Fission Yeast rad17: A Homologue of Budding Yeast RAD24 that Shares Regions of Sequence Similarity with DNA Polymerase Accessory Proteins," *The EMBO Journal* 14(23):5812–5823 (1995).

Holliday et al., "Genetic Characterization of rec–1, a Mutant of *Ustilago maydis* Defective in Repair and Recombination," *Genet. Res., Camb.* 27:413–453 (1976).

Jimenez et al., "The $rad3^+$ Gene of *Schizosaccharomyces pombe* is Involved in Multiple Checkpoint Functions and in DNA Repair," *Proc. Natl. Acad. Sci. USA* 89:4952–4956 (1992).

Kastan et al., "Participation of p53 Protein in the Cellular Response to DNA Damage," *Cancer Research* 51:6304–6311 (1991).

Kostrub et al., "Molecular Analysis of $hus1^+$, a Fission Yeast Gene Required for S–M and DNA Damage Checkpoints," *Mol Gen Genet* 254:389–399 (1997).

Kuerbitz et al., "Wild–type p53 is a Cell Cycle Checkpoint Determinant Following Irradiation," *Proc. Natl. Acad. Sci. USA* 89:7491–7495 (1992).

Lehmann et al., "The Ataxia–telangiectasia Gene: A Link Between Checkpoint Controls, Neurodegeneration and Cancer," *Trends Genet.* 11(10):375–377 (1995).

Long et al., "The *Schizosaccharomyces pombe* rad1 Gene Consists of Three Exons and the cDNA Sequence is Partially Homologous to the *Ustilago maydis* REC1 cDNA," *Gene* 148:155–159 (1994).

Lydall et al., "Yeast Checkpoint Genes in DNA Damage Processing: Implications for Repair and Arrest," *Science* 270:1488–1491 (1995).

McFarlane et al., "Characterisation of the *Schizosaccharomyces pombe* rad4/cut5 Mutant Phenotypes: Dissection of DNA Replication and G2 Checkpoint Control Function," *Mol Gen Genet* 255:332–340 (1997).

Nasim et al., "Genetic Control of Radiation Sensitivity in *Schizosaccharomyces pombe*," *Genetics* 79:573–581 (1975).

Onel et al., "Mutation Avoidance and DNA Repair Proficiency in *Ustilago maydis* are Differentially Lost with Progressive Truncation of the REC1 Gene Product," *Mol. Cell. Biol.* 15(10):5329–5338 (1995).

Onel et al., "The REC1 Gene of *Ustilago maydis*, Which Encodes a 3'→5' Exonuclease, Couples DNA Repair and Completion of DNA Synthesis to a Mytotic Checkpoint," *Genetics* 143:165–174 (1996).

Rowley et al., "Checkpoint Controls in *Schizosaccharomyces pombe*: rad 1," *The EMBO Journal* 11(4):1335–1342 (1992).

Russell et al., "Schizosaccharomyces pombe and *Saccharomyces cerevisiae*: A Look at Yeasts Divided," *Cell* 45:781–782 (1986).

Sheldrick et al., "Feedback Controls and G2 Checkpoints: Fission Yeast as a Model System," *BioEssays* 15(12):775–781 (1993).

Siede et al., "Cloning and Characterization of RAD17, a Gene Controlling Cell Cycle Responses to DNA Damage in *Saccharomyces cerevisiae*", *Nucleic Acids Research* 24(8):1669–1675 (1996).

Stewart et al., "S–phase and DNA–damage Checkpoints: A Tale of Two Yeasts," *Current Opinion in Cell Biology* 8:781–787 (1996).

Sunnerhagen et al., "Cloning and Analysis of a Gene Involved in DNA Repair and Recombination, the rad1 Gene of *Schizosaccharomyces pombe*," *Mol. Cell. Biol.* 10(7):3750–3759 (1990).

Thelen et al., "The REC1 Gene of *Ustilago maydis* Involved in the Cellular Response to DNA Damage Encodes An Exonuclease," *J. Biol. Chem.* 269(1):747–754 (1994).

Tsukuda et al., "Isolation of the REC1 Gene Controlling Recombination in *Ustilago maydis*," *Gene* 85:335–341 (1980).

Weinert et al., "Mitotic Checkpoint Genes in Budding Yeast and the Dependence of Mitosis on DNA Replication and Repair," *Genes & Development* 8:652–665 (1994).

*Escherichia coli* and Expression Vectors Containing a Protein Kinase Recognition Motif, $His_6$–tag and Hemagglutinin Epitope, *Gene* 166:177–178 (1995).

Capecchi, M.R., "Altering the Genome by Homologous Recombination," *Science* 244:1288–1292 (1989).

Mansour et al., "Disruption of the Proto–oncogene int–2 in Mouse Embryo–derived Stem Cells: A General Strategy for Targeting Mutations in Non–selectable Genes," *Nature* 336:348–352 (1988).

Pejovic, "Genetic Changes in Ovarian Cancer," *Ann Med* 27:73–78 (1995).

Wieland et al., "Allelic Deletion Mapping on Chromosome 5 in Human Lung Carcinomas," *Oncogene* pp. 97–102 (1996).

Weinert et al., "Characterization of RAD9 of *Saccharomyces cerevisiae* and Evidence that Its Function Acts Posttranslationally in Cell Cycle Arrest after DNA Damage," *Molecular and Cellular Biology* 10(12):6554–6564 (1990).

Keppen et al., "Clinical Phenotype and Molecular Analysis of a Three–Generation Family With an Interstitial Deletion Of the Short Arm of Chromosome 5," *American Journal of Medical Genetics* 44:356–360 (1992).

Miura et al., "Chromosome Alterations in Human Small Cell Lung Cancer: Frequent Involvment of 5q," *Cancer Research* 52:1322–1328 (1992).

Fairman et al., "Translocations and Deletions of 5q13.1 in Myelodysplasia and Acute Myelogenous Leukemia: Evidence for a Novel Critical Locus," *Blood* 88(6):2259–2266 (1996).

Shanske et al., "A Myeloproliferative Disorder with Eosinophilia Associated with a Unique Translocation (3:5)," *British Journal of Haematology* 95:524–526 (1996).

Örndal et al., "Chromosome Aberrations and Cytogenetic Intratumor Heterogeneity in Chondrosarcomas," *Cancer Res Clin Oncol* 120:51–56 (1993).

Travassoli et al., "Loss of Heterozygosity on Chromosome 5q in Ovarian Cancer is Frequently Accompanied by TP53 Mutation and Identifies a Tumour Suppressor Gene Locus at 5q13.1–21" *British Journal of Cancer* 74:115–119 (1996).

Böhm et al., "Deletion Analysis at the DEL–27, APC and MTS1 LOCI in Bladder Cancer: LOH at the DEL–27 Locus on 5p13–12 is a Prognostic Marker of Tumor Progression," *Int. J. Cancer* 74:291–295 (1997).

Bentley et al., "The *Schizosaccharomyces pombe* rad3 Checkpoint Gene," *The EMBO Journal* 15(23):6641–6651 (1996).

Tarkkanen et al., "Cytogenetic Study of 249 Consecutive Patients Examined for a Bone Tumor," *Cancer Genet Cytogenet* 68:1–21 (1993).

Goguel et al., "Evolution of Chromosomal Alterations and Biologic Features in Two Small Cell Lung Carcinoma Cell Lines Established from One Patient During the Course of the Disease," *Cancer Genet Cytogenet* 80:47–54 (1995).

Gogineni et al, "A New Translocation, t(5;21)(q13;q22) in Acute Myelogenous Leukemia," *Cancer Genet Cytogenet* 88:167–169 (1996).

Jackson, "The Recognition of DNA Damage," *Current Opinion in Genetics & Development* 6:19–25 (1996).

Holden et al., "Nucleotide Sequence of the REC1 Gene of *Ustilago maydis*," *Nucleic Acids Research* 17(24):10489 (1989).

Yeatman et al., "Identification of Genetic Alterations Associated with the Process of Human Experimental Colon Cancer Liver Metastasis in the Nude Mouse," *Clin. Exp. Metastasis* 14:246–252 (1996).

Zhu, Y., "Molecular Cloning and Sequencing of DNA Repair Gene $RAD_{24}$," *Chinese Biochemical Journal* 11(5):541–550 (1995).

Parker et al., "Identification of a Human Homologue of the *Schizosaccharomyces pombe* rad17+ Checkpoint Gene," *J. Biol. Chem.* 273(29):18340–18346 (1998).

Berger et al., "Chromosomes in Kidney, Ureter, and Bladder Cancer," *Cancer Genet Cytogenet* 23:1–24 (1986).

Morgan et al., "Inversion of Chromosome 5 Long Arm in Region of Cell Growth Gene Cluster in Hematologic Disorders," *Cancer Genet Cytogenet* 32:267–275 (1988).

Lieberman et al., "A Human Homolog of the *Schizosaccharomyces pombe* rad9+ Checkpoint Control Gene," *Proc. Natl. Acad. Sci. USA* 93:13890–13895 (1996).

Holliday et al., "Genetic Characterization of rec–1, a Mutant of *Ustilago maydis* Defective in Repair and Recombination," 27:314–453 (1976).

Lalande et al., "Molecular Detection and Differentiation of Deletions in Band 13q14 in Human Retinoblastoma," *Cancer Genet Cytogenet* 23:151–157 (1986).

Dyer et al., "A New Human T–Cell Lymphoma Cell Line (Karpas 384) of the T–Cell Receptor Gamma/Delta Lineage with Translocation t(7:14) (p13;q11.2)," *Leukemia* 7(7):1047–1053 (1993).

* cited by examiner

FIG. 1

G2 Cell Cycle Checkpoint Homologs

| S. cerevisiae | S. pombe | Human | Possible Function |
|---|---|---|---|
| RAD24 | rad17 | yes | Clamp loading / unloading? |
| RAD17 | rad1 | yes | exonuclease? |
| MEC3 | — | — | — |
| RAD9 | — | — | — |
| — | hus1 | yes | — |
| — | rad9 | yes | — |
| — | rad26 | ? | — |
| MEC1/ESR1, TEL1 | rad3 | ATM, ATR | protein kinase |

```
HUMAN   MNQVTDWVDPSFDDFLECSGVSTITATSLGVNNSSHRRKNGPSTLESSRFPARKRGNLSS        60
DROME   MN-LITSPAPS-------ESTPAKRTRSASNVSSSRVSRTPSINTKPIQIPDVDSVDLTA        54
CAEEL   --------------------------------------------------------------      0
POMBE   MRRQLSFHEST-KRSLKKKIRKIEKPSLV--SKTSRDKNASIT-------DIHEEDIEA         50
YEAST   MDSTNLNKRPLLQYSLSLGSQITKWSSRPTSPVRKARSTENDFLSKQ----DTSSILPS         57

HUMAN   LEQIYGLENSKEYLSEN--EPWVDKYKPETQHELAVHKKKIEEVETWLKAQVLERQPKQG       118
DROME   MDDDQDADITVPPPEVK--ENMMESFEPATSDDLAVHPKKVGELRDWLR-HCEAVRKKFP       111
CAEEL   --VMYLTGPAGSGKSTTV-------------DLLTIELAPRRDELQIHNKKIAEVDHWLKNVFSESNKQLG  47
POMBE   FJDEENKIVHLNNLKEDRFQLMFEKYIPQKAADLAVHKSKISATKQWMLTDSLESR----       106
YEAST   INDGG-----------EQWYEKFKPNCLEQVAIHKRKLKDVQEALDAMFLPNAKH----       102

HUMAN   GSILLITGPPGCGKTTTLKILSKEHGIQVQEWINPVLPDFQKDDFK-GMFNTESSFHMFP       177
DROME   AQMCLLTGPTGAGKTTTLRVLAKEFGYQLQEWINPI--CEVVNTL-GDQTTGASY----       164
CAEEL   --VMYLTGPAGSGKSTTVEVMCTEQNIEIIEYSPEYLHNEDFECEK-PDFTQ-------        96
POMBE   LLLICGPSGCGKSTAVQVLAKELGYSLIEWLNPMNLKEPSNQES-DTLSLTEKFSRF-       162
YEAST   RILLSGPSGCSKSTVIKELSKILVPKYRQNSNGTSFRSTPNEHKVTEFRGDCIVNDLP       161

HUMAN   YQSQIAVFKEFLLRATKYNKLQMLGDDLRTDKKILVEDLPNQF-YRDSHT-LHEVLRK-       234
DROME   VGSHLEAFKSFLLRASRYKSL--LDSQ---NKRLLVEDFPNVL-LSDKEVNFEELEE-       217
CAEEL   ---LRRFLLR--RHGSLR-------RGGL--KKRLLLVTELPDQA-YSDAEK-FREDLSEV       141
POMBE   MSLCETYPELELMDS--NNIQKRGKNAQGKKKFIFLDEIPHLSKFNGSLDAFRNVIRTA       219
YEAST   --QMESFSEF-LKGARYLVMSNLS-------------LILIEDLPNVFHI-DTRRFQQLILQW    208
```

FIG. 2A

```
HUMAN   Y V R I G R - - - - - - - C P L I F I S D S L S G D N N - - - - - - - - - - - - - - - - - - - - - - - - - - Q R L - L F P K E I Q E E C S I S N I S F N P V   279
DROME   Y T A Y G K - - - - - - - S P L V F I V A D A K S R G L N - - - - - - - - - - - - - - - - - - - - - - - - I S Y R L F P D Q L K A K H R I E H I S F N A I   263
CAEEL   L Q H I - W - - - - - - H P V I F C L T N S I A C W N L - - - - - - - - - - - - - - - - - - - - - - - - - - - - - - - - - - - - - - - - - - - - - - - - - 186
POMBE   L T S R G A - - - - F S I M V L T E I Q L N N L E G I N S Q - - D R N S F N S V Q I M G N D L L Q D P R V T V L Q F N P V   275
YEAST   L Y S E P L L P P L V I C I T E C E I P E N D N N Y R K F G I D Y T F S A E T I M N K E I L M H P R L K R I K F N P I   268

HUMAN   A P T I M K F L N R I V T I E A N K N G G K I T V P - D K T S L E L L C Q G C S G D I R S A I N S L C F S S S - - - -   334
DROME   A S T I M Q K S M K T F C S V - M Q Q N K A T Y K V P - S T A V V D S I V V G A Q G D I R N A L I N L H L S S L - - -   317
CAEEL   A D S F M K K A L - - - - - - - - - - - - - - - - V R A S N C L S S P L S D A K L N V I G E E A G G D L R I A M M L Q M N S - - -   233
POMBE   A P T Y M K K C L G S I L R K E G V P K S P K L - - L S L V E N I C S A S E G D L R S A I N S L Q L S I S Q S F E   330
YEAST   N S T L L K K H L K F I C V Q N M L K E K N K W N K R Q E V I D Y I A Q E T - G D I R S A I T T L Q F W A T S S -   325

HUMAN   - K G E N N L R P - - - - - - - - - - R K K G M S - L K S D A V L S K - S K R R K K P D R V F E N Q E V Q A I G G - -   378
DROME   - K G V S S M P T - - - - - - - - - - K Q L N V S - V S A K G - - - - - - - R K K K M Q S T L K S I G - - - - - - - - -   349
CAEEL   - - - - - - - - - - - - - - - - I G P N A D R R S G N S - - - - - - V I C A S K A N R - - - - - - - - - - - - - - - - - - - - - - -   257
POMBE   K K G T K N I R E V K E G K G K G N D F S - - L E A A Q V E E R L S K S D S E A Y A R F K N Y K S A Y I P K S D K N E N S   389
YEAST   - - - G S L - - - P I S T R E S T I S Y F H A I G K V I H G S H S T N N D N E M I N N L - - - F E N S N N L   370

HUMAN   - - - - K D V S L F L F R A L G K I L Y C K R A S L T E L D S P R L P S H L S E Y E - - - - R D T L L V E P E E V V   428
DROME   - - - - R D E S I T L M H A L G R V L N P K F N E - - - - - - - - - - - - - - - - - - - - - D K T M L H S P E E I T   382
CAEEL   F - - - - - - H M I G R I L Y A K R V N P N V P K P S R F S K R R R K S A P I P E P L V R T E L E H D P T D I I   307
POMBE   F K K D V G L G M M H A I G K V V W N K R E G D - - - - - - - - - - - - - - - - - - - - - D E V L K A S S Q Q T G   426
YEAST   L S K E D F K L G I L E N Y N T F - - - N K G E F S I S D A S I V D C L S E C D N - - - - - M N G L P E S N E Y G L   421
```

```
HUMAN  S A Q G D M E E N I I E D Y E S D G T   670
DROME                                          520
CAEEL  T I E E S S D D S - - F E E F           514
POMBE  - - - L I D D P - - I E D E D           606
YEAST  P V I S E S - - - - L S D S D L E I L   659
```

```
HUMAN  ------------------------------FRLSTFGNAGSSHLDYP----------------------KIS  226
MOUSE  ------------------------------FRLSTFGNAGNSHLDYP----------------------KLS  226
CAEEL  ------------------------------F--TTFGDVGETTVSIP----------------------LLS  215
POMBE  ------------------------------FLRCVGALSTTEIEYP-------------------RFS  232
USTMA  KRNTSASMLKFRAISDTGSSEMEFPASLTSSDPTGVIEKFVALPGSSEQW---------DFT  287
YEAST  ---NDENVEALISKSQLGFSKIKLP---SNRSILEKLQVFDGSTVIDGFAVIGFFDFT  240

HUMAN  LLKPSTKALVLSCKVSIRTDNRGFLSLQYMIRNEDGQICFVEYYCCPDEEVPESES  282
MOUSE  LLKPSTKALALSCKVSIRTDNRGFLSLQYMIRNEDGQICFVEYYCCPDEEVPES-  280
CAEEL  LIQRMTTAFILATKLILRVDERGVLSCQFSIDHGEGNASYIEFLTVPADE--EE  267
POMBE  LIRHALKALQVGSKVNLRIDENGTLSIQIMLVGQEGLCTFVDECIVPLDLVSEDEEDEE  323
USTMA  LLSRTMSVLRSSIKTSLRMDEAGLISFQFMMPEYPRAAAGAPLTNAAAGQAAHEDEQDA  363
YEAST  SFDKIRKSTKIASKVLFRMDVHGVLSVNILSQTDDVILDTTRPSNNRPGSIRQLQLPKD  318

HUMAN
MOUSE
CAEEL
POMBE  EEPAESNQSDNNVLRNDPNYRGDAETEDEDS
USTMA  FCEFL----CCPLDTSTLIV
YEAST  YPGIVIEV----CMLEKESIDE
```

*FIG. 3B*

```
HUMAN  MKFRAKIVDGACLNHFTRISNMIAKLAKTCTLRISPDKLN      40
MOUSE  MKFRAKIVDLACLNHFTRVSNMIAKLAKTCTLRISPEKLN      40
POMBE  MREKTRISN---LYTLTRLVQALDKIGRFCWLRLMPETVN      37

HUMAN  FILCDKLANGGVSMWCELEQENFNEFQMEGVSAENNEIY        80
MOUSE  FILCDKLASGGVSMWCELEQENFSEFQMEGVSEENNEIY        80
POMBE  EVIVPDFRMTQV--WSVLEVETIFEDYVVQ--SNADNVIN       73

HUMAN  LELTSENLSRALKTAQNARALKIKLTNKHFPCLTVSVEL-      119
MOUSE  LELTSENLSRALKTAQNSRALKIKLTNKHFPCLTVSVELQ      120
POMBE  LEVPIDNFYKALRSAANASDSTVRLSKKNNQPLLSLSTTW      113

HUMAN  LSMSSSSRIVTHDIPIKVIPRKLWKDLQEPVVPDPDVSIY      159
MOUSE  VSSSSSRIVVHDIPIKVLPRRLWKDLQEPSIPDCDVSIC       160
POMBE  SGRAFGSNIVTHNIPVRVLSQSYVSVIKEPTAPEPDCHIF      153
```

*FIG. 4A*

```
HUMAN  LPVLKTMKSVVEKMKNISNHLVIEANLDGELNLKIETELV 199
MOUSE  LPALKMKSVVEKMRNISNQLVIEANLKGELNLKIETELV 200
POMBE  LPQLNFLRHVVDKRYKSLSDRIIMSANMSGELQLSVNIPSA 193

HUMAN  CVTTHFKDLGNPPLASESTHE------DRNVEHMAEVHI 232
MOUSE  CVTTHFKDLENPLLPSDSVSQ------NRHPEDMAKVHI 233
POMBE  RVSTKWKGLENPELDPSQVEDISRHPSQTRAPEEFVHMRL 233

HUMAN  DIRKLLQFLAGQQVNPTKALCNIVNNKMVHFDDLLHE--- 268
MOUSE  DIKKLLQFLAGQQVTPTKAVCNIVNNRTVHFDLLE--- 269
POMBE  DSKDLVNMLKISSVAKRVIACFCEGHALVLYVYITDPEDE 273

HUMAN  -DVSLQYFIPA-LS           280
MOUSE  -DVSLQYFIPA-LS           281
POMBE  HTAVLTYYISTYVD           287
```

*FIG. 4B*

DNA MOLECULES ENCODING SINGLE STRAND GAP RESPONSE PROTEINS INVOLVED IN ACTIVATION OF A DNA REPAIR/CELL CYCLE CHECKPOINT PATHWAY

This application claims the benefit of U.S. Provisional Patent Application Serial No. 60/082,020, filed Apr. 16, 1998.

This invention was as a result of research funded by grant number GM54705-03 from the National Institute of Health. The U.S. Government may have certain rights in this invention.

FIELD OF THE INVENTION

The present invention relates to isolated DNA molecules encoding single strand gap response proteins involved in activation of a DNA repair/cell cycle checkpoint pathway, as well as diagnostic and therapeutic uses of the DNA molecules, their expressed proteins or polypeptides, and antibodies raised against the proteins or polypeptides.

BACKGROUND OF THE INVENTION

The progression of a eukaryotic cell through the stages of the cell cycle can be arrested if the events of the previous stage of the cell cycle, such as DNA replication, have not been completed or, in addition, if the DNA has sustained some type of damage. The controls on cell cycle progression are termed checkpoints (Hartwell, L., et al., "Checkpoints: Controls That Ensure the Order of Cell Cycle Events," *Science*, 246:629–34 (1989)), and they can be used to detect whether the processes of the individual stages of the cell cycle have been completed and whether the DNA is intact or in need of repair. Genes whose expressed products are involved in cell cycle delay or DNA repair are broadly defined as checkpoint control genes. Cells that are mutated in one of the cell cycle checkpoint control genes, however, are able to proceed from one stage of the cell cycle to the next even if the cellular processes of that stage are incomplete or in the presence of DNA damage. The G2 phase of the cell cycle lies between S phase, in which DNA replication takes place, and M phase, when mitosis occurs. Thus, the G2 checkpoint is critical for ensuring that mitosis does not occur until all the necessary steps of DNA replication, DNA repair, and chromosome duplication are complete.

Many checkpoint-deficient mutants have been identified in the budding yeast *Saccharomyces cerevisiae* and in the fission yeast *Schizosaccharomyces pombe*.

Genes have been isolated that link mitosis to the completion of DNA replication. Enoch, T., et al., "Mutation of Fission Yeast Cell Cycle Control Genes Abolishes Dependence of Mitosis on DNA Replication," *Cell*, 60:665–73 (1990); Enoch, T., et al., "Fission Yeast Genes Involved in Coupling Mitosis to Completion of DNA Replication," *Genes Dev.*, 6:2035–46 (1992); McFarlane, R. J., et al., "Characterization of the *Schizosaccharomyes pombe* rad4/cut5 Mutant Phenotypes: Dissection of DNA Replication and G2 Checkpoint Control Function," *Mol. Gen. Genet.*, 255:332–40 (1997). In addition, many genes that function in DNA repair have been identified as G2 checkpoint control genes. Nasim, A., et al., "Genetic Control of Radiation Sensitivity in *Schizosaccharomyces pombe*," *Genetics*, 79:573–82 (1975); Al-Khodairy, F., et al., "DNA Repair Mutants Defining G2 Checkpoint Pathways in *Schizosaccharomyces pombe*," *EMBO J.*, 11:1343–50 (1992); Al-Khodairy, F., et al., "Identification and Characterization of New Elements Involved in Checkpoint and Feedback Controls in Fission Yeast," *Mol. Biol. Cell*, 5:147–60 (1994). Several examples include *Saccharomyces cerevisiae* RAD9 (Weinert, T. A., et al., "Characterization of RAD9 of *Saccharomyces cerevisiae* and Evidence that Its Function Acts Post-Translationally in Cell Cycle Arrest after DNA Damage," *Mol. Cell. Biol.*, 10:6554–64 (1990)), *Saccharomyces cerevisiae* MEC3 (Weinert, T. A., et al., "Mitotic Checkpoint Genes in Budding Yeast and the Dependence of Mitosis on DNA Replication and Repair," *Genes & Dev.*, 8:652–65 (1994)), *Schizosaccharomyces pombe* rad1 (Rowley, R., et al., "Checkpoint Controls in *Schizosaccharomyces pombe*: rad1," *EMBO J.*, 11:1335–42 (1992)), *Schizosaccharomyces pombe* rad3 (Jimenez, G., et al., "The rad3+ Gene of *Schizosaccharomyces pombe* is Involved in Multiple Checkpoint Functions and in DNA Repair," *Proc. Natl. Acad. Sci. USA*, 89:4952–56 (1992); Bentley, N. J., et al., "The *Schizosaccharomyces pombe* rad3 Checkpoint Gene," *EMBO J.*, 15:6641–51 (1996)), *Schizosaccharomyces pombe* rad17 (Griffiths, D. J. F., et al., "Fission Yeast rad17: a Homolog of Budding Yeast RAD24 That Shares Regions of Sequence Similarity with DNA Polymerase Accessory Proteins," *EMBO J.*, 14:5812–23 (1995)), *Schizosaccharomyces pombe* hus1 (Kostrub, C. F., et al., "Molecular Analysis of hus1+, a Fission Yeast Gene Required for S-M and DNA Damage Checkpoints," *Mol. Gen. Genet.*, 254:389–99 (1997)), and the fungus *Ustilago maydis* REC1 (One1, K., et al., "The REC1 Gene of *Ustilago maydis*. Which Encodes a 3'-5' Exonuclease, Couples DNA Repair and Completion of DNA Synthesis to a Mitotic Checkpoint," *Genetics*, 143:165–74 (1996)). A number of reviews summarize this work. Sheldrick, K. S., et al., "Feedback Controls and G2 Checkpoints: Fission Yeast as a Model System," *BioEssays*, 15:775–82 (1993); Lydall, D., et al., "From DNA Damage to Cell Cycle Arrest and Suicide: A Budding Yeast Perspective," *Curr. Opin. Genet. Dir.* 6:4–11 (1996); Stewart, E., et al., "S-phase and DNA-damage Checkpoints: a Tale of Two Yeasts," *Curr. Opin. Cell Biol.*, 8:781–87 (1996); Carr, A. M., "Control of Cell Cycle Arrest by the Mec1$^{sc}$/Rad3$^{sp}$ DNA Structure Checkpoint Pathway," *Curr. Opin. Genet. Dev.*, 7:93–98 (1997). Some of the *Saccharomyces cerevisiae* and *Schizosaccharomyces pombe* genes involved in the G2 cell cycle checkpoint are summarized in FIG. 1.

A human homolog of the *Schizosaccharomyces pombe* rad9 checkpoint control gene was described recently. Lieberman, H. B., et al., "A Human Homolog of the *Schizosaccharomyces pombe* rad9+ Checkpoint Control Gene," *Proc. Natl. Acad. Sci. USA*, 93:13890–95 (1996). The mapping of a human homolog to *Schizosaccharomyces pombe* rad1 was reported. Parker, A., et al., "Identification of a Putative Human Homolog of the *Schizosaccharomyces pombe* rad1 Checkpoint Gene", *Eukayrotic DNA Replication*, p. 179, Cold Spring Harbor Laboratory Press, Cold Spring Harbor, N.Y. (1997). Interestingly, referring to FIG. 1, two *Saccharomyces cerevisiae* genes, MEC3 and RAD9, do not appear to have *Schizosaccharomyces pombe* or human homologs, while *Saccharomyces cerevisiae* does not carry homologs for *Schizosaccharomyces pombe* hus1 or rad9. The checkpoint control systems of *Saccharomyces cerevisiae* and *Schizosaccharomyces pombe* have some gene homologs in common; however, they appear to have diverged significantly, perhaps because cell division is so different in these organisms. *Saccharomyces cerevisiae* divides by budding, while *Schizosaccharomyces pombe* divides by fission. The mitosis and cell division of *Schizosaccharomyces pombe* is much more similar to that of human cells than the mitosis and cell division of *Saccharomyces cerevisiae*. *Schizosaccharomyces pombe* has a distinct G2 phase of the cell cycle and, in addition, the chromosomes undergo condensation during mitosis. Russell, P., et al., "*Schizosaccharomyces pombe* and *Saccharomyces cerevisiae*: A Look at Yeasts Divided," *Cell*, 45:781–82 (1986). This may be why the human genes of the G2 cell cycle checkpoint pathway correspond so much more closely to the genes of *Schizosaccharomyces pombe* than to the genes of *Saccharomyces cerevisiae*.

The occurrence of mutations in checkpoint control genes of higher eukaryotes can lead to cancer. Hartwell, L., "Defects in a Cell Cycle Checkpoint may be Responsible for the Genomic Instability of Cancer Cells," *Cell*, 71:543–46 (1992); Hartwell, L., et al., "Cell Cycle Control and Cancer," *Science*, 266:1821–28 (1994); Kastan, M. B., et al., "Participation of p53 Protein in the Cellular Response to DNA Damage," *Cancer Res.*, 51:6304–11 (1991); Kuerbitz, S. J., et al., "Wild-Type p53 is a Cell Cycle Checkpoint Determinant Following Irradiation," *Proc. Natl. Acad. Sci. USA*, 89:7491–95 (1992). Genes which, when mutated, allow increased rates of tumor formation are termed tumor suppressors. Many tumor suppressors have cell cycle checkpoint function, and loss-of-function mutations in these genes causes runaway cell proliferation, leading to tumor formation. Collins, K., et al., "The Cell Cycle and Cancer," *Proc. Natl. Acad. Sci. USA*, 94:2776–78 (1997). For example, ATM has been identified as the gene that is defective in patients with ataxia telangiectasia. As seen in FIG. 1, ATM is the human homolog of *Saccharomyces cerevisiae* MEC1/ESR1 and *Schizosaccharomyces pombe* rad3. Nowak, R., "Discovery of AT Gene Sparks Biomedical Research Bonanza," *Science*, 268:1700–01 (1995); reviewed by Enoch, T., et al., "Cellular Responses to DNA Damage: Cell-Cycle Checkpoints, Apoptosis and the Roles of p53 and ATM," *Trends Biochem. Sci.*, 20:426–30 (1995); Lehmann, A. R., et al., "The Ataxia-Telangiectasia Gene: a Link Between Checkpoint Controls, Neurodegeneration, and Cancer," *Trends Genet.*, 11:375–77 (1995); Jackson, S. P., "The Recognition of DNA Damage," *Curr. Opin. Genet. Dev.*, 6:19–25 (1996). These proteins have protein kinase activity and are involved in generating a signal to halt progression through the cell cycle in response to DNA damage.

The genes of G2 cell cycle checkpoint function in a number of cellular contexts in both *Schizosaccharomyces pombe* and *Saccharomyces cerevisiae*. One such function involves causing a G2 phase-specific cell cycle arrest in response to DNA damage from UV or gamma-irradiation, thereby blocking the onset of mitosis. In this instance, they are responding to DNA damage-specific structures. In *Schizosaccharomyces pombe*, this is mediated by the Chk1 protein kinase. Walworth, N. C., et al. "rad-Dependent Response of the ChK1-Encoded Protein Kinase at the DNA Damage Checkpoint," *Science*, 271:353–56 (1996). Another function involves causing a delay of S-phase and allowing S-phase recovery in response to stalled DNA replication, as can be induced by exposure of cells to hydroxyurea. In this case, the genes are responding to a DNA replication-specific structure. In *Schizosaccharomyces pombe*, this is mediated by the Cds1 protein kinase. Lindsay, H. M., et al., "S-Phase-Specific Activation of Cds1 Kinase Defines a Subpathway of the Checkpoint Response in Schizosaccharomyces pombe," *Genes Div.* 12:382–95 (1998). Finally, in *Saccharomyces cerevisiae*, these genes induce a G2 arrest upon inactivation of a cdc13 temperature-sensitive mutant. Lydall, D., et. al., "Yeast Checkpoint Genes in DNA Damage Processing: Implications for Repair and Arrest," *Science*, 270:1488–91 (1995). Inactivation of cdc13 results in the appearance of single stranded TG-rich regions at telomeres due to a specific loss of the AC-rich DNA strands.

The unifying principle in these instances is activation of the cell cycle checkpoint pathway by regions of single stranded DNA. After DNA damage, such as by UV or gamma-irradiation, a single strand gap is created by excision of a length of DNA containing the damaged nucleotides. Sancar, A., "Excision Repair in Mammalian Cells," *J. Biol. Chem.*, 270:15915–18 (1995). The stalling of DNA replication forks will normally result in a single strand region on the lagging strand, even if the leading strand is fully replicated up to the point at which the parental DNA strands have not been unwound and remain duplexed. Impaired functioning of *Saccharomyces cerevisiae* cdc13 renders the telomeric TG strand single stranded, perhaps due to a reduced protection of the CA strand from degradation. Garvik, B., et al., "Single-Stranded DNA Arising at Telomeres in cdc13 Mutants May Constitute a Specific Signal for the RAD9 Checkpoint," *Mol. Cell. Biol.*, 15:6128–38 (1995); Nugent, C. I., et al., "Cdc13p: A Single-Strand Telomeric DNA-Binding Protein with a Dual Role in Yeast Telomere Maintenance," *Science*, 274:249–52 (1996); Lin, J. J., et al., "The Saccharomyces CDC13 Protein is a Single-Strand $TGI_{1-3}$ Telomeric DNA-binding Protein in vitro that Affects Telomere Behavior in vivo," *Proc. Natl. Acad. Sci. USA*, 93:13760–65 (1996). Thus, these specific checkpoint control genes appear to monitor the intactness of cellular DNA by responding to the generation of single stranded regions. They act in concert with one another to slow S phase or induce G2 arrest when single stranded gaps appear in the DNA. As such, they constitute genes of a distinct pathway of the G2 cell cycle checkpoint—i.e. the "single strand gap response" (SSGR) pathway. Genes involved in the SSGR pathway are specifically defined as "single strand gap response" (SSGR) genes.

Researchers have isolated and sequenced several SSGR genes in *Schizosaccharomyces pombe* and *Saccharomyces cerevisiae*.

The gene for *Schizosaccharomyces pombe* rad17 has been described in Griffiths, D. J. F., et al., "Fission Yeast rad17: a Homolog of Budding Yeast RAD24 That Shares Regions of Sequence Similarity with DNA Polymerase Accessory Proteins," *EMBO J.*, 14:5812–23 (1995). The gene for its homolog in *Saccharomyces cerevisiae*, RAD24, has been deposited in EMBL/Genbank/DDBJ data banks, which are publicly available databases. Zhu, Y. B., et al., "Molecular Cloning and Sequencing of DNA Repair Gene RAD24, *Chinese Biochem. J.*, 11:541–50 (1995). Cloning of *Schizosaccharomyces pombe* rad17 revealed that it has extensive homology to the DNA polymerase accessory proteins known as clamp loaders. Griffiths, D. J. F., et al., "Fission Yeast rad17: a Homolog of Budding Yeast RAD24 That Shares Regions of Sequence Similarity with DNA Polymerase Accessory Proteins," *EMBO J.*, 14:5812–23 (1995). This suggests that *Schizosaccharomyces pombe* rad17 may carry out a clamp loading or unloading function in the DNA repair pathway. Interestingly, while the *Schizosaccharomyces pombe* rad17 gene carries out two roles, DNA repair and cell cycle checkpoint regulation, the two functions, are separable. Specific point mutations of rad17 were generated that abolished DNA repair activity but did not affect checkpoint control. Griffiths, D. J. F., et al., "Fission Yeast rad17: a Homolog of Budding Yeast RAD24 That Shares Regions of Sequence Similarity with DNA Polymerase Accessory Proteins," *EMBO J.*, 14:5812–23 (1995).

The cloning of the gene for *Schizosaccharomyces pombe* rad1 has been described in a series of reports. Sunnerhagen, P., et al., "Cloning and Analysis of a Gene Involved in DNA Repair and Recombination, the rad1 Gene of *Schizosaccharomyces pombe,*" *Mol. Cell. Biol.*, 10:3750–60 (1990); Rowley, R., et al., "Checkpoint Controls in *Schizosaccharomyces pombe*: rad1," *EMBO J.*, 11:1335–42 (1992); Long, K. E., et al., "The *Schizosaccharomyces pombe* rad1 Gene Consists of Three Exons and the cDNA Sequence is Partially Homologous to the *Ustilago maydis* REC1 cDNA," *Gene*, 148:155–59 (1994). The cloning of its *Saccharomyces cerevisiae* homolog, RAD17, has also been described in Siede, W., et al., "Cloning and Characterization of RAD17, a Gene Controlling Cell Cycle Responses to DNA Damage in *Saccharomyces cerevisiae,*" *Nuc. Acids Res.*, 24:1669–75 (1996). Extensive work has been carried out over a number of years concerning its homolog in Ustilago maydis, REC1. Holliday, R., et al., "Genetic Characterization of rec-1, a Mutant of *Ustilago maydis* Defective in Repair and Recombination," *Genet. Res.*, 27:413–53 (1976); Holden, D. W., et al., "Nucleotide Sequence of the REC1 Gene of *Ustilago maydis,*" *Nuc. Acids Res.*, 17:10489 (1989); Tsukuda, T., et al., "Isolation of the REC1 Gene Controlling Recombination in *Ustilago maydis,*" *Gene*, 85:335–41 (1989). An exonuclease activity is associated with the protein (Thelen, M. P., et al., "The REC1 Gene of *Ustilago maydis* Involved in the Cellular Response to DNA Damage Encodes an Exonuclease," *J. Biol. Chem.*, 269:747–54 (1994)), and the role of the gene in DNA repair and cell cycle regulation is known (Onel, K., et al., "Mutation Avoidance and DNA Repair Proficiency in *Ustilago maydis* Are Differentially Lost with Progressive Truncation of the REC1 Gene Product," *Mol. Cell. Biol.*, 15:5329–38 (1995); Onel, K., et al., "The REC1 Gene of *Ustilago maydis*, Which Encodes a 3'–5' Exonuclease, Couples DNA Repair and Completion of DNA Synthesis to a Mitotic Checkpoint," *Genetics*, 143:165–74 (1996)).

Recent studies offer some insight into the in vivo role of the *Saccharomyces cerevisiae* checkpoint genes. Lydall D., et al., "Yeast Checkpoint Genes in DNA Damage Processing: Implications for Repair and Arrest," *Science*, 270:1488–91 (1995). The Rad24, Rad17, and Mec3 proteins appear to activate an exonuclease activity in vivo, while the Rad9 protein appears to modulate exonuclease activity. It was suggested that *Saccharomyces cerevisiae* Rad 17 protein may actually be an exonuclease, based on homology between it and *U. maydis* Rec1.

The cloning of *Schizosaccharomyces pombe* hus1 was described recently. Kostrub, C. F., et al., "Molecular Analysis of hus1+, a Fission Yeast Gene Required for S-M and DNA Damage Checkpoints," *Mol. Gen. Genet.*, 254:389–99 (1997). Yeast strains disrupted in hus1 are viable but are checkpoint-defective.

It is expected that the mammalian homologs of the SSGR genes of *Schizosaccharomyces pombe* will also carry out an SSGR function in human cells, and are likely candidates for human tumor suppressor genes. However, no mammalian, particularly human, SSGR genes have been cloned. The present invention is directed to overcoming this deficiency in the art.

SUMMARY OF THE INVENTION

The present invention relates to isolated DNA molecules encoding mammalian "single strand gap response" (SSGR) proteins involved in activation of a DNA repair/cell cycle checkpoint pathway. In particular, the isolated DNA molecules include the human HRAD17, human HRAD1, human HHUS1, mouse HRAD1, and mouse HHUS1 DNA molecules. The present invention is also directed to proteins or polypeptides encoded by the DNA molecules as well as antibodies raised against those proteins or polypeptides. Expression systems and host cells transformed with these DNA molecules are also disclosed.

The DNA molecules of the present invention are useful in detecting the presence of genes encoding SSGR proteins in a tissue sample. This may be useful in identifying the presence of mutants in germline tissue samples, which indicates the potential for development of inheritable diseases, and in tumor samples, which indicates the particular mutation attributable to tumor formation and, therefore, may identify suitable treatment regimen.

The DNA molecules of the present invention can also be used in gene therapy to restore proper cell cycle regulation to cells. This is particularly useful in halting or reversing a cancerous or pre-cancerous condition.

The proteins or polypeptides of the present invention can be utilized to detect the presence of antibodies raised by such proteins or polypeptides in a sample of mammalian origin.

The antibodies or binding portions thereof of the present invention are useful for detecting the presence or absence of the expressed SSGR proteins or polypeptides from a sample.

The present invention also relates to a transgenic animal whose somatic and germ cells lack a gene encoding a SSGR protein or possess a disruption in that gene. This animal is susceptible to spontaneous tumor development and, therefore, is useful for studying tumor formation and treatment.

As tumor supressors, the SSGR proteins act at the G2 cell cycle checkpoint in order to permit complete repair of DNA damage. Their mutation leads to cancer by allowing increased amounts of DNA damage, leading to increased levels of mutation in the cell. Therefore, one benefit of the invention is its use as a tool for the diagnosis of cancers caused by mutations of these genes.

However, there is a second reason for the importance of the SSGR genes with respect to cancer, aside from their role as tumor supressors, and that is as a crucial consideration for chemotherapy. These genes function at the G2 cell cycle checkpoint and act as a barrier to the initiation of mitosis in the presence of unrepaired DNA damage. This barrier allows a cell with DNA damage to halt the cell cycle at the G2 stage for up to 8 hours, or more, and make repeated attempts to repair the DNA damage before allowing mitosis to proceed. This is useful to the cell because entry into mitosis in the presence of high levels of unrepaired DNA damage causes mitotic catastrophe and cell death (e.g., apoptosis). As such, this pathway is of key importance in the problematic survival of cancerous tissue or tumor cells after they are assaulted by chemotherapeutic DNA-damaging agents or radiotherapy.

Since cancers with mutations in the SSGR genes will have an increased susceptibility to DNA-damaging chemotherapeutic agents, it is important to determine whether the SSGR genes are mutated. Identification of cancers carrying mutations in or causing reduced expression of these genes would flag those cancers as being particularly susceptible to DNA-damaging chemotherapeutic agents, as opposed to drugs that poison the cell in other ways.

Furthermore, the SSGR proteins are key targets for anti-cancer drugs in those cancers that do not carry mutations in the SSGR genes. Inhibition of SSGR response protein function in these cancers will heighten the potency of chemotherapeutic DNA-damaging agents. The proteins or polypeptides of the present invention can be used to identify drugs that will inhibit the SSGR pathway and increase the effectiveness of tumor destruction by DNA-damaging agents.

BRIEF DESCRIPTION OF THE DRAWINGS

FIG. 1 shows a summary of the G2 cell cycle checkpoint homologs in *Saccharomyces cerevisiae, Schizosaccharomyces pombe*, and humans.

FIGS. 2A–D show a multiple alignment of the rad17 homologs: Human=*Homo sapiens* (SEQ ID NO:2); Drome=*Drosophila melanogaster* (SEQ ID NO:12); Caeel=*Caenorhabditis elegans* (SEQ ID NO:14); Pombe=*Schizosaccharomyces pombe* (SEQ ID NO:20) (Griffiths, D. J. F., et al., "Fission Yeast rad17: a Homolog of Budding Yeast RAD24 That Shares Regions of Sequence Similarity with DNA Polymerase Accessory Proteins," *EMBO J.,* 14:5812–23 (1995), which is hereby incorporated by reference); Yeast=*Saccharomyces cerevisiae* (SEQ ID NO:21) (EMBL/Genbank/DDBJ data banks (1993), which is hereby incorporated by reference). The rad17 homologs were aligned by the Clustal method using the Megalign program (DNASTAR Inc., Wisconsin). Identical amino acids are indicated by the boxed regions.

FIGS. 3A–B show a multiple alignment of the rad1 homologs: Human=*Homo sapiens* (SEQ ID NO:4); Mouse=*Mus musculus* (SEQ ID NO:6); Caeel=*Caenorhabditis elegans* (SEQ ID NO:16); Pombe=*Schizosaccharomyces pombe* (SEQ ID NO:22)(Long, K. E., et al., "The *Schizosaccharomyces pombe* rad1 Gene Consists of Three Exons and the cDNA Sequence is Partially Homologous to the *Ustilago maydis* REC1 cDNA," *Gene,* 148:155–59 (1994), which is hereby incorporated by reference); Ustma=*Ustilago maydis* (SEQ ID NO:23) (One1, K., et al., "Mutation Avoidance and DNA Repair Proficiency in *Ustilago maydis* Are Differentially Lost with Progressive Truncation of the REC1 Gene Product," *Mol. Cell. Biol.,* 15:5329–38 (1995), which is hereby incorporated by reference); Yeast=*Saccharomyces cerevisiae* (SEQ ID NO:24) (Siede, W., et al., "Cloning and Characterization of RAD17, a Gene Controlling Cell Cycle Responses to DNA Damage in *Saccharomyces cerevisiae,*" *Nuc. Acids Res.,* 24:1669–75 (1996), which is hereby incorporated by reference). The rad1 homologs were aligned by the Clustal method using the Megalign program (DNASTAR Inc., Wisconsin). Amino acids 81 to 145 (indicated by 1) and 191 to 135 (indicated by 2) of the *U. maydis* REC1 sequence, and the last 83 amino acids of the Yeast amino acid sequence are omitted from the figure. Identical amino acids are indicated by the boxed regions.

FIGS. 4A–B show a multiple alignment of the hus1 homologs: Human=*Homo sapiens* (SEQ ID NO:8); Mouse=*Mus musculus* (SEQ ID NO:10); Pombe=*Schizosaccharomyces pombe* (SEQ ID NO:25) (Kostrub, C. F., et al., "Molecular Analysis of hus1+, a Fission Yeast Gene Required for S-M and DNA Damage Checkpoints," *Mol. Gen. Genet.,* 254:389–99 (1997), which is hereby incorporated by reference). The hus1 homologs were aligned by the Clustal method using the Megalign program (DNASTAR Inc., Wisconsin). Identical amino acids are indicated by the boxed regions.

FIG. 6A shows an elution profile of Hrad1 from a Hi Trap (Pharmacia) metal chelate column. Hrad1 elution starts at 170 mM imidazole. The molecular weight of the tagged Hrad1 is about 34 kDa. FIG. 6B shows an elution profile of Hrad1 from a MonoQ column. Hrad1 elutes at approximately 150 mM NaCl.

DETAILED DESCRIPTION OF THE INVENTION

Figure 5:
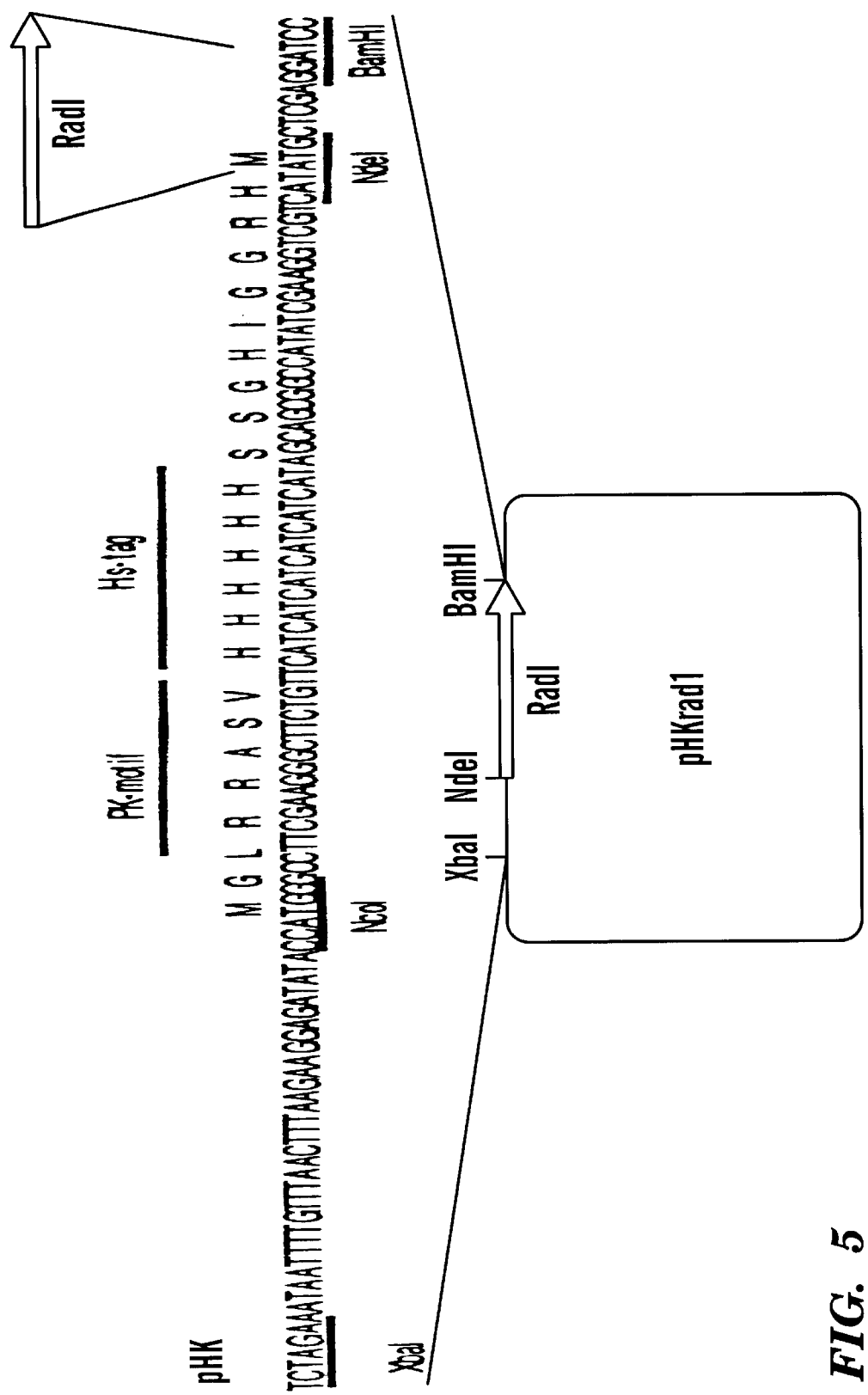
FIG. 5 shows a human HRAD1 expression vector. The pHK vector is a modified version of a pET-16b vector (Novagen). It carries a cAMP-dependent protein kinase site, six-histidine tag, and Factor Xa site cloned into the XbaI and BamHI sites of pET-16b. The nucleotide sequence of the region between and including the XbaI and BamHI sites is shown (SEQ. ID. No 26). The amino acid sequence (SEQ. ID. No. 27) encoded by this region is also shown above the nucleotide sequence. The HRAD1 gene is inserted between the NdeI and BamHI sites such that the initiating Met of Hrad1 is encoded within the NdeI site. Insertion of the HRAD1 gene into a pHK vector resulted in removal of the intervening nucleotides (between the NdeI and BamHI sites).

One aspect of the present invention relates to isolated DNA molecules encoding a mammalian SSGR protein involved in activation of a DNA repair/cell cycle checkpoint pathway. One of these DNA molecules, identified as human HRAD17, comprises the nucleotide sequence corresponding to SEQ. ID. No. 1 as follows:

```
ATGAATCAGG TAACAGACTG GGTTGACCCA TCATTTGATG ATTTTCTAGA GTGTAGTGGC    60

GTCTCTACTA TTACTGCCAC ATCATTAGGT GTGAATAACT CAAGTCATAG AAGAAAAAAT    120

GGGCCTTCTA CATTAGAAAG CAGCAGATTT CCAGCGAGAA AAAGAGGAAA TCTATCTTCC    180

TTAGAACAGA TTTATGGTTT AGAAAATTCA AAAGAATATC TGTCTGAAAA TGAACCATGG    240

GTGGATAAAT ATAAACCAGA AACTCAGCAT GAACTTGCTG TGCATAAAAA GAAAATTGAA    300
```

```
                                    -continued
GAAGTCGAAA CCTGGTTAAA AGCTCAAGTT TTAGAAAGGC AACCAAAACA GGGTGGATCT    360

ATTTTATTAA TAACAGGTCC TCCTGGATGT GGAAAGACAA CGACCTTAAA AATACTATCA    420

AAGGAGCATG GTATTCAAGT ACAAGAGTGG ATTAATCCAG TTTTACCAGA CTTCCAAAAA    480

GATGATTTCA AGGGGATGTT TAATACTGAA TCAAGCTTCC ATATGTTTCC CTATCAGTCT    540

CAGATAGCAG TTTTCAAAGA GTTTCTACTA AGAGCGACAA AGTATAACAA GTTACAAATG    600

CTTGGAGATG ATCTGAGAAC TGATAAGAAG ATAATTCTGG TTGAAGATTT ACCTAACCAG    660

TTTTATCGGG ATTCTCATAC TTTACATGAA GTTCTAAGGA AGTATGTGAG GATTGGTCGA    720

TGTCCTCTTA TATTTATAAT CTCGGACAGT CTCAGTGGAG ATAATAATCA AAGGTTATTG    780

TTTCCCAAAG AAATTCAGGA AGAGTGTTCT ATCTCAAATA TTAGTTTCAA CCCTGTGGCA    840

CCAACAATTA TGATGAAATT TCTTAATCGA ATAGTGACTA TAGAAGCTAA CAAGAATGGA    900

GGAAAAATTA CTGTCCCTGA CAAAACTTCT CTAGAGTTGC TCTGTCAGGG ATGTTCTGGT    960

GATATCAGAA GTGCAATAAA CAGCCTCCAG TTTTCTTCTT CAAAAGGAGA AAACAACTTA   1020

CGGCCAAGGA AAAAGGAAT GTCTTTAAAA TCAGATGCTG TGCTGTCAAA ATCAAAACGA   1080

AGAAAAAAAC CTGATAGGGT TTTTGAAAAT CAAGAGGTCC AAGCTATTGG TGGCAAAGAT   1140

GTTTCTCTGT TTCTCTTCAG AGCTTTGGGG AAAATTCTAT ATTGTAAAAG AGCATCTTTA   1200

ACAGAATTAG ACTCACCTCG GTTGCCCTCT CATTTATCAG AATATGAACG GGATACATTA   1260

CTTGTTGAAC CTGAGGAGGT AGTAGAAATG TCACACATGC CTGGAGACTT ATTTAATTTA   1320

TATCTTCACC AAAACTACAT AGATTTCTTC ATGGAAATTG ATGATATTGT GAGAGCCAGT   1380

GAATTTCTGA GTTTTGCAGA TATCCTCAGT GGTGACTGGA ATACACGCTC TTTACTCAGG   1440

GAATATAGCA CATCTATAGC TACGAGAGGT GTGATGCATT CCAACAAAGC CCGAGGATAT   1500

GCTCATTGCC AAGGAGGAGG ATCAAGTTTT CGACCCTTGC ACAAACCTCA GTGGTTTCTA   1560

ATAAATAAAA AGTATCGGGA AAATTGCCTG GCAGCAAAAG CACTTTTTCC TGACTTCTGC   1620

CTACCAGCTT TATGCCTCCA AACTCAGCTA TTGCCATACC TTGCTCTACT AACCATTCCA   1660

ATGAGAAATC AAGCTCAGAT TTCTTTTATC CAAGATATTG GAAGGCTCCC TCTGAAGCGA   1740

CACTTTGGAA GATTGAAAAT GGAAGCCCTG ACTGACAGGG AACATGGAAT GATAGACCCT   1800

GACAGCGGAG ATGAAGCCCA GCTTAATGGA GGACATTCTG CAGAGGAATC TCTGGGTGAA   1860

CCCACTCAAG CCACTGTGCC GGAAACCTGG TCTCTTCCTT TGAGTCAGAA TAGTGCCAGT   1920

GAACTGCCTG CTAGCCAGCC CCAGCCCTTT TCAGCCCAAG GAGACATGGA AGAAAACATA   1980

ATAATAGAAG ACTACGAGAG TGATGGGACA TAG                                2013
```

The DNA molecule corresponding to SEQ. ID. No. 1 encodes a protein or polypeptide, identified as human Hrad17, which is believed to be involved in the single strand gap response pathway. This protein or polypeptide has the deduced amino acid sequence corresponding to SEQ. ID. No. 2 as follows:

```
Met Asn Gln Val Thr Asp Trp Val Asp Pro Ser Phe Asp Phe Leu
1               5                   10                  15

Glu Cys Ser Gly Val Ser Thr Ile Thr Ala Thr Ser Leu Gly Val Asn
                20                  25                  30

Asn Ser Ser His Arg Arg Lys Asn Gly Pro Ser Thr Leu Glu Ser Ser
            35                  40                  45

Arg Phe Pro Ala Arg Lys Arg Gly Asn Leu Ser Ser Leu Glu Gln Ile
            50                  55                  60

Tyr Gly Leu Glu Asn Ser Lys Glu Tyr Leu Ser Glu Asn Glu Pro Trp
65                  70                  75                  80
```

-continued

```
Val Asp Lys Tyr Lys Pro Glu Thr Gln His Glu Leu Ala Val His Lys
                85                  90                  95
Lys Lys Ile Glu Glu Val Glu Thr Trp Leu Lys Ala Gln Val Leu Glu
            100                 105                 110
Arg Gln Pro Lys Gln Gly Gly Ser Ile Leu Leu Ile Thr Gly Pro Pro
        115                 120                 125
Gly Cys Gly Lys Thr Thr Thr Leu Lys Ile Leu Ser Lys Glu His Gly
130                 135                 140
Ile Gln Val Gln Glu Trp Ile Asn Pro Val Leu Pro Asp Phe Gln Lys
145                 150                 155                 160
Asp Asp Phe Lys Gly Met Phe Asn Thr Glu Ser Ser Phe His Met Phe
                165                 170                 175
Pro Tyr Gln Ser Gln Ile Ala Val Phe Lys Glu Phe Leu Leu Arg Ala
            180                 185                 190
Thr Lys Tyr Asn Lys Leu Gln Met Leu Gly Asp Asp Leu Arg Thr Asp
        195                 200                 205
Lys Lys Ile Ile Leu Val Glu Asp Leu Pro Asn Gln Phe Tyr Arg Asp
210                 215                 220
Ser His Thr Leu His Glu Val Leu Arg Lys Tyr Val Arg Ile Gly Arg
225                 230                 235                 240
Cys Pro Leu Ile Phe Ile Ile Ser Asp Ser Leu Ser Gly Asp Asn Asn
                245                 250                 25S
Gln Arg Leu Leu Phe Pro Lys Glu Ile Gln Glu Glu Cys Ser Ile Ser
            260                 265                 270
Asn Ile Ser Phe Asn Pro Val Ala Pro Thr Ile Met Met Lys Phe Leu
        275                 280                 285
Asn Arg Ile Val Thr Ile Glu Ala Asn Lys Asn Gly Gly Lys Ile Thr
290                 295                 300
Val Pro Asp Lys Thr Ser Leu Glu Leu Leu Cys Gln Gly Cys Ser Gly
305                 310                 315                 320
Asp Ile Arg Ser Ala Ile Asn Ser Leu Gln Phe Ser Ser Ser Lys Gly
                325                 330                 335
Glu Asn Asn Leu Arg Pro Arg Lys Lys Gly Met Ser Leu Lys Ser Asp
            340                 345                 350
Ala Val Leu Ser Lys Ser Lys Arg Arg Lys Lys Pro Asp Arg Val Phe
        355                 360                 365
Glu Asn Gln Glu Val Gln Ala Ile Gly Gly Lys Asp Val Ser Leu Phe
370                 375                 380
Leu Phe Arg Ala Leu Gly Lys Ile Leu Tyr Cys Lys Arg Ala Ser Leu
385                 390                 395                 400
Thr Glu Leu Asp Ser Pro Ary Leu Pro Ser His Leu Ser Glu Tyr Glu
                405                 410                 415
Arg Asp Thr Leu Leu Val Glu Pro Glu Val Val Glu Met Ser His
            420                 425                 430
Met Pro Gly Asp Leu Phe Asn Leu Tyr Leu His Gln Asn Tyr Ile Asp
        435                 440                 445
Phe Phe Met Glu Ile Asp Asp Ile Val Arg Ala Ser Glu Phe Leu Ser
450                 455                 460
Phe Ala Asp Ile Leu Ser Gly Asp Trp Asn Thr Arg Ser Leu Leu Arg
465                 470                 475                 480
Glu Tyr Ser Thr Ser Ile Ala Thr Arg Gly Val Met His Ser Asn Lys
                485                 490                 495
Ala Arg Gly Tyr Ala His Cys Gln Gly Gly Gly Ser Ser Phe Arg Pro
```

```
                     -continued
         500                505                 510
Leu His Lys Pro Gln Trp Phe Leu Ile Asn Lys Lys Tyr Arg Glu Asn
        515                 520             525

Cys Leu Ala Ala Lys Ala Leu Phe Pro Asp Phe Cys Leu Pro Ala Leu
    530                 535             540

Cys Leu Gln Thr Gln Leu Leu Pro Tyr Leu Ala Leu Leu Thr Ile Pro
545             550                 555                     560

Met Arg Asn Gln Ala Gln Ile Ser Phe Ile Gln Asp Ile Gly Arg Leu
            565                 570                 575

Pro Leu Lys Arg His Phe Gly Arg Leu Lys Met Glu Ala Leu Thr Asp
            580                 585                 590

Arg Glu His Gly Met Ile Asp Pro Asp Ser Gly Asp Glu Ala Gln Leu
        595                 600                 605

Asn Gly Gly His Ser Ala Glu Glu Ser Leu Gly Glu Pro Thr Gln Ala
        610                 615                 620

Thr Val Pro Glu Thr Trp Ser Leu Pro Leu Ser Gln Asn Ser Ala Ser
625                 630                 635                 640

Glu Leu Pro Ala Ser Gln Pro Gln Pro Phe Ser Ala Gln Gly Asp Met
            645                 650                 655

Glu Glu Asn Ile Ile Ile Glu Asp Tyr Glu Ser Asp Gly Thr
            660                 665                 670
```

This protein has a molecular weight of between about 74 to 77 kDa, more preferably about 75.5 kDa. In the protein or polypeptide of SEQ. ID. No. 2, amino acids 126–133 conform to a highly conserved region known as the P-loop ATP/GTP binding consensus. Koonin, E. V., "A Common Set of Conserved Motifs in a Vast Variety of Putative Nucleic Acid-Dependent ATPases Including MCM Proteins Involved in the Initiation of Eukaryotic DNA Replication," *Nucleic Acids Res.*, 21:2541–47 (1993), which is incorporated herein by reference.

Another DNA molecule of the present invention, identified as human HRAD 1, comprises the nucleotide sequence corresponding to SEQ. ID. No. 3 as follows:

```
ATGCCCCTTC TGACCCAACA GATCCAAGAC GAGGATGATC AGTACAGCCT TGTGGCCAGC   60

CTTGACAACG TTAGGAATCT CTCCACTATC TTGAAAGCTA TTCATTTCCG AGAACATGCC  120

ACGTGTTTCG CAACTAAAAA TGGTATCAAA GTAACAGTGG AAAATGCAAA GTGTGTGCAA  180

GCAAATGCTT TTATTCAGGC TGGAATATTT CAGGAGTTTA AAGTTCAGGA AGAGTCTGTT  240

ACTTTTCGAA TTAATTTAAC TGTCCTTTTA GACTGTTTAT CTATTTTTGG ATCAAGTCCT  300

ATGCCAGGGA CTTTAACTGC ACTTCGAATG TGTTACCAAG GTTATGGTTA CCCTTTGATG  360

CTGTTCCTGG AAGAAGGAGG AGTGGTGACA GTCTGCAAAA TCAATACACA GGAACCTGAG  420

GAGACCCTGG ACTTTGATTT CTGCAGCACC AATGTTATTA ATAAAATTAT TCTGCAGTCA  480

GAGGGGCTCC GTGAAGCATT TTCTGAATTG GATATGACGA GTGAAGTCCT ACAAATTACC  540

ATGTCTCCTG ACAAGCCTTA TTTCAGGTTA TCTACTTTTG CAAATGCAGG AAGTTCCCAC  600

CTTGACTATC CCAAAGATTC TGATTTGATG GAAGCATTTC ATTGTAATCA GACCCAAGTC  660

AACAGATACA AGATTTCCTT ACTCAAACCC TCTACAAAGG CATTAGTCCT ATCTTGTAAG  720

GTATCTATTC GGACAGATAA CAGAGGCTTC CTTTCATTAC AGTATATGAT TAGAAATGAA  780

GATGGACAAA TATGTTTTGT GGAATATTAC TGCTGCCCTG ATGAAGAAGT TCCTGAATCT  840

GAGTCTTGA                                                          849
```

The DNA molecule of SEQ. ID. No. 3 encodes a protein or polypeptide identified as human Hrad1, which is believed to be involved in the single strand gap response pathway.

This protein or polypeptide has the deduced amino acid sequence corresponding to SEQ. ID. No. 4 as follows:

```
Met Pro Leu Leu Thr Gln Gln Ile Gln Asp Glu Asp Gln Tyr Ser
1               5                   10                  15
Leu Val Ala Ser Leu Asp Asn Val Arg Asn Leu Ser Thr Ile Leu Lys
            20                  25                  30
Ala Ile His Phe Arg Glu His Ala Thr Cys Phe Ala Thr Lys Asn Gly
            35                  40                  45
Ile Lys Val Thr Val Glu Asn Ala Lys Cys Val Gln Ala Asn Ala Phe
        50                  55                  60
Ile Gln Ala Gly Ile Phe Gln Glu Phe Lys Val Gln Glu Glu Ser Val
65                  70                  75                  80
Thr Phe Arg Ile Asn Leu Thr Val Leu Leu Asp Cys Leu Ser Ile Phe
                85                  90                  95
Gly Ser Ser Pro Met Pro Gly Thr Leu Thr Ala Leu Arg Met Cys Tyr
                100                 105                 110
Gln Gly Tyr Gly Tyr Pro Leu Met Leu Phe Leu Glu Glu Gly Gly Val
            115                 120                 125
Val Thr Val Cys Lys Ile Asn Thr Gln Glu Pro Glu Glu Thr Leu Asp
    130                 135                 140
Phe Asp Phe Cys Ser Thr Asn Val Ile Asn Lys Ile Ile Leu Gln Ser
145                 150                 155                 160
Glu Gly Leu Arg Glu Ala Phe Ser Glu Leu Asp Met Thr Ser Glu Val
                165                 170                 175
Leu Gln Ile Thr Met Ser Pro Asp Lys Pro Tyr Phe Arg Leu Ser Thr
                180                 185                 190
Phe Gly Asn Ala Gly Ser Ser His Leu Asp Tyr Pro Lys Asp Ser Asp
            195                 200                 205
Leu Met Glu Ala Phe His Cys Asn Gln Thr Gln Val Asn Arg Tyr Lys
        210                 215                 220
Ile Ser Leu Leu Lys Pro Ser Thr Lys Ala Leu Val Leu Ser Cys Lys
225                 230                 235                 240
Val Ser Ile Arg Thr Asp Asn Arg Gly Phe Leu Ser Leu Gln Tyr Met
                245                 250                 255
Ile Arg Asn Glu Asp Gly Gln Ile Cys Phe Val Glu Tyr Tyr Cys Cys
            260                 265                 270
Pro Asp Glu Glu Val Pro Glu Ser Glu Ser
            275                 280
```

This protein has a molecular weight of between about 30 to 34 kDa, more preferably about 31.8 kDa.

Another of the DNA molecules according to the present invention, identified as mouse HRAD1, comprises the nucleotide sequence corresponding to SEQ. ID. No. 5 as follows:

```
ATGCCTCTCC TAACCCAGTA CAATGAAGAG GAGTACGAAC AGTACTGCTT AGTGGCCAGC    60
CTTGACAACG TTAGGAATCT CTTCACTGTC TTGAAAGCCA TTCATTTCAG AGAACACGCC   120
ACGTGTTTTG CTACCAAAAA CGGAATCAAG GTTACAGTGG AGAATGCAAA GTGTGTGCAA   180
GCAAATGCCT TTATTCAGGC TGACGTGTTT CAGGAATTTG TCATTCAGGA AGAATCTGTT   240
ACTTTTCGAA TTAACTTAAC TATCCTTTTA GACTGTTTAT CTATTTTTGG ATCAAGTCCT   300
ACACCAGGGA CTTTGACTGC GCTTCGGATG TGTTACCAAG GTTATGGTCA CCCACTGATG   360
```

```
                                                           -continued
CTATTTCTAG AAGAAGGAGG AGTGGTGACG GTCTGCAAAA TTACCACTCA GGAGCCTGAG   420

GAGACACTGG ATTTTGATTT CTGCAGCACC AATGTTATGA ATAAAATTAT CCTGCAGTCA   480

GAGGGGCTCC GGGAAGCCTT TTCTGAGCTG GACATGACAG GTGATGTCCT ACAGATCACT   540

GTGTCTCCTG ACAAGCCCTA TTTCAGGTTG TCTACTTTTG GAAATGCAGG AAACTCCCAT   600

CTTGACTATC CCAAAGATTC CGACTTGGTG GAAGCCTTTC ACTGTGATAA GACCCAGGTC   660

AACAGATACA AGCTGTCGCT ACTGAAGCCC TCTACAAAGG CACTAGCTTT ATCCTGTAAA   720

GTGTCTATCC GGACAGATAA CCGAGGCTTC CTCTCCTTAC AGTACATGAT TAGAAATGAA   780

GATGGGCAGA TATGTTTTGT GGAATATTAC TGCTGCCCTG ATGAAGAAGT TCCTGAGTCT   840

TGA                                                                843
```

The DNA molecule having the nucleotide sequence of SEQ. ID. No. 5 encodes a protein or polypeptide identified as mouse Hrad1. It is believed that this protein or polypeptide is involved in the single strand gap response pathway and has the deduced amino acid sequence corresponding to SEQ. ID. No. 6 as follows:

```
Met Pro Leu Leu Thr Gln Tyr Asn Glu Glu Tyr Glu Gln Tyr Cys
1               5                   10                  15

Leu Val Ala Ser Leu Asp Asn Val Arg Asn Leu Phe Thr Val Leu Lys
            20                  25                  30

Ala Ile His Phe Arg Glu His Ala Thr Cys Phe Ala Thr Lys Asn Gly
            35                  40                  45

Ile Lys Val Thr Val Glu Asn Ala Lys Cys Val Gln Ala Asn Ala Phe
        50                  55                  60

Ile Gln Ala Asp Val Phe Gln Glu Phe Val Ile Gln Glu Ser Val
65                      70                  75

Thr Phe Arg Ile Asn Leu Thr Ile Leu Leu Asp Cys Leu Ser Ile Phe
                85                  90                  95

Gly Ser Ser Pro Thr Pro Gly Thr Leu Thr Ala Leu Arg Met Cys Tyr
                100                 105                 110

Gln Gly Tyr Gly His Pro Leu Met Leu Phe Leu Glu Glu Gly Gly Val
            115                 120                 125

Val Thr Val Cys Lys Ile Thr Thr Gln Glu Pro Glu Glu Thr Leu Asp
        130                 135                 140

Phe Asp Phe Cys Ser Thr Asn Val Met Asn Lys Ile Ile Leu Gln Ser
145                 150                 155                 160

Glu Gly Leu Arg Glu Ala Phe Ser Glu Leu Asp Met Thr Gly Asp Val
                165                 170                 175

Leu Gln Ile Thr Val Ser Pro Asp Lys Pro Tyr phe Arg Leu Ser Thr
            180                 185                 190

Phe Gly Asn Ala Gly Asn Ser His Leu Asp Tyr Pro Lys Asp Ser Asp
            195                 200                 205

Leu Val Glu Ala Phe His Cys Asp Lys Thr Gln Val Asn Arg Tyr Lys
        210                 215                 220

Leu Ser Leu Leu Lys Pro Ser Thr Lys Ala Leu Ala Leu Ser Cys Lys
225                 230                 235                 240

Val Ser Ile Arg Thr Asp Asn Arg Gly Phe Leu Ser Leu Gln Tyr Met
                245                 250                 255

Ile Arg Asn Glu Asp Gly Gln Ile Cys Phe Val Glu Tyr Tyr Cys Cys
            260                 265                 270

Pro Asp Glu Glu Val Pro Glu Ser
            275                 280
```

This protein has a molecular weight of between about 30 to 33 kDa, more preferably about 31.6 kDa.

The amino acid sequences of the polypeptides human Hrad1 (SEQ. ID. No. 4) and mouse Hrad1 (SEQ. ID. No. 6) contain a conserved motif, YxGxGxPxxxxxE, located between amino acids 112–124 of either of the polypeptides. Because of similarities between these polypeptides and another protein known to be involved in DNA repair mechanisms (Siede, W., et al., "Cloning and Characterization of RAD17, a Gene Controlling Cell Cycle Responses to DNA Damage in *Saccharomyces Cerevisiae*," *Nuc. Acids Res.*, 24:1669–75 (1996), which is incorporated herein by reference), it is believed that the human Hrad1 and mouse Hrad1 polypeptides also are involved with DNA repair mechanisms.

Another DNA molecule of the present invention, identified as human HHUS1, comprises the nucleotide sequence corresponding to SEQ. ID. No. 7 as follows:

```
ATGAAGTTTC GGGCCAAGAT CGTGGACGGG GCCTGTCTGA ACCACTTCAC ACGAATCAGT   60
AACATGATAG CCAAGCTTGC CAAAACCTGC ACCCTCCGCA TCAGCCCTGA TAAGCTTAAC  120
TTCATCCTTT GTGACAAGCT GGCTAATGGA GGAGTGAGCA TGTGGTGTGA GCTGGAACAG  180
GAGAACTTCT TCAACGAATT TCAAATGGAG GGTGTCTCTG CAGAAAACAA TGAGATTTAT  240
TTAGAGCTAA CATCGGAAAA CTTATCTCGA GCCTTGAAGA CTGCCCAGAA TGCCAGGGCT  300
TTGAAAATCA AACTGACTAA TAAACACTTT CCCTGCCTCA CGGTCTCCGT GGAGCTGTTA  360
TCTATGTCAA GCAGTAGCCG CATTGTGACC CATGACATCC CCATAAAGGT GATTCCTAGG  420
AAATTGTGGA AGGACTTACA AGAACCGGTG GTCCCAGATC CTGATGTTAG TATTTATTTA  480
CCAGTCTTGA AGACTATGAA GAGTGTTGTG GAAAAAATGA AAAACATCAG CAATCACCTT  540
GTTATTGAAG CAAACCTAGA TGGAGAATTG AATTTGAAAA TAGAAACTGA ATTAGTATGT  600
GTTACAACTC ATTTTAAAGA TCTTGGAAAT CCTCCATTAG CCTCTGAAAG CACCCATGAG  660
GACAGAAACG TGGAACACAT GGCTGAAGTG CACATAGATA TTAGGAAGCT CCTACAGTTT  720
CTTGCTGGAC AACAAGTAAA TCCCACAAAG GCCTTATGCA ATATTGTGAA TAACAAGATG  780
GTGCATTTTG ATCTGCTTCA TGAAGACGTG TCCCTTCAGT ATTTCATCCC TGCGCTGTCC  840
TAG                                                                843
```

The DNA molecule having the nucleotide sequence of SEQ. ID. No. 7 encodes a protein or polypeptide identified as human Hhus1. It is believed that this protein or polypeptide is involved in the single strand gap response pathway and has the deduced amino acid sequence corresponding to SEQ. ID. No. 8 as follows:

```
Met Lys Phe Arg Ala Lys Ile Val Asp Gly Ala Cys Leu Asn His Phe
 1               5                  10                  15

Thr Arg Ile Ser Asn Met Ile Ala Lys Leu Ala Lys Thr Cys Thr Leu
                20                  25                  30

Arg Ile Ser Pro Asp Lys Leu Asn Phe Ile Leu Cys Asp Lys Leu Ala
                35                  40                  45

Asn Gly Gly Val Ser Met Trp Cys Glu Leu Glu Gln Glu Asn Phe Phe
            50                  55                  60

Asn Glu Phe Gln Met Glu Gly Val Ser Ala Glu Asn Asn Glu Ile Tyr
65                  70                  75                  80

Leu Glu Leu Thr Ser Glu Asn Leu Ser Arg Ala Leu Lys Thr Ala Gln
                85                  90                  95

Asn Ala Arg Ala Leu Lys Ile Lys Leu Thr Asn Lys His Phe Pro Cys
                100                 105                 110

Leu Thr Val Ser Val Glu Leu Leu Ser Met Ser Ser Ser Ser Arg Ile
                115                 120                 125

Val Thr His Asp Ile Pro Ile Lys Val Ile Pro Arg Lys Leu Trp Lys
                130                 135                 140

Asp Leu Gln Glu Pro Val Val Pro Asp Pro Asp Val Ser Ile Tyr Leu
145                 150                 155                 160
```

```
                        -continued
Pro Val Leu Lys Thr Met Lys Ser Val Val Glu Lys Met Lys Asn Ile
                165             170             175

Ser Asn His Leu Val Ile Glu Ala Asn Leu Asp Gly Glu Leu Asn Leu
                180             185             190

Lys Ile Glu Thr Glu Leu Val Cys Val Thr Thr His Phe Lys Asp Leu
            195             200             205

Gly Asn Pro Pro Leu Ala Ser Glu Ser Thr His Glu Asp Arg Asn Val
        210             215             220

Glu His Met Ala Glu Val His Ile Asp Ile Arg Lys Leu Leu Gln Phe
225             230             235             240

Leu Ala Gly Gln Gln Val Asn Pro Thr Lys Ala Leu Cys Asn Ile Val
                245             250             255

Asn Asn Lys Met Val His Phe Asp Leu Leu His Glu Asp Val Ser Leu
                260             265             270

Gln Tyr Phe Ile Pro Ala Leu Ser
            275             280
```

The molecular weight of this protein or polypeptide is between about 30 to 33 kDa, more preferably about 31.7 kDa.

Yet another isolated DNA molecule according to the present invention, identified as mouse HHUS1, comprises the nucleotide sequence corresponding to SEQ. ID. No. 9 as follows:

```
ATGAAGTTTC GCGCCAAGAT CGTGGACCTG GCTTGTCTGA ATCATTTCAC ACGAGTCAGT    60

AACATGATAG CCAAGCTTGC CAAAACCTGC ACCCTCCGCA TCAGCCCGGA GAAGCTGAAC   120

TTCATCCTGT GCGACAAGCT GGCCAGTGGA GGCGTGAGCA TGTGGTGTGA GCTGGAGCAG   180

GAGAACTTTT TTAGTGAATT TCAAATGGAA GGAGTCTCTG AAGAAAACAA CGAGATTTAT   240

TTAGAATTAA CGTCGGAAAA CTTATCTCGA GCCTTGAAAA CTGCCCAGAA CTCCAGAGCC   300

TTGAAAATCA AGCTGACTAA CAAACACTTT CCCTGTCTTA CCGTGTCTGT AGAGCTGCAG   360

GTGTCTTCAT CGAGCAGCAG CAGAATCGTG GTGCATGATA TCCCCATAAA GGTTCTTCCG   420

AGAAGACTGT GGAAGGACTT ACAAGAACCC TCCATCCCAG ACTGTGATGT CAGTATTTGC   480

TTACCAGCCT TGAAGATGAT GAAGAGTGTT GTGGAAAAAA TGAGAAACAT CAGCAATCAG   540

CTTGTGATTG AAGCAAACCT AAAGGGAGAA TTAAACCTAA AGATAGAAAC TGAGTTAGTG   600

TGTGTGACTA CTCATTTTAA GGATCTTGAA AACCCTCTAT TACCCTCTGA CAGTGTCTCT   660

CAAAACAGAC ACCCAGAAGA CATGGCCAAG GTGCACATTG ACATAAAGAA ACTCCTCCAG   720

TTTCTTGCCG GACAGCAAGT GACTCCCACC AAGGCAGTGT GCAATATTGT GAATAACAGA   780

ACTGTTCATT TTGATTTGCT CCTGGAAGAC GTCTCCCTTC AGTATTTCAT CCCAGCCTTG   840

TCCTAG                                                              846
```

The DNA molecule having the nucleotide sequences of SEQ. ID. No. 9 encodes for a protein or polypeptide identified as mouse Hhus1. It is believed that this protein or polypeptide is involved in the single strand gap response pathway and has the deduced amino acid sequence corresponding to SEQ. ID. No. 10 as follows:

```
Met Lys Phe Arg Ala Lys Ile Val Asp Leu Ala Cys Leu Asn His Phe
1               5               10              15

Thr Arg Val Ser Asn Met Ile Ala Lys Leu Ala Lys Thr Cys Thr Leu
                20              25              30
```

-continued

```
Arg Ile Ser Pro Glu Lys Leu Asn Phe Ile Leu Cys Asp Lys Leu Ala
        35                  40                  45

Ser Gly Gly Val Ser Met Trp Cys Glu Leu Glu Gln Glu Asn Phe Phe
    50                  55                  60

Ser Glu Phe Gln Met Glu Gly Val Ser Glu Glu Asn Asn Glu Ile Tyr
65                  70                  75                  80

Leu Glu Leu Thr Ser Glu Asn Leu Ser Arg Ala Leu Lys Thr Ala Gln
                85                  90                  95

Asn Ser Arg Ala Leu Lys Ile Lys Leu Thr Asn Lys His Phe Pro Cys
            100                 105                 110

Leu Thr Val Ser Val Glu Leu Gln Val Ser Ser Ser Ser Ser Ser Arg
            115                 120                 125

Ile Val Val His Asp Ile Pro Ile Lys Val Leu Pro Arg Arg Leu Trp
        130                 135                 140

Lys Asp Leu Gln Glu Pro Ser Ile Pro Asp Cys Asp Val Ser Ile Cys
145                 150                 155                 160

Leu Pro Ala Leu Lys Met Met Lys Ser Val Val Glu Lys Met Arg Asn
                165                 170                 175

Ile Ser Asn Gln Leu Val Ile Glu Ala Asn Leu Lys Gly Glu Leu Asn
            180                 185                 190

Leu Lys Ile Glu Thr Glu Leu Val Cys Val Thr Thr His Phe Lys Asp
        195                 200                 205

Leu Glu Asn Pro Leu Leu Pro Ser Asp Ser Val Ser Gln Asn Arg His
    210                 215                 220

Pro Glu Asp Met Ala Lys Val His Ile Asp Ile Lys Lys Leu Leu Gln
225                 230                 235                 240

Phe Leu Ala Gly Gln Gln Val Thr Pro Thr Lys Ala Val Cys Asn Ile
                245                 250                 255

Val Asn Asn Arg Thr Val His Phe Asp Leu Leu Leu Glu Asp Val Ser
            260                 265                 270

Leu Gln Tyr Phe Ile Pro Ala Leu Ser
        275                 280
```

This protein or polypeptide has a molecular weight of between about 30 to 33 kDa, more preferably about 31.6 kDa.

The present invention also relates to SSGR proteins and DNA molecules encoding such proteins from non-mammalian hosts (e.g., *Drosophila melanogaster* and *Caenorhabditis elegans*). In this regard, one example of such an isolated DNA molecule, identified as *Drosophila melanogaster* HRAD17, comprises the nucleotide sequence corresponding to SEQ. ID. No.11 as follows:

```
ATGAACTTGA CCACCAGTCC TGCTCCTTCG GAATCCACGC TGCGAAGCG CACAAGAAGT    60

GCAAGCAATG TGAGCAGCTC CAGAGTATCG AGGTCGAGAA CTCCAAGCAT AAATACAAAG   120

CCAATACAGA TTCCGGACGT GGACTCAGTC GATCTTACTG CCATGGATGA TGACCAGGAT   180

GCGGACATCA CTGTGCCACC GCCAGAAGTC AAAGAAAACT GGATGGAAAG CTTTGAGCCA   240

GCCACCAGCG ACGATTTGGC GGTGCATCCA AAGAAGGTCG GAGAACTACG CGATTGGCTG   300

CGTCACTGCG AAGCGGTGCG CAAGAAGTTC CCGGCTCAAA TGTGTCTACT TACCGGGCCC   360

ACTGGTGCTG GCAAAACCAC CACGTTGCGA GTCCTGGCCA AGGAGTTCGG CTACCAGCTG   420

CAGGAGTGGA TCAATCCTAT CGATTGTGAG GTGGTCAACA CCTTGGGTGA TCAAACGACT   480

GGCGCCTCCT ATGTGGGCTC CCATCTGGAG GCCTTTAAAA GCTTTCTGCT CCGTGCCTCG   540

CGATACAAAT CCTTGCTGGA CTCGCAAAAT AAGAGACTGC TTCTTGTCGA GGACTTTCCC   600

AACGTCCTGC TCAGCGATAA GGAGGTCAAC TTTGAAGAGT TACTAGAAGA GTACACGGCG   660
```

```
TATGGCAAAT CTCCCCTGGT GTTCATCGTT GCCGATGCCA AATCTCGAGG ATTGAATATC   720

AGCTACCGCC TCTTTCCAGA CCAACTGAAG GCCAAACATC GCATCGAGCA CATCAGTTTC   780

AATGCTATTG CATCTACAAT CATGCAAAAG TCAATGAAAA CCTTCTGCTC CGTAATGCAG   840

CAGAATAAAG CTACTTACAA GGTGCCCTCG ACCGCTGTTG TTGACTCAAT AGTTGTCGGT   900

GCCCAGGGCG ACATAAGAAA TGCGTTAATT AATTTACATT TGAGCTCTTT AAAGGGAGTT   960

TCCAGCATGC CGACCAAACA GCTAAATGTC AGTGTGTCCG CAAAAGGTCG TAAGAAGAAA  1020

ATGCAAAGTA CTTTAAAGTC AATTGGTAGA GATGAATCAA TTACTCTGAT GCACGCACTT  1080

GGAAGAGTAT TAAATCCTAA GTTTAATGAG GACAAAACTA TGTTACACAG CCCGGAGGAA  1140

ATAACCGAAG CCTTTAATAC AGAGCCCAGG AATTTTGTGA ATTTTGTATA TGCCAACTAT  1200

CTGCCGCATT TTAAGGAAAT CGATGATGTC GTGACCGCCA TAAATGACTT GGGCCTATCA  1260

GATTGCATGC TCAACGAGTA CAGAGATGAT AATTTGTCTG TGATGGGCTT AAACGTTGCC  1320

ATACGAGGAG TTATGATGTC CAATACGTGC CCTGTCAGCG GATGGATGCC TGTTCGAGGA  1380

CCCAAGCGAA TCAATATACA GCCACAGGCA ACTTTGGCCG AACAAAGACT GGTGGGTGTG  1440

GGCTACGCGG GCATTGCCAG GACGCTCTAC GCCACGGAGT ACAGCTCATT AGTTAAGTTA  1500

ATAGCAGGCA AGCCTGTGGA TACTACTTCA AGCCAAAGCA CAGACTCAAA ACAAGACTTT  1560

TAG                                                                1563
```

The DNA molecule having the nucleotide sequences of SEQ. ID. No. 11 encodes for a protein or polypeptide identified as *Drosophila melanogaster* Hrad17. It is believed that this protein or polypeptide is involved in the single strand gap response pathway and has the deduced amino acid sequence corresponding to SEQ. ID. No. 12 as follows:

```
Met Asn Leu Thr Thr Ser Pro Ala Pro Ser Glu Ser Thr Pro Ala Lys
1               5                   10                  15

Arg Thr Arg Ser Ala Ser Asn Val Ser Ser Ser Arg Val Ser Arg Ser
            20                  25                  30

Arg Thr Pro Ser Ile Asn Thr Lys Pro Ile Gln Ile Pro Asp Val Asp
            35                  40                  45

Ser Val Asp Leu Thr Ala Met Asp Asp Gln Asp Ala Asp Ile Thr
        50                  55                  60

Val Pro Pro Pro Glu Val Lys Glu Asn Trp Met Glu Ser Phe Glu Pro
65                  70                  75                  80

Ala Thr Ser Asp Asp Leu Ala Val His Pro Lys Lys Val Gly Glu Leu
                85                  90                  95

Arg Asp Trp Leu Arg His Cys Glu Ala Val Arg Lys Lys Phe Pro Ala
                100                 105                 110

Gln Met Cys Leu Leu Thr Gly Pro Thr Gly Ala Gly Lys Thr Thr Thr
                115                 120                 125

Leu Arg Val Leu Ala Lys Glu Phe Gly Tyr Gln Leu Gln Glu Trp Ile
    130                 135                 140

Asn Pro Ile Asp Cys Glu Val Val Asn Thr Leu Gly Asp Gln Thr Thr
145                 150                 155                 160

Gly Ala Ser Tyr Val Gly Ser His Leu Glu Ala Phe Lys Ser Phe Leu
                165                 170                 175

Leu Arg Ala Ser Arg Tyr Lys Ser Leu Leu Asp Ser Gln Asn Lys Arg
                180                 185                 190

Leu Leu Leu Val Glu Asp Phe Pro Asn Val Leu Leu Ser Asp Lys Glu
                195                 200                 205
```

-continued

```
Val Asn Phe Glu Glu Leu Leu Glu Glu Tyr Thr Ala Tyr Gly Lys Ser
    210                 215                 220

Pro Leu Val Phe Ile Val Ala Asp Ala Lys Ser Arg Gly Leu Asn Ile
225                 230                 235                 240

Ser Tyr Arg Leu Phe Pro Asp Gln Leu Lys Ala Lys His Arg Ile Glu
            245                 250                 255

His Ile Ser Phe Asn Ala Ile Ala Ser Thr Ile Met Gln Lys Ser Met
                260                 265                 270

Lys Thr Phe Cys Ser Val Met Gln Gln Asn Lys Ala Thr Tyr Lys Val
            275                 280                 285

Pro Ser Thr Ala Val Val Asp Ser Ile Val Val Gly Ala Gln Gly Asp
    290                 295                 300

Ile Arg Asn Ala Leu Ile Asn Leu His Leu Ser Ser Leu Lys Gly Val
305                 310                 315                 320

Ser Ser Met Pro Thr Lys Gln Leu Asn Val Ser Val Ser Ala Lys Gly
                325                 330                 335

Arg Lys Lys Lys Met Gln Ser Thr Leu Lys Ser Ile Gly Arg Asp Glu
            340                 345                 350

Ser Ile Thr Leu Met His Ala Leu Gly Arg Val Leu Asn Pro Lys Phe
    355                 360                 365

Asn Glu Asp Lys Thr Met Leu His Ser Pro Glu Glu Ile Thr Glu Ala
370                 375                 380

Phe Asn Thr Glu Pro Arg Asn Phe Val Asn Phe Val Tyr Ala Asn Tyr
385                 390                 395                 400

Leu Pro His Phe Lys Glu Ile Asp Asp Val Val Thr Ala Ile Asn Asp
                405                 410                 415

Leu Gly Leu Ser Asp Cys Met Leu Asn Glu Tyr Arg Asp Asp Asn Leu
            420                 425                 430

Ser Val Met Gly Leu Asn Val Ala Ile Arg Gly Val Met Met ser Asn
    435                 440                 445

Thr Cys Pro Val Ser Gly Trp Met Pro Val Arg Gly Pro Lys Arg Ile
    450                 455                 460

Asn Ile Gln Pro Gln Ala Thr Leu Ala Glu Gln Arg Leu Val Gly Val
465                 470                 475                 480

Gly Tyr Ala Gly Ile Ala Arg Thr Leu Tyr Ala Thr Glu Tyr Ser Ser
                485                 490                 495

Leu Val Lys Leu Ile Ala Gly Lys Pro Val Asp Thr Thr Ser Ser Gln
            500                 505                 510

Ser Thr Asp Ser Lys Gln Asp Phe
    515                 520
```

This protein or polypeptide has a molecular weight of between about 56 to 59 kDa, more preferably about 57.6 kDa.

Another isolated DNA molecule according to the present invention, identified as *Caenorhabditis elegans* HRAD17, comprises the nucleotide sequence corresponding to SEQ. ID. No. 13 as follows:

```
ATGAAAGCCG CTGAACACGA TTTGCTCACA ATTGAGCTTG CTCCACGGCG ACGAGATGAG    60
CTCCAAATCC ACAATAAAAA GATTGCAGAG GTCGATCATT GGCTCAAAAA TGTATTTTCT   120
GAGTCAAACA AGCAGCTAGG AGTGATGTAC CTCACACGAC CAGCTGGCTC GGGCAAATCG   180
ACGACTGTCG AAGTGATGTG CACAGAGCAG AATATCCAAA TCATCGAATA TTCGCCAGAA   240
TATCTTCACA ATGAAGATTT CGAGTGTGAA AAGCCGCATT TCACCCAGCT GCGGAGGTTT   300
TTGTTGCGGA GACATGGAAG CTTGCGGGGT GGTGGCTTGA AAAAGCGGCT TCTTCTCGTC   360
```

```
ACAGAGCTGC CTGATCAAGC TTATAGTGAT GCTGAGAAGT TTCGAGAAGA TTTGTCAGAA   420
GTTCTGCAAC ATATTTGGCA TCCCGTGATA TTCTGCCTCA CGAATAGTAT TGCATGCTGG   480
AATTTGAACC CTGATCGATT GTTTACCAAG GACTTTAACA TTATGAATGG AATAGATACA   540
GTAACATTCA ACCCAGTTGC TGACTCCTTC ATGAAAAAAG CACTCGTCCG CGCTTCAAAC   600
TGCCTGAGCT CCCCACTATC CGATGCAAAG CTGAATGTGA TCGGAGAGGA AGCTGGAGGC   660
GATTTGAGAA TCGCTATGAA TATGTTACAG ATGAATTCGA TTGGACCGAA TGCTGATAGA   720
AGAAGTGGAA ATAGTGTGAT ATGTGCATCG AAAGCGAATC GAGAAGAAGC TTTTCATATG   780
ATTGGGCGAA TTTTATACGC GAAACGTGTC AATCCGAATG TTCCGAAGCC GAGTCGTTTC   840
TCGAAGCGAA GGCGGAAGTC TGCACCGATT CCGGAGCCGC TAGTGAGAAC AGAGCTGGAG   900
CATGACCCGA CTGATATTAT TACAATGTCG AGTATGACTT CTGAGAAGCT TCTCGACTTT   960
CTATTTCAAA ATGAGCCCAT CTTCTGCTCG AATATATCCA AATATCGCTA CGTCGCGGAG  1020
ACTTTTTCGA TGTGTGACTT TTTAACCGGA GACTGGACGA CCCGAAAATC TCTGCCAGAA  1080
GATTACGTGG CACAGATGGC TACACGTTCG GTGATGTCGA ATAACTACAA AGAACCTCGC  1140
CCGGGAACAT TATTCGCAGT CGGACGTCCG TTAAGAAGCT CACTGGAAAA ACACACGGCT  1200
CGAACGAAAT TGGAATTGCA AAGACTTCCG ATGATTGCTG CCAAGGATTA TGCTGCTCTA  1260
ACATGTCCGT ATATAACAAT CATCAAGGAT ATTATCGATC CGCAGAGAAT CGAGTATTTC  1320
CTCTCGAGAC CCATGGATAT CAACTGGCAA TGGGGAAATG ATAAAATCGA GGAGCATTTA  1380
GAGAAACAGT ATGCCCTAGA CTACAAAGGA CGTAAAAAAC ACCGTCTTCC CCTTCATAAG  1440
GCACCGAAGC CTTCCGGAAA GATTATCGAA GTGGTGGATT TGGAAGAGGA AGAGGAAAAG  1500
TTCACAATCG AGGAGTCCAG TGACGATTCT TTTGAAGAAT TTTGA              1545
```

The DNA molecule having the nucleotide sequences of SEQ. ID. No. 13 encodes for a protein or polypeptide identified as *Caenorhabditis elegans* Hrad17. It is believed that this protein or polypeptide is involved in the single strand gap response pathway and has the deduced amino acid sequence corresponding to SEQ. ID. No. 14 as follows:

```
Met Lys Ala Ala Glu His Asp Leu Leu Thr Ile Glu Leu Ala Pro Arg
1               5                   10                  15

Arg Arg Asp Glu Leu Gln Ile His Asn Lys Lys Ile Ala Glu Val Asp
                20                  25                  30

His Trp Leu Lys Asn Val Phe Ser Glu Ser Asn Lys Gln Leu Gly Val
            35                  40                  45

Met Tyr Leu Thr Gly Pro Ala Gly Ser Gly Lys Ser Thr Thr Val Glu
        50                  55                  60

Val Met Cys Thr Glu Gln Asn Ile Glu Ile Ile Glu Tyr Ser Pro Glu
65                  70                  75                  80

Tyr Leu His Asn Glu Asp Phe Glu Cys Glu Lys Pro Asp Phe Thr Gln
                85                  90                  95

Leu Arg Arg Phe Leu Leu Arg Arg His Gly Ser Leu Arg Gly Gly Gly
            100                 105                 110

Leu Lys Lys Arg Leu Leu Leu Val Thr Glu Leu Pro Asp Gln Ala Tyr
        115                 120                 125

Ser Asp Ala Glu Lys Phe Arg Glu Asp Leu Ser Glu Val Leu Gln His
    130                 135                 140

Ile Trp His Pro Val Ile Phe Cys Leu Thr Asn Ser Ile Ala Cys Trp
145                 150                 155                 160

Asn Leu Asn Pro Asp Arg Leu Phe Thr Lys Asp Phe Asn Ile Met Asn
```

-continued

```
                    165                 170                 175
Gly Ile Asp Thr Val Thr Phe Asn Pro Val Ala Asp Ser Phe Met Lys
                180                 185                 190
Lys Ala Leu Val Arg Ala Ser Asn Cys Leu Ser Ser Pro Leu Ser Asp
            195                 200                 205
Ala Lys Leu Asn Val Ile Gly Glu Glu Ala Gly Gly Asp Leu Arg Ile
        210                 215                 220
Ala Met Asn Met Leu Gln Met Asn Ser Ile Gly Pro Asn Ala Asp Arg
225                 230                 235                 240
Arg Ser Gly Asn Ser Val Ile Cys Ala Ser Lys Ala Asn Arg Glu Glu
                245                 250                 255
Ala Phe His Met Ile Gly Arg Ile Leu Tyr Ala Lys Arg Val Asn Pro
                260                 265                 270
Asn Val Pro Lys Pro Ser Arg Phe Ser Lys Arg Arg Arg Lys Ser Ala
            275                 280                 285
Pro Ile Pro Glu Pro Leu Val Arg Thr Glu Leu Glu His Asp Pro Thr
        290                 295                 300
Asp Ile Ile Thr Met Ser Ser Met Thr Ser Glu Lys Leu Leu Asp Phe
305                 310                 315                 320
Leu Phe Gln Asn Glu Pro Ile Phe Cys Ser Asn Ile Ser Lys Tyr Arg
                325                 330                 335
Tyr Val Ala Glu Thr Phe Ser Met Cys Asp Phe Leu Thr Gly Asp Trp
                340                 345                 350
Thr Thr Arg Lys Ser Leu Pro Glu Asp Tyr Val Ala Gln Met Ala Thr
            355                 360                 365
Arg Ser Val Met Trp Asn Asn Tyr Lys Glu Pro Arg Pro Gly Thr Leu
        370                 375                 380
Phe Ala Val Gly Arg Pro Leu Arg Ser Ser Leu Glu Lys His Thr Ala
385                 390                 395                 400
Arg Thr Lys Leu Glu Leu Gln Arg Leu Pro Met Ile Gly Ala Lys Asp
                405                 410                 415
Tyr Ala Ala Leu Thr Cys Pro Tyr Ile Thr Ile Ile Lys Asp Ile Ile
                420                 425                 430
Asp Pro Gln Arg Ile Glu Tyr Phe Leu Ser Arg Pro Met Asp Ile Asn
            435                 440                 445
Trp Gln Trp Gly Asn Asp Lys Ile Glu Glu His Leu Glu Lys Gln Tyr
        450                 455                 460
Ala Leu Asp Tyr Lys Gly Arg Lys Lys Arg His Arg Leu Pro Leu His Lys
465                 470                 475                 480
Ala Pro Lys Pro Ser Gly Lys Ile Ile Glu Val Val Asp Leu Glu Glu
            485                 490                 495
Glu Glu Glu Lys Phe Thr Ile Glu Glu Ser Ser Asp Asp Ser Phe Glu
                500                 505                 510
Glu Phe
```

This protein or polypeptide has a molecular weight of between about 57 to 61 kDa, more preferably about 59.1 kDa.

Still another isolated DNA molecule according to the present invention, identified as *Caenorhabditis elegans* HRAD1, comprises the nucleotide sequence corresponding to SEQ. ID. No. 15 as follows:

```
ATGATGGAAT TAGAAACGGG TCAATGCACA ATTATGGAAT TGAAAAAAGA AAATGTGAAG    60
GAGCTCGCGC AGGTCTTCAA AACCGTCGCT TTTAAGGATA CAGGAACGTG GCACGCTTCC   120
```

```
                    -continued
GAGGCGGGCA TGAAGATCAC AGTCGACGAT GGATCCTATC AGCTGGCCAG CGTTTTTATC    180

AATCCGGCGT TCTTCTCGAG TTTTAAAGTT CGCGAGGAGA TAGTTTCGAT GAAAATCTCG    240

ATTAAATCGA TTTCTGAATT CCTGAGCATT TCGGAAAACT CGTCGAGTTC TGTAAAAGTC    300

TCGTATCCGG GAATGTTTCA GCCTGTGAAA ATGCTTGTTG AAGACGCAGA CGGATGGGTG    360

GCACGTGGCA ATTTTACAAC AACGCTGGCA GATCAAGAGC TCGACTTTGA ATTCGATGAC    420

GCTGGTGTGC TGGCGACCTA TCTGCTTAAA ACTCAAGTTC TCAAGGAGAT TATCAAGGAC    480

TTCGATGACA CAAGCCGAAC GGTGAGAATT CAATTCACCA AGAATTCACT GTGTTTCACG    540

ACTTTCGGTG ATGTTGGCGA GACTACAGTA TCAATACCGT CTCGAAGCCT TCAAATGGAA    600

AGTGTAAAGT GCCTTGAAGA AGTTGAATTT AGCTATCTTC TGTCGCTTAT TCAACGAATG    660

ACTACCGCCT TTATACTGGC TACAAAGCTC ATCCTCCGTG TCGACGAGCG TGGCGTCCTC    720

TCCTGTCAAT TTTCAATCGA TCACGGCGAG GGAAACGCAA GCTACATTGA ATTTCTGACG    780

GTGCCCGCTG ATGAAGAAGA ATAA                                          804
```

The DNA molecule having the nucleotide sequences of SEQ. ID. No. 15 encodes for a protein or polypeptide identified as *Caenorhabditis elegans* Hrad1. It is believed that this protein or polypeptide is involved in the single strand gap response pathway and has the deduced amino acid sequence corresponding to SEQ. ID. No. 16 as follows:

```
Met Met Glu Leu Glu Thr Gly Gln Cys Thr Ile Met Glu Leu Lys Lys
1               5                   10                  15

Glu Asn Val Lys Glu Leu Ala Gln Val Phe Lys Thr Val Ala Phe Lys
                20                  25                  30

Asp Thr Gly Thr Trp His Ala Ser Glu Ala Gly Met Lys Ile Thr Val
            35                  40                  45

Asp Asp Gly Ser Tyr Gln Leu Ala Ser Val Phe Ile Asn Pro Ala Phe
        50                  55                  60

Phe Ser Ser Phe Lys Val Arg Glu Glu Ile Val Ser Met Lys Ile Ser
65                  70                  75                  80

Ile Lys Ser Ile Ser Glu Phe Leu Ser Ile Ser Glu Asn Ser Ser Ser
                85                  90                  95

Ser Val Lys Val Ser Tyr Pro Gly Met Phe Gln Pro Val Lys Met Leu
                100                 105                 110

Val Glu Asp Ala Asp Gly Trp Val Ala Arg Gly Asn Phe Thr Thr Thr
            115                 120                 125

Leu Ala Asp Gln Glu Leu Asp Phe Glu Phe Asp Asp Ala Gly Val Leu
        130                 135                 140

Ala Thr Tyr Leu Leu Lys Thr Gln Val Leu Lys Glu Ile Ile Lys Asp
145                 150                 155                 160

Phe Asp Asp Thr Ser Arg Thr Val Arg Ile Gln Phe Thr Lys Asn Ser
                165                 170                 175

Leu Cys Phe Thr Thr Phe Gly Asp Val Gly Glu Thr Thr Val Ser Ile
                180                 185                 190

Pro Ser Arg Ser Leu Gln Met Glu Ser Val Lys Cys Leu Glu Glu Val
            195                 200                 205

Glu Phe Ser Tyr Leu Leu Ser Leu Ile Gln Arg Met Thr Thr Ala Phe
            210                 215                 220

Ile Leu Ala Thr Lys Leu Ile Leu Arg Val Asp Glu Arg Gly Val Leu
225                 230                 235                 240
```

```
                         -continued
Ser Cys Gln Phe Ser Ile Asp His Gly Glu Gly Asn Ala Ser Tyr Ile
                245                 250                 255

Glu Phe Leu Thr Val Pro Ala Asp Glu Glu Glu
            260                 265
```

This protein or polypeptide has a molecular weight of between about 28 to 32 kDa, more preferably about 29.9 kDa.

Also encompassed by the present invention are fragments of the above DNA molecules and the proteins or polypeptides they encode. Suitable fragments are constructed by using appropriate restriction sites, revealed by inspection of the DNA molecule's sequence, to: (i) insert an interposon (Felly, et al., "Interposon Mutagenesis of Soil and Water Bacteria: A Family of DNA Fragments Designed for in vitro Insertion Mutagenesis of Gram-negative Bacteria," *Gene* 52:147–15 (1987), which is hereby incorporated by reference) such that truncated forms of the polypeptides or proteins of the present invention, that lack various amounts of the C-terminus, can be produced or (ii) delete various internal portions of the protein.

Variants may also (or alternatively) be made by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

In addition, it may be advantageous to modify the peptides in order to impose a conformational restraint upon them. This might be useful, for example, to mimic a naturally-occurring conformation of the peptide in the context of the native protein in order to optimize the effector immune responses that are elicited.

Modified peptides are referred to herein as "peptide analogs". The term "peptide analog" extends to any functional chemical equivalent of a peptide characterized by its increased stability and/or efficacy and immunogenicity in vivo or in vitro in respect of the practice of the invention. Peptide analogs contemplated herein are produced by procedures that include, but are not limited to, modifications to side chains, incorporation of unnatural amino acids and/or their derivatives during peptide synthesis and the use of cross-linkers and other methods which impose conformational constraint on the peptides or their analogs.

It will be apparent that the peptides employed herein as antigens can be modified in a variety of different ways without significantly affecting the functionally important immunogenic behavior thereof. Possible modifications to the peptide sequence may include the following:

One or more individual amino acids can be substituted by amino acids having comparable or similar properties, thus:

V may be substituted by I;

T may be substituted by S;

K may be substituted by R; or

L may be substituted by I, V, or M.

One or more of the amino acids of the peptides of the invention can be replaced by a "retro-inverso" amino acid, i.e., a bifunctional amine having a functional group corresponding to an amino acid, as discussed in published International application WO 91/13909, which is hereby incorporated by reference.

One or more amino acids can be deleted.

Structural analogs mimicking the 3-dimensional structure of the peptide can be used in place of the peptide.

Examples of side chain modifications contemplated by the present invention include modification of amino groups, such as by reductive alkylation by reaction with an aldehyde followed by reduction with NaBH; amidation with methylacetimidate; acetylation with acetic anhydride; carbamylation of amino groups with 2, 4, 6, trinitrobenzene sulfonic acid (TNBS); alkylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents, such as 2,3-butanedione, phenylglyoxal and glyoxal.

The carboxyl group may be modified by carbodiimide activation via o-acylisourea formation followed by subsequent derivatisation, for example, to a corresponding amide.

Sulfhydryl groups may be modified by methods, such as carboxymethylation with iodoacetic acid or iodoacetamide; performic acid oxidation to cysteic acid; formation of sulfides and disulfides with other thiol compounds; reaction with maleimide, maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; and carbamylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tyrosine residues may be altered by nitration with tetranitromethane for form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Further, the peptides of the present invention may be lipidated with, for example, cholesterol or palmitate to incorporate it into cationic liposomes.

Any one of the DNA molecules of the present invention can be incorporated in cells using conventional recombinant DNA technology. Generally, this involves inserting the selected DNA molecule into an expression system to which that DNA molecule is heterologous (i.e. not normally present). The heterologous DNA molecule is inserted into the expression system or vector in proper orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eukaryotic cells grown in tissue culture.

Recombinant genes may also be introduced into viruses, such as vaccina virus. Recombinant viruses can be generated by transfection of plasmids into cells infected with virus.

Suitable expression vectors include plasmids, bacteriophage virus, retroviruses or other modified virus. Examples of suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference), pQE, pIH821, pGEX, pET series (Studier, F. W., et. al., "Use of T7 RNA Polymerase to Direct Expression of Cloned Genes," *Gene Expression Technology* vol. 185 (1990), which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Spring Laboratory, Cold Spring Harbor Laboratory Press, New York (1982); and Sambrook et al., *Molecular Cloning: A Laboratory Manual*, Cold Spring Laboratory, Cold Spring Harbor Laboratory Press, New York (1989), both of which are incorporated herein by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eukaryotic promotors differ from those of procaryotic promotors. Furthermore, eukaryotic promotors and accompanying genetic signals may not be recognized in or may not function in a procaryotic system, and, further, procaryotic promoters are not recognized and do not function in eukaryotic cells.

Similarly, translation of mRNA in procaryotes depends upon the presence of the proper procaryotic signals which differ from those of eukaryote. Efficient translation of MRNA in procaryotes requires a ribosome binding site called the Shine-Dalgamo (SD) sequence on the mRNA. This sequence is a short nucleotide sequence of mRNA that is located before the start codon, usually AUG, which encodes the amino-tenninal methionine of the protein. The SD sequences are complementary to the 3'-end of the 16S rRNA (ribosomal RNA) and probably promote binding of MRNA to ribosomes by duplexing with the rRNA to allow correct positioning of the ribosome. For a review on maximizing gene expression, see Roberts, T. M., et al., "Maximizing Gene Expression on a Plasmid Using Recombination in vitro," *Methods Enzymol.*, 68:473–82 (1979), which is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in *E. coli*, its bacteriophages, or plasmids, promotors such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Additionally, any SD-ATG combination produced by recombinant DNA or other techniques involving incorporation of synthetic nucleotides may be used.

Once the DNA molecules of the present invention have been cloned into an expression system, it is ready to be incorporated into a host. Such incorporation can be carried out by the various forms of transformation noted above, depending upon the vector/host cell system. Suitable host cells include, but are not limited to, bacteria, virus, yeast, mammalian cells, and the like. Peptides can also be constructed synthetically as an alternative to recombinant formation.

The transfection vector may also contain a negative selection marker which may be used to separate desired transfected cells from non-transfected cells. Various negative selection markers are well known in the art and numerous selection markers are continually being developed. Such negative selection markers include, among others, Aminoglycoside phosphotransferase (APH), Dihydrofolate reductase (DHFR):Methotrexate resistant, Hygromycin-B-phosphotransferase (HPH), Thymidine kinase (ThK), Xanthine-guanine phosphoribosyltransferase (XGPRT), and Adenosine deaminase (ADA).

It should also be noted that known non-viral methods of transfecting a host cell, either ex vivo or in vivo, may also be employed. Such non-viral methods include the use of cationic lipids combined with plasmid DNA to be introduced into the cellular host, and the use of non-aggregating plasmid DNA particles which are combined with a plurality of cationic monomers. Both of these methods allow for targeted cellular uptake of the plasmid DNA, which is then expressed by the host cells.

Following transfection, the cell population exposed to the expression vector is grown in a growth medium containing a drug that prevents growth of non-transfected cells. After about 48 to 72 hours, when transient expression occurs, non-transfected cells will die. The remaining cells in the growth medium will be those which have been transfected and are expressing the SSGR protein. It is from the transformed cells that the protein or polypeptide of the present invention may be obtained and, preferably, purified.

The proteins or polypeptides of the present invention are preferably produced in purified form by conventional techniques. To isolate the proteins, the *Escherichia coil* host cell carrying a recombinant plasmid is propagated, homogenized, and the homogenate is centrifuged to remove bacterial debris. The cleared lysate may be precipitated and then subjected to gel filtration in an appropriately sized dextran or polyacrylamide column to separate the proteins. If necessary, the protein fraction may be further purified by other chromatography, such as by HPLC.

The purified proteins or polypeptides can be utilized to detect the presence of antibodies raised by such proteins or polypeptides in a sample of mammalian origin.

The SSGR proteins or polypeptides of the present invention are also useful in raising antibodies, which may be used in assays to determine whether a tissue or cell sample contains an active SSGR protein. The antibodies of the present invention can be monoclonal or polyclonal.

Monoclonal antibody production may be effected by techniques which are well-known in the art. The process basically involves obtaining immune cells (e.g. lymphocytes) from the spleen of a mammal (e.g., mouse) which has been previously immunized with the antigen of interest (i.e., a protein or polypeptide product expressed by a transfected cell or otherwise prepared, either in vivo or in vitro, using known techniques). The antibody-secreting lymphocytes are then fused with (mouse) myeloma cells or transformed cells, which are capable or replicating indefinitely in cell culture, thereby producing an immortal immunoglobulin-secreting cell line. The resulting fused cells, or hybridomas, are cultured and the resulting colonies are screened for the production of the desired monoclonal antibodies.

Colonies producing such antibodies are cloned, and grown either in vivo or in vitro to produce large quantities of the desired monoclonal antibody. A description of the theoretical basis and practical methodology of fusing such cells is set forth in Kohler, G., and Milstein, C., "Continuous Cultures of Fused Cells Secreting Antibody of Predefined Specificity," *Nature*, 256:495 (1975), which is incorporated herein by reference.

Mammalian lymphocytes are immunized by in vivo immunization of the animal (e.g., mouse, rat, etc.) with one of the isolated protein or polypeptide products (e.g., human Hrad17, human Hrad1, human Hhus1, mouse Hrad1, mouse Hhus1 ) of the present invention. More specifically, the animal is immunized with an isolated protein or polypeptide that comprises an amino acid sequence of SEQ. ID. No. 2, SEQ. ID. No. 4, SEQ. ID. No. 6, SEQ. ID. No. 8, or SEQ. ID. No. 10. Of course, a mouse would be unsuitable for use in raising polyclonal antibodies against mouse Hrad1 and mouse Hhus1; instead, a different animal (e.g., rat, rabbit, etc.) should be used. Such immunizations are repeated as necessary at intervals of up to several weeks to obtain a sufficient titer of antibodies. The isolated protein or oligopeptide product of the present invention is carried in appropriate solutions or adjuvants. Following the last boost, the animals are sacrificed and spleen cells removed.

Fusion with mammalian myeloma cells or other fusion partners capable of replicating indefinitely in cell culture is effected by standard and well-known techniques, for example, by using polyethylene glycol (PEG) or other fusing agents. See Milstein, C., et al., "Fusion Between Immunoglobulin-Secreting and Nonsecreting Myeloma Cell," *Eur. J. Immunol.*, 6:511 (1976), which is incorporated herein by reference. This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Such antibodies are typically raised by administering an antigen (e.g., SSGR proteins such as human Hrad1, human Hrad17, human Hhus1, mouse Hrad1, or mouse Hhus1) subcutaneously to New Zealand white rabbits which have first been bled to obtain pre-immune serum. The antigens can be injected at a total volume of 100 $\mu$l per site at six different sites. Each injected material will contain a protein or polypeptide of the present invention carried in appropriate solutions or adjuvants. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized. This and other procedures for raising polyclonal antibodies are disclosed in Harlow, E., et al., editors, *Antibodies: A Laboratory Manual* (1988), which is incorporated herein by reference.

In addition to utilizing whole antibodies, the methods of the present invention encompass the use of binding portions of such antibodies. Such antibody fragments can be made by conventional procedures, such as proteolytic fragmentation procedures, as described in Goding, J., *Monoclonal Antibodies: Principles and Practice*, pp. 98–118, N.Y. Academic Press (1983), which is incorporated herein by reference.

In yet another aspect of the present invention, the antibodies or binding portions of the present invention can be used as in diagnostic assays to detect expression of particular SSGR genes. These techniques permit detection of such expression in a sample of the following tissue or body fluids: blood, spinal fluid, sputum, pleural fluids, urine, bronchial alveolar lavage, lymph nodes, bone marrow, or other biopsied materials.

Antibodies or binding portions are used in an assay system having a sandwich or competitive format. Examples of suitable assays include an enzyme-linked immunosorbent assay, a radioimmunoassay, a gel diffusion precipitation reaction assay, an immunodiffusion assay, an agglutination assay, a fluorescent immunoassay, a protein A immunoassay, or an immunoelectrophoresis assay.

According to another embodiment of the present invention, a method (performed as a diagnostic assay) is provided for identifying cancer cells in a mammal by providing antibodies or binding portions thereof raised against the SSGR proteins. The method comprises contacting a sample of tissue or bodily fluids with the antibody or binding portion and detecting the presence of any SSGR proteins in the sample. This method involves the use of assay systems such as an enzyme-linked immunosorbent assay, a radioimmunoassay, an immunodiffusion assay, an agglutination assay, a fluorescent immunoassay, a protein A immunoassay, and an immunoelectrophoresis assay. These assay systems are used to measure the level of expression for normal cells and suspected cells from a tissue sample. Labeling of the antibody or binding portion thereof allows for the detection and measurement of relative expression levels. By comparing the level of expression between normal cells and suspected cells from a tissue sample, a pre-cancerous or cancerous state may be identified by the reduced expression level of the gene product, or the complete absence of the gene product.

For example, tumor cell lines may be analyzed or screened by immunofluorescent staining of the SSGR proteins. Differences in immunofluorescent staining patterns, in comparison to the pattern seen in normal cells, would reveal an absent protein or altered cellular distribution of the protein, which could indicate that a mutation had abolished gene expression or resulted in a protein with altered function in the cell.

Protein extracts of cell lines may be analyzed or screened by immunoprecipitation experiments, which selectively purify the antigen recognized by the antibody, along with any associated factors. For example, this could be used to detect a protein of altered size or quantity in tumor cell lines, indicating that a mutation had resulted in the synthesis of abnormally sized proteins or abnormally high or low amounts of the protein.

Monoclonal antibodies have the advantage of recognizing a specific epitope on the antigen, and monoclonals against the SSGR proteins may be highly specific and valuable in the applications described above. In addition, since the antigen-antibody interactions are of uniform avidity for monoclonals, specific monoclonals may be identified that will bind the proteins and also quantitatively release them under specific conditions (e.g., 2M $MgCl_2$). Monoclonals such as this may be useful for immuno-affinity purification procedures, such as immuno-affinity columns.

In an alternative diagnostic embodiment of the present invention, the DNA molecules of the present invention or RNA transcripts thereof may be used as nucleic acid probes in nucleic acid hybridization assays for detecting the presence of complementary DNA or RNA in various tissue samples as described above. The nucleic acid probes of the present invention may be used in any nucleic acid hybridization assay system known in the art, including, but not limited to, Southern blots (Southern, E.M., "Detection of Specific Sequences Among DNA Fragments Separated by Gel Electrophoresis," *J. Mol. Biol.*, 98:503–17 (1975), which is hereby incorporated by reference), Northern blots (Thomas, P. S., "Hybridization of Denatured RNA and Small DNA Fragments Transferred to Nitrocellulose," *Proc. Nat'l Acad. Sci. USA*, 77:5201–05 (1980), which is hereby incorporated by reference), and Colony blots (Grunstein, M., et al., "Colony Hybridization: A Method for the Isolation of Cloned cDNAs that Contain a Specific Gene," *Proc. Nat'l Acad. Sci. USA*, 72:3961–65 (1975), which is incorporated herein by reference). Alternatively, the isolated DNA molecules of the present invention or RNA transcripts thereof can be used in a gene amplification detection procedure (e.g., a polymerase chain reaction). Erlich, H. A., et. al., "Recent Advances in the Polymerase Chain Reaction", *Science* 252:1643–51 (1991), which is incorporated herein by reference.

The nucleic acid molecules of the present invention can also be used to identify homologous single strand gap genes from other organisms, preferably other mammalian organisms. Nucleic acid (DNA or RNA) probes of the present invention will hybridize to complementary nucleic acid under stringent conditions. Less stringent conditions may also be selected. Generally, stringent conditions are selected to be about 50° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. The $T_m$ is dependent upon the solution conditions and the base composition of the probe, and for DNA:RNA hybridization may be calculated using the following equation:

$$\begin{aligned} T_m = 79.8° \text{ C.} &+ (18.5 \times \text{Log}[\text{Na}+]) \\ &+ (58.4° \text{ C.} \times \%[G+C]) \\ &- (820/\#bp \text{ in duplex}) \\ &- (0.5 \times \% \text{ formamide}) \end{aligned}$$

*Promega Protocols and Applications Guide*, 2d ed., Promega Corp., Madison, Wis. (1991), which is hereby incorporated by reference. Nonspecific binding may also be controlled using any one of a number of known techniques such as, for example, blocking the membrane with protein-containing solutions, addition of heterologous RNA, DNA, and SDS to the hybridization buffer, and treatment with RNase.

Generally, suitable stringent conditions for nucleic acid hybridization assays or gene amplification detection procedures are as set forth above or as identified in Southern, "Detection of Specific Sequences Among DNA Fragments Separated by Gel Electrophoresis," *J. Mol. Biol.*, 98:503–517 (1975), which is hereby incorporated by reference. For example, conditions of hybridization at 42° C. with 5×SSPE and 50% formamide with washing at 50° C. with 0.5×SSPE can be used with a nucleic acid probe containing at least 20 bases, preferably at least 25 bases or more preferably at least 30 bases. Stringency may be increased, for example, by washing at 55° C. or more preferably 60° C. using an appropriately selected wash medium having an increase in sodium concentration (e.g., 1×SSPE, 2×SSPE, 5×SSPE, etc.). If problems remain with cross-hybridization, further increases in temperature can also be selected, for example, by washing at 65° C., 70° C., 75° C., or 80° C. By adjusting hybridization conditions, it is possible to identify sequences having the desired degree of homology (i.e., greater than 80%, 85%, 90%, or 95%) as determined by the TBLASTN program (Altschul, S. F., et al., "Basic Local Alignment Search Tool," *J. Mol. Biol.* 215:403–410 (1990), which is hereby incorporated by reference) on its default setting.

The nucleic acid probes of the present invention may be used to identify and/or classify cancerous cells present in a human or mouse tissue sample. The various methods detect the presence of DNA or RNA transcripts in a tissue or cell sample whereby absence or mutation of the gene, or reduced transcription or non-transcription of the gene may signify a pre-cancerous or cancerous condition, respectively. Such detection is facilitated by providing the DNA molecule of the present invention with a label such as a radioactive compound, a fluorescent compound, a chemiluminescent compound, or an enzymatic compound. See U.S. Pat. No. 5,688,641 to Sager et al., which is incorporated herein by reference.

According to one embodiment of the present invention, a method (performed as a diagnostic assay) is provided for identifying cancer cells in a human by providing a nucleic acid probe of the present invention which specifically hybridizes to complementary DNA or RNA transcripts from a SSGR gene (e.g., human HRAD1, human HRAD17, human HHUS1, mouse HRAD1, or mouse HHUS1). The method comprises providing a nucleic acid probe in a detection procedure of the type described above, contacting a sample with the probe, and detecting any reaction which indicates the presence of the complementary DNA or RNA transcripts in the sample. The levels of hybridization in normal samples and test samples can then be compared.

For example, a first tissue sample comprising cancerous cells is obtained and a second tissue sample comprising non-cancerous cells is also obtained. Using a Northern blot format, the nucleic acid probes are contacted under high-stringency hybridizing conditions with RNA of each of the first and second tissue samples and then the degree of hybridization between the probes and the RNA samples is measured (i.e., detecting the presence of any type of conventional label). By comparing the degree of hybridization for the first and second samples, a cancerous or pre-cancerous condition is detectable. Using an in situ hybridization format, the labeled nucleic acid probes are inserted into morphologically intact cells present within a tissue sample and hybridization is carried out using hybridizing conditions well known to those skilled in the art. The labeled probes will identify non-cancerous cells, while pre-cancerous and cancerous cells exhibit reduced labeling. These aforementioned diagnostic assay are useful to provide an estimation of the number of cancerous cells present in a given tissue sample, and/or whether a given cell is likely to be cancerous.

It is expected that in some instances cancerous tissue will have normal levels of expression of RNA specific to SSGR proteins, while in other instances RNA expression will be reduced. In yet other cases, the RNA expression level will be normal but the RNA will carry a mutation that leads to the production of an SSGR protein with reduced or no activity. Three situations are considered in which a cancer is typed with respect to whether the SSGR genes are altered in expression or activity and a specific plan for treatment of the cancer is indicated.

In the first instance, a patient with a cancer characterized by a lower than normal level of transcription for one or more suspected or known tumor suppressor genes can be treated by the administration of drugs (e.g., chemical or biological agents, etc.) useful for inducing DNA damage, or treated by radiotherapy, which also acts by inducing DNA damage. Such cancer cells will be particularly susceptible to DNA damage due to the disruption of the single strand gap response pathway of the cell cycle checkpoint that allows time for DNA damage to be repaired.

In the second instance, a patient with a cancer having normal expression of the SSGR genes can be treated by the administration of drugs that have the activity of the SSGR proteins as a target. This is advantageous because of the role of the SSGR genes in supporting the repair of DNA damage. Compounds that reduce or block DNA repair by inhibiting the single strand gap response pathway will heighten the potency and effectiveness of anti-tumor drugs, such as cis-platin, that work by inducing DNA damage.

A patient with a cancer can be treated, in conjunction with chemotherapeutic drugs that work by inducing DNA damage, by the administration of drugs (e. g. chemical or biological agents, etc.) useful for decreasing levels of transcription of an SSGR gene in cancerous or pre-cancerous cells or as an inhibitor of the activity of the normal gene product, thereby increasing the susceptibility of the cancer to the chemotherapeutic or radiotherapeutic DNA-damaging treatment. Development of such drugs necessarily depends upon useful screening methods to determine whether the drug will have the desired effect of decreasing expression.

Therefore, another aspect of the present invention involves screening assays for the detection of suitable drugs useful for decreasing the expression of or inhibiting the activity of a single SSGR protein of the present invention. For example, small molecules have been identified that can activate the function of mutant p53 tumor suppressor protein. Hupp, T. R., et al., "Small Peptides Activate the Latent Sequence-Specific DNA Binding Function of p53," *Cell*, 83:237–45 (1995), which is incorporated herein by reference. Alternatively, if the role of the gene is to negatively regulate another protein, small molecules may be identified that activate the target protein directly.

According to one embodiment, screening to identify potential therapeutic drugs for the treatment of cancer involves the use of cultured cells. The cultured cells are treated with the drug, or any combination of drugs, to determine which drug(s) are capable of decreasing expression of the gene product. Identification of a decrease in the SSGR gene expression can be analyzed using the assay systems described above.

Another method to identify potential pharmacological agents involves assaying for compounds that interfere with the biochemical activity of an SSGR protein. For instance, Hrad17 is expected to exhibit affinity to single-strand DNA. This expectation arises from its high degree of homology with the subunits of the RFC complex, a known single-strand DNA binding factor involved in DNA replication. Griffiths, D. J. F., et al., "Fission Yeast rad17: a Homolog of Budding Yeast RAD24 that Shares Regions of Sequence Similarity with DNA Polymerase Accessory Proteins," *EMBO J.*, 14:5812–23 (1995), which is incorporated herein by reference. An assay mixture contains a DNA molecule with a single-strand region and has structural similarity to molecules with which Hrad17 naturally binds. The mixture also contains Hrad17 protein, typically recombinantly produced, and a candidate pharmacological agent. The mixture is incubated under conditions which, except for the presence of the candidate pharmacological agent, Hrad17 binds to the single-strand DNA molecule. After incubation, the presence of specific binding is detected in any convenient way. For instance, a separation step is used to separate bound from unbound components. Then, detection of the single strand DNA is carried out by means of a label that is coupled to the DNA molecule.

Other possible activities that may be anticipated in the single strand gap response pathway include protein-protein interaction, protein-ATP interaction, ATPase activity, exo-nuclease activity, and protein phosphorylation or dephosphorylation. In each case, a high throughput screen could be designed in which the SSGR protein is contacted with a candidate pharmaceutical under conditions that yield the expected activity. The presence or absence of the activity then could be detected. Useful candidate pharmaceuticals would be identified as those which prevent the activity of the SSGR protein.

The SSGR proteins may exist in a complex with one another. Lindsay, H. M., et al., "S-phase-Specific Activation of Cds1 Kinase Defines a Subpathway of the Checkpoint Response in *Schizosaccharomyces pombe,*" *Genes Dev.*, 12:382–95 (1998), which is hereby incorporated by reference. As a result the proteins or polypeptides of the present invention may be used in vitro for the formation of complexes with one another, or with other cellular components likely to bind them, such as ATM (the protein Mutated in Ataxia-Telangiectasia), or ATR (an AT-Related protein). The disruption of complex formation may be used as an assay for small molecules or biological agents that may disrupt function of single strand gap genes in the cell.

The proteins or polypeptides may also be used for in vitro activation of human protein kinases such as ATM, ATR, or the human homologs of the *Schizosaccharomyces pombe* Chk1 or Cds1 kinases. Repression of kinase activation could, again, be used as an assay for chemical or biological agents that would disrupt the protein function in vivo.

One or more of the proteins or polypeptides may become phosphorylated themselves in vivo in response to DNA damage. The phosphorylation of these proteins in vitro may, again, be used as an assay for chemical or biological agents that would disrupt protein function in vivo.

One or more of the proteins or polypeptides may exhibit ATPase activity or other enzymatic activity in vitro. It is believed that Hrad17 will exhibit ATPase activity, due to its extensive amino acid sequence similarity with the subunits of a known DNA-dependent ATPase, the RFC complex. Griffiths, D. J. F., et al., "Fission Yeast rad17: a Homolog of Budding Yeast RAD24 That Shares Regions of Sequence Similarity with DNA Polymerase Accessory Proteins," *EMBO J.*, 14:5812–23 (1995), which is hereby incorporated by reference. The inhibition of ATPase or other enzymatic activity carried out by these proteins or polypeptides of the present invention could, again, be used as an assay for small molecules that would disrupt protein function in vivo.

In the third instance under consideration, a cell that may have a predisposition to cancer is identified with reduced or abolished expression of an SSGR gene. In this aspect of the present invention the gene may be supplied by gene therapy (e.g., liposome fusion, gene gun, viral gene vector), therby preventing or delaying the onset of neoplasia. The DNA molecules of the present invention can be used to express SSGR proteins and polypeptides in vivo, which is often referred to as gene therapy.

Thus, for example, cells from a patient may be engineered with a polynucleotide (DNA or RNA) encoding Hrad17, Hrad1, or Hhus1 ex vivo, with the engineered cells then being provided to a patient to be treated with the polypeptide. This manner of performing gene therapy may be useful for treating certain types of leukemia and other cancers. Such methods are well-known in the art. For example, cells may be engineered by procedures known in the art by use of a retroviral particle containing RNA encoding a polypeptide of the present invention. Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention.

Construction of appropriate expression vehicles and vectors for gene therapy applications will depend on the organism to be treated and the purpose of the gene therapy. The selection of appropriate promoters and other regulatory DNA will proceed according to known principles, based on a variety of known gene therapy techniques. For example, retroviral mediated gene transfer is a very effective method for gene therapy, as systems utilizing packaging defective viruses allow the production of recombinants which are infectious only once, thus avoiding the introduction of wild-type virus into an organism. For a review of retrovirus vectors, see Austin, C. P., et al., "Retrovirus Mediated Gene Transduction into Vertebrate CNS," *Gene Ther.*, 1 Suppl 1:S6–9 (1994), and Eglitis, M. A., et al., "Gene Transfer into Hematopoietic Progenitor Cells from Normal and Cyclic Hematopoietic Dogs Using Retroviral Vectors," *Blood*, 71:717–22 (1988), both of which are incorporated herein by reference. Other viral vectors are derived from adenovirus, herpesviruses, vaccinia virus, etc. Alternative methodologies for gene therapy utilize non-viral transfer methods, including but not limited to calcium phosphate co-precipitation, mechanical techniques such as microinjection, membrane fusion-mediated transfer via liposomes, as well as direct DNA uptake and receptor-mediated DNA transfer.

As another aspect of the invention, knowledge of the gene sequences for the DNA molecules of the present invention enables one skilled in the art to generate knockout animal strains that lack functional copies of the genes. Thus, the present invention provides transgenic animals whose somatic and germ cells lack or possess a disruption in a gene encoding a single strand gap response protein involved in activation of a DNA repair/cell cycle checkpoint pathway. Such knockout animal strains will make excellent model systems for studying tumor formation and treatment. Donehower, L. A., et al., "Mice Deficient for p53 are Developmentally Normal but Susceptible to Spontaneous Tumors," *Nature*, 356:215–21 (1992); Harvey, M., et al., "A Mutant p53 Transgene Accelerates Tumor Development in Heterozygous but not Nullizygous p53-Deficient Mice," *Nature Genetics*, 9:305–11 (1995); and Hann, B. C., et al., "The Dominating Effect of Mutant p53," *Nature Genetics*, 9:221–2 (1995), all of which are incorporated herein by reference. Suitable knock-out animals include mice, rats, and any other animal model for carcinogenesis in which the loss of a functional tumor suppressor gene in the animal would be useful for studying how homologous genes behave as tumor suppressors in humans.

In particular, the present invention provides transgenic mice whose somatic and germ cells lack or possess a disruption in a SSGR gene encoding mouse Hrad1 (Hrad1 knock-out mouse) or mouse Hhus1 (Hhus1 knock-out mouse).

Both the Hrad1 knock-out mouse and the Hhus1 knock-out mouse will be characterized by spontaneous tumor development. This phenotype is conferred to the mouse (mice) by disruption of the SSGR gene HRAD1 or HHUS1, respectively. The disruption of the mouse HRAD1 or HHUS1 gene occurs as a result of meiotic homologous recombination between a replacement vector nucleic acid sequence and the mouse HRAD1 or HHUS1 genes. Homologous recombination is carried out according to the method of Capecchi, M. R., *Science*, 244:1288–92 (1989), which is incorporated herein by reference. It is understood that the replacement vector nucleic acid sequence can comprise any known nucleic acid sequence (i.e., DNA sequence) provided that it disrupts the natural mouse gene (e.g., mouse HRAD1, mouse HHUS 1) upon homologous recombination in a manner sufficient to prevent expression of the mouse Hrad1 protein or the mouse Hhus1 protein.

Briefly, a targeting vector containing the desired mutation is introduced into embryonic-derived stem (ES) cells by electroporation, microinjection or other like means. In some of the ES cells, the targeting vector pairs with the cognate chromosomal DNA sequence and transfers the mutation to the genome by homologous recombination. Screening procedures, enrichment procedures, or hybridization procedures are then utilized to identify those transformed ES cells in which the targeted event has occurred. An appropriate cell is then cloned and maintained as a pure population. The transformed ES cells are injected into a blastocoel cavity of a preimplantation mouse embryo and the blastocyst is surgically transferred to the uterus of a foster mother, where development is allowed to progress to term. Chimeric offspring heterozygous for the desired trait are then mated to obtain homozygous individuals, and colonies characterized by deficiency in the targeted gene are established.

In accordance with the invention, the mouse HRAD1 or HHUS1 gene is disrupted (i.e., chromosomal defect introduced into the respective HRAD1 or HHUS1 gene locus) using a vector. Examples of such vectors include, without limitation, (1) an insertion vector as described by Capecchi, M. R., *Science*, 244:1288–92 (1989), which is hereby incorporated by reference; (2) a vector based upon promoter trap, polyadenylation trap, "hit and run" or "tag-and-exchange" strategies, as described by Bradley, A., et al., "Modifying the Mouse: Design and Desire," *Biotechnology* 10:534–39 (1992); and Askew, R., et al., "Site-Directed Point Mutations in Embryonic Stem Cells: a Gene Targeting Tag-and-Exchange Strategy," *Mol. Cell Biol.*, 13:4115–24 (1993), both of which are incorporated herein by reference. These vectors may or may not include negative selection markers (e.g., a HSV-tk gene), which when used, may allow enhancement of targeted recombinant isolation. Mansour, S. L., et al., "Disruption of the Proto-Oncogene int-2 in Mouse Embryo-Derived Stem Cells: a General Strategy for Targeting Mutations to Non-Selectable Genes," *Nature*, 336:348–52 (1988); and McCarrick, J. W., et al., "Positive-Negative Selection Gene Targeting with the Diptheria Toxin A-chain Gene in Mouse Embryonic Stem Cells," *Transgen. Res.*, 2:183–90 (1993), both of which are incorporated herein by reference. These markers may be part of the targeting vector or may be co-transfected into the ES cells.

In producing a knock-out mouse according to the present invention, transformed mouse cell lines deficient for the HRAD 1 gene or the HHUS 1 gene can be identified by standard techniques in the art. Once identified, these host cells are cultured under conditions which facilitate growth of the cells as will be apparent to one skilled in the art. Thereafter, stable transformants may be selected on the basis of the expression of one or more appropriate gene markers present or inserted into the replacement vector. The expression of the marker genes should indicate the targeted or desired disruption of the HRAD1 or HHUS1 gene. It is understood that any known gene marker may be used herein. Such gene markers can be derived from cloning vectors, which usually contain a positive marker gene.

EXAMPLES

The Examples set forth below are for illustrative purposes only and are not intended to limit, in any way, the scope of the present invention.

Example 1

Isolation and Sequencing of *Schizosaccharomyces pombe* rad17 Homologs

The Institute for Genome Research ("TIGR") level 2 database was searched for partial cDNA sequences and translated amino acid sequences showing sequence similarity to the *Schizosaccharomyces pombe* rad17 protein sequence. One cDNA clone, EST59509, was identified. This clone was obtained and its DNA sequence was determined using DNA Sequenase 2.0 from Amersham, Inc. It was found not to encode a full-length cDNA molecule. The database of expressed sequence tags (ESTs) ESTs at the National Institutes of Health was then searched with the translated amino acid sequence of EST59509 using the NCBI (National Center for Biotechnology Information) BLAST server (Altschul, S. F., et al., "Basic Local Alignment Search Tool," *J. Mol. Biol.*, 215:403–10 (1990), which is hereby incorporated by reference), and the TBLASTN program. Two ESTs were found that identified potentially full-length human cDNA clones (Accession T10666, clone hbc863; and Accession AA133547, clone 586844).

The DNA sequences of the two clones were determined. As a result, it was found that the sequences of the three clones overlapped one another and were assembled into one cDNA sequence containing an open reading frame of about 2000 nucleotides. This appeared long enough to be able to encode a protein of the expected size. However, the cDNA sequence was not complete, because no initiator codon was present in the 5' portion of the open reading frame.

A full-length cDNA was isolated via the technique of rapid amplification of cDNA ends (RACE), using Marathon-Ready cDNA (Clontech, Palo Alto, Calif.) as a template. The polymerase chain reaction (PCR) was used to amplify the desired cDNA. Primer 2402 annealed to the 3' end of the HRAD17 cDNA and primed synthesis of the antisense strand. Primer AP1 (Clontech) annealed to the Marathon cDNA adaptor product strand at the 5' end of the cDNA and primed synthesis of the sense strand. Primer 2402, a 3' terminus primer, is identified as SEQ. ID. No. 17 and contains the following sequence:

GCGGGATCCC TATGTCCCAT CACTCTCGTA GTCTTC 36

The PCR amplification was performed for 30 cycles of 94° C. for 30 sec and 68° C. for 7 min. in a reaction volume of 50 µl containing 40 mM Tricine-KOH, pH 9.2 at 25° C., 15 mM KOAc, 3.5 mM Mg(OAc)$_2$, 75 µg/ml bovine serum albumin, 200 µM each dNTP, 10 pmol each of primer API and 2402, 0.5 ng Marathon-Ready CDNA template, 1 µl Advantage KlenTaq Polymerase Mix (Clontech). Amplified DNA products (15 1 µl) were analyzed by electrophoresis through a 1.0% agarose gel. An amplified product of 2.6 kilobases was observed. A second PCR amplification was performed under the identical conditions described above, with the exception that the template used was 0.5 ng of PCR reaction products of the first reaction and 10 pmol of primer AP2 (Clontech) was used instead of primer AP1. Amplified DNA products were separated by electrophoresis through a 1.0% low-melting agarose gel and a gel slice containing the 2.6 kilobase amplified reaction product was excised from the gel. The 2.6 kilobase PCR product was cloned using the TOPO TA Cloning vector (Invitrogen, Carlsbad, Calif.). DNA minipreps (48) were carried out, yielding 27 clones containing the PCR product. Three clones were sequenced and found to contain the complete, identical, open reading frame.

SEQ. ID. No. 1 is the sequence of the cDNA designated human HRAD17, which was determined from the sequences of clones EST59509, hbc863, 586844, and the 5'-RACE products. SEQ. ID. No. 2 is the conceptual translate, identified as human Hrad17.

Example 2

Sequence Comparison of *Schizosaccharomyces pombe* rad17 Homologs

The database of ESTs at the National Institutes of Health was searched with the translated amino acid sequence of human Hrad17 using the NCBI BLAST server (Altschul, S. F., et al., "Basic Local Alignment Search Tool," *J. Mol. Biol.*, 215:403–10 (1990), which is hereby incorporated by reference), and the TBLASTN program.

A sequence specifying a gene from *Drosophila melanogaster* (Accession AA539148, clone LD17237) was identified. Clone LD17237, from the BDGP/HHMI Drosophila EST Project, was obtained from Genome Systems, Inc. The DNA sequence was determined, and it appeared to encode a full-length cDNA, identified as *Drosophila melanogaster* HRAD17. SEQ. ID. No. 11 is the nucleotide sequence of *Drosophila melanogaster* HRAD17. SEQ. ID. No. 12 is the conceptual translate, identified as *Drosophila melanogaster* Hrad17.

A sequence specifying a gene from *Caenorhabditis elegans* (Accession D75465, clone yk104h11) was identified. The DNA sequence was determined, and it appeared to encode a cDNA missing perhaps 5% of the gene at its 5' end. SEQ. ID. No. 13 is the nucleotide sequence of *Caenorhabditis elegans* HRAD17. SEQ. ID. No. 14 is the conceptual translate, identified as *Caenorhabditis elegans* Hrad17.

Figure 2C:
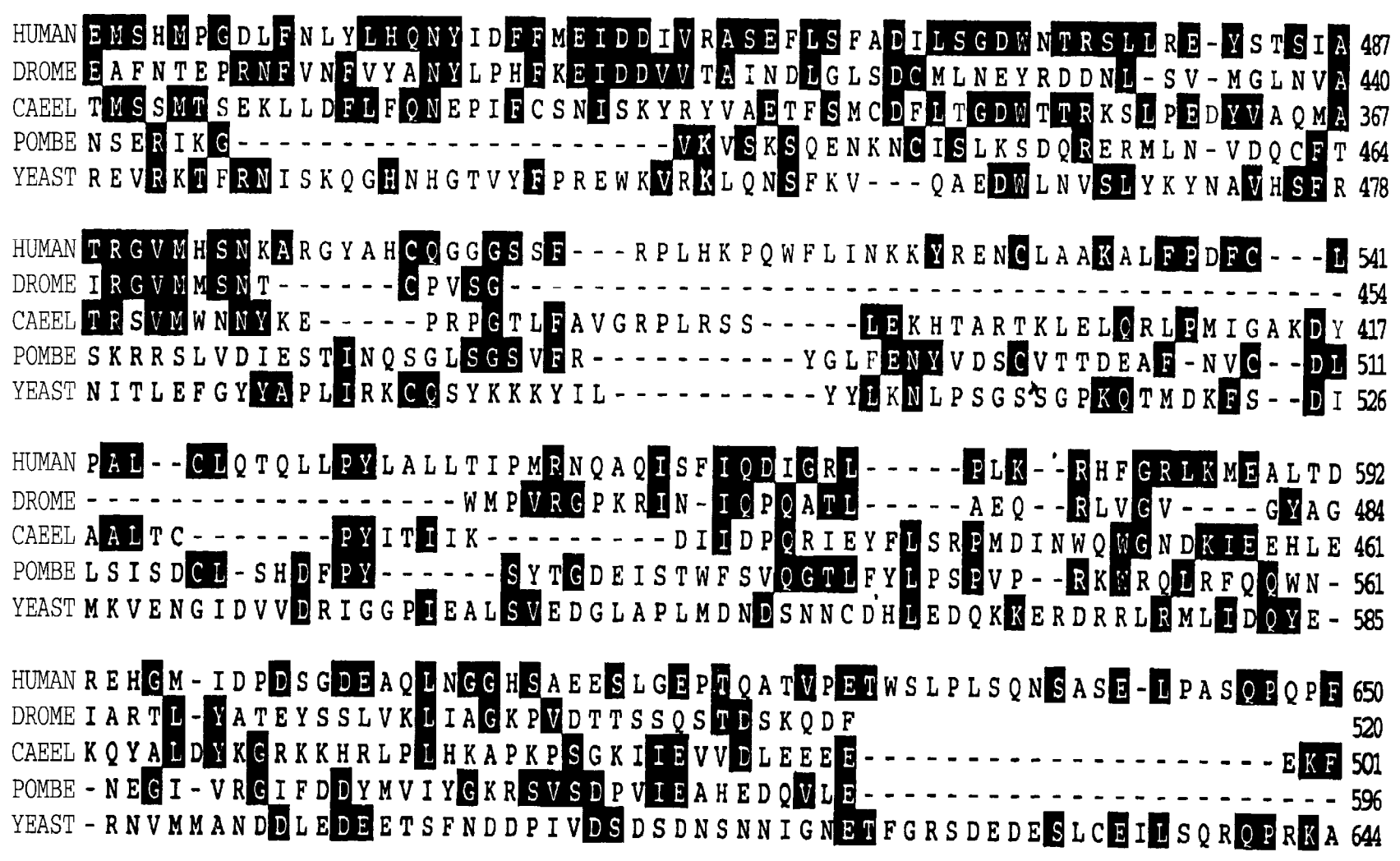

The predicted amino acid sequence of human Hrad17 showed significant similarity to homologs from *Drosophila melanogaster* (SEQ. ID. No. 12), *Caenorhabditis elegans* (SEQ. ID. No. 14), *Schizosaccharomyces pombe*, and *Saccharomyces cerevisiae*. An alignment of the five predicted amino acid sequences is shown in FIGS. 2A–D. A region that conforms to the P-loop ATP/GTP binding consensus sequence (Koonin, E. V., "A Common Set of Conserved Motifs in a Vast Variety of Putative Nucleic Acid-Dependent ATPases Including MCM Proteins Involved in the Initiation of Eukaryotic DNA Replication," *Nucleic Acids Res.*, 21:2541–47 (1993), which is incorporated herein by reference) was found in the N-terminal region of human Hrad17 (residues 126 to 133), as well as in the other four sequences (Griffiths, D. J. F., et al., "Fission Yeast rad17: a Homolog of Budding Yeast RAD24 That Shares Regions of Sequence Similarity with DNA Polymerase Accessory Proteins," *EMBO J.*, 14:5812–23 (1995), which is incorporated herein by reference). The similarities between the amino acid sequences of human Hrad17 and *Schizosaccharomyces pombe* rad17, a checkpoint control protein, suggest that human Hrad17 is likely a checkpoint control protein and likely plays a role in tumor suppression.

Example 3

Isolation and Sequencing of *Schizosaccharomyces pombe* rad1 Homologs

The database of ESTs at the National Institutes of Health was searched with the translated amino acid sequence of *Schizosaccharomyces pombe* rad1 using the NCBI BLAST server (Altschul, S. F., et al., "Basic Local Alignment Search Tool," *J. Mol. Biol.*, 215:403–10 (1990), which is incorporated herein by reference), and the TBLASTN program. Two ESTs were found that identified human cDNA clones (Accession AA029300, clone 470124, and Accession AA227739, clone 667461). The DNA sequences of the two clones were determined. Clone 470124 contained a deletion of 109 nucleotides that disrupts the amino acid coding region. This cDNA was not derived from tumor tissue, but from pregnant uterus. SEQ. ID. No. 3 shows the cDNA sequence of clone 667461, which was designated human HRAD1. SEQ. ID. No. 4 is the conceptual translate, identified as human Hrad1.

The database of ESTs at the National Institutes of Health was searched with the translated amino acid sequence of human Hrad1 using the NCBI BLAST server (Altschul, S. F., et al., "Basic Local Alignment Search Tool," *J. Mol. Biol.*, 215:403–10 (1990), which is incorporated herein by reference), and the TBLASTN program. A sequence specifying a gene from mouse (Accession AA387463, clone 789687) was identified. The DNA sequence was determined, and it appeared to encode a full-length cDNA. SEQ. ID. No. 5 shows the cDNA sequence of clone 789687, which was designated mouse HRAD1. SEQ. ID. No. 6 is the conceptual translate, identified as mouse Hrad1.

Example 4

Sequence Comparison of *Schizosaccharomyces Pombe* rad1 Homologs

The database of ESTs at the National Institutes of Health was searched with the translated amino acid sequence of Human Hrad1 using the NCBI BLAST server (Altschul, S. F., et al., "Basic Local Alignment Search Tool," *J. Mol. Biol.*, 215:403–10 (1990), which is incorporated herein by reference), and the TBLASTN program. A sequence specifying a gene from *Caenorhabditis elegans* (Accession D76378, clone yk117e8) was identified. The DNA sequence was determined, and it appeared to encode a full-length cDNA. SEQ. ID. No. 15 is the nucleotide sequence of *Caenorhabditis elegans* HRAD1. SEQ. ID. No. 16 is the conceptual translate, identified as *Caenorhabditis elegans* Hrad1.

Figure 3A:
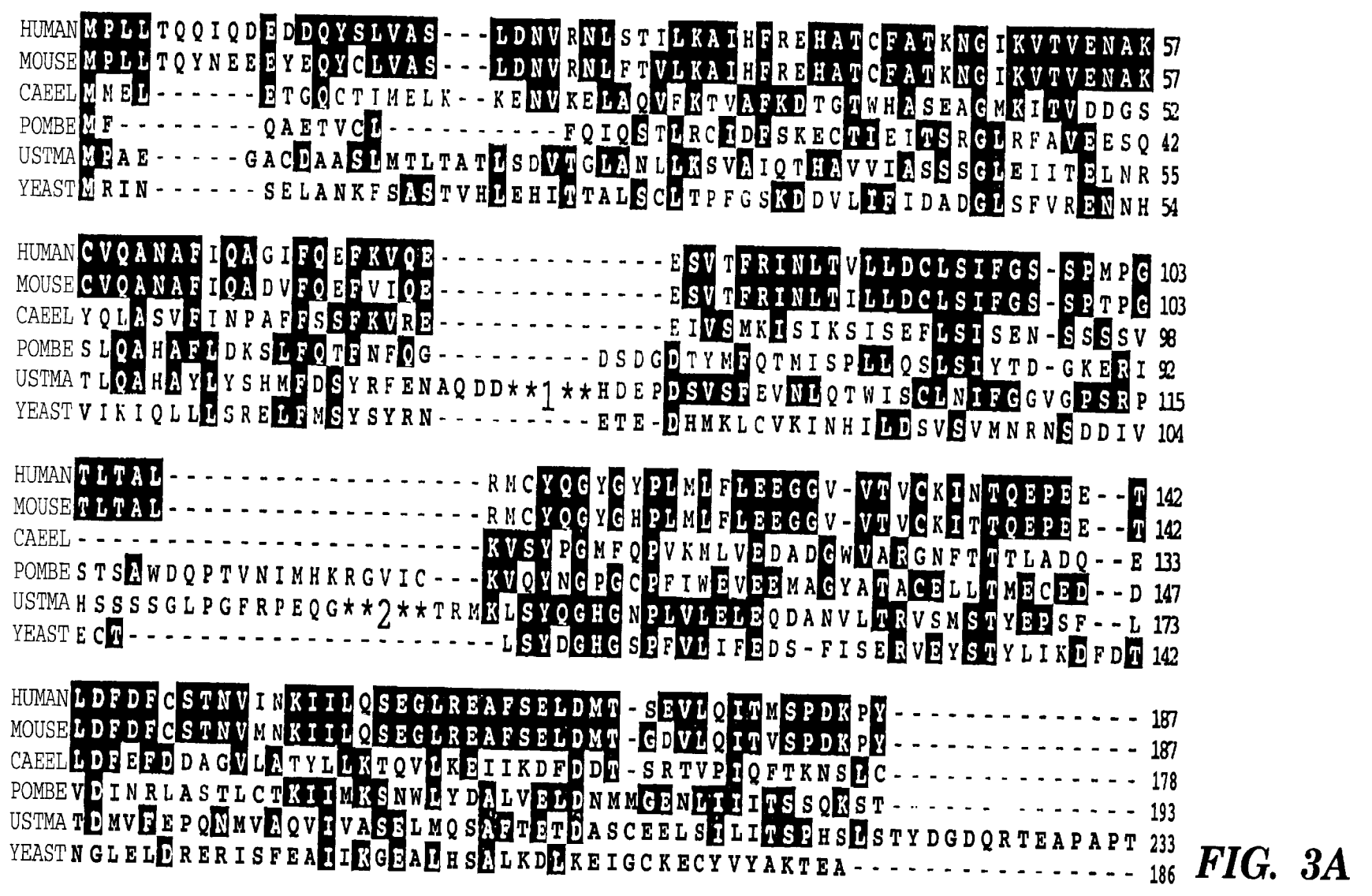

The predicted amino acid sequence of human Hrad1 (SEQ. ID. No. 4) showed critical similarity to homologs from mouse (SEQ. ID. No. 8), *Caenorhabditis elegans* (SEQ. ID. No. 16), *Schizosaccharomyces pombe, Ustilago maydis*, and *Saccharomyces cerevisiae*. An alignment of the six predicted amino acid sequences is shown in FIGS. 3A–B. The YxGxGxPxxxxxE motif (Siede, W., et al., "Cloning and Characterization of RAD17, a Gene Controlling Cell Cycle Responses to DNA Damage in *Saccharomyces cerevisiae*," *Nuc. Acids Res.*, 24:1669–75 (1996), which is incorporated herein by reference) was found in human Hrad1 (residues 112 to 124), as well as in the other five sequences, with the exception of one amino acid change in the *Caenorhabditis elegans* sequence.

The similarities between the amino acid sequences of human Hrad1 and mouse Hrad1 with *Schizosaccharomyces pombe* rad1, which is known to be involved in DNA repair mechanisms (Long, K. E., et al., "The *Schizosaccharomyces pombe* rad1 Gene Consists of Three Exons and the cDNA Sequence is Partially Homologous to the *Ustilago maydis* REC1 cDNA," Gene, 148:155–59 (1994), which is incorporated herein by reference), suggests that human Hrad1 and mouse Hrad1 likely play a role in DNA repair mechanisms and in tumor suppression.

Example 5

Isolation and Sequencing of *Schizosaccharomyces pombe* hus1 Homologs

The database of ESTs at the National Institutes of Health was searched with the translated amino acid sequence of *Schizosaccharomyces pombe* hus1 using the NCBI BLAST server (Altschul, S. F., et al., "Basic Local Alignment Search Tool," *J. Mol. Biol.*, 215:403–10 (1990), which is incorporated herein by reference), and the TBLASTN program. Two ESTs were found that identified human cDNA clones (Accession AA280710, clone 711713, and Accession R29753, clone F1-1279D). The DNA sequences of the two clones were determined. Neither clone encoded a full-length open reading frame. However, the two clones overlapped each other, having 259 nucleotides in common. The full-length cDNA sequence was determined. SEQ. ID. No. 7 shows the full length sequence of the cDNA molecule, which was designated human HHUS1. SEQ. ID. No. 8 is the conceptual translate, identified as human Hhus1.

The database of ESTs at the National Institutes of Health was searched with the translated amino acid sequence of human HHUS1 using the NCBI BLAST server (Altschul, S. F., et al., "Basic Local Alignment Search Tool," *J. Mol. Biol.*, 215:403–10 (1990), which is incorporated herein by reference), and the TBLASTN program. Two ESTs were found that identified mouse cDNA clones (Accession AA153060, clone 604141, and Accession AA218365, clone 658994). The DNA sequences of the two clones were determined. Neither clone encoded a full-length open reading frame. However, the two clones overlapped each other, having 108 nucleotides in common, and the full-length cDNA sequence was determined and was designated mouse HHUS1. SEQ. ID. No. 9 shows the cDNA sequence, which was designated mouse HHUS1. SEQ. ID. No. 10 is the conceptual translate, identified as mouse Hhus1.

Example 6

Sequence Comparison of *Schizosaccharomyces pombe* hus1 Homologs

The predicted amino acid sequence of human Hhus1 (SEQ. ID. No. 8) showed key similarity to homologs from mouse (SEQ. ID. NO. 10) and *Schizosaccharomyces pombe*. An alignment of the three predicted amino acid sequences is shown in FIGS. 4A–B. The Hhus1 homologs are believed to be involved in checkpoint control regulation and likely play a role in tumor suppression.

Example 7

Cloning HRAD1

PCR (Polymerase Chain Reaction) was used to introduce unique restriction sites at the 5' and 3' termini of human Hrad1. Primer 1705, which introduces a 5' terminus Nde I site, has the following sequence (SEQ. ID. No. 18):

AGGGAATTCC ATATGCCCCT TCTGACCCAA CAGATCCASA 39

Primer 1706, which introduces a 3' terminus BamHI site, has the following sequence (SEQ. ID. No. 19):

GCGGGATCCT CAAGACTCAG ATTCAGGAAC TTCTTC 36

PCR amplification was performed for 30 cycles of 94° C. for 1 min, 55° C. for 1 min, and 72° C. for 1 min in a reaction volume of 0.1 ml containing 10 mM KCl, 20 mM Tris-HCl (pH 8.8 @25° C.), 10 mM $(NH_4)_2SO_4$, 2 mM $MgSO_4$, 0.1% Triton X-100, 200 uM each dNTP, 20 pmol each primer 1705 and 1706, 2 ng template (clone 667461), and 1 unit Vent$^R$ (exo$^+$) DNA polymerase. Amplified DNA products were extracted with phenol/chloroform and ethanol precipitated prior to being digested with BamHI and NdeI restriction endonucleases (digested in a BamHI buffer for 3 hrs (NEB) with a 4-fold excess of each enzyme). Digested DNA was separated in a 1% low melting agarose gel. Gel slices were melted at 70° C. for 1 hr in a 0.1 M NaCl solution. DNA was extracted with phenol twice before being precipitated with ethanol. These primers yield an 870 nucleotide PCR product (NdeI/BamHI) which is ligated into a NdeI/BamHI digested pHK vector (5/1 ratio of insert/vector).

This vector contains an upstream sequence that has a polyhistidine sequence and a recognition site for a cAMP-dependent protein kinase. Kelman, Z., et al., "*Escherichia coli* Expression Vectors Containing a Protein Kinase Recognition Motif, His$_6$-tag and Hemagglutinin Epitope," *Gene* 166:177–78 (1995), which is incorporated herein by reference. The products of the ligation reaction were transformed into *Escherichia coli* strain XL-1 Blue for insert check and plasmid amplification. The same plasmid was subsequently transformed into *Escherichia coli* strain BL21(DE3) for protein expression. FIG. 5 shows the HRAD1 expression vector.

Example 8

Hrad1 Expression and Purification from Transformed *Escherichia coli*

Figure 6A:
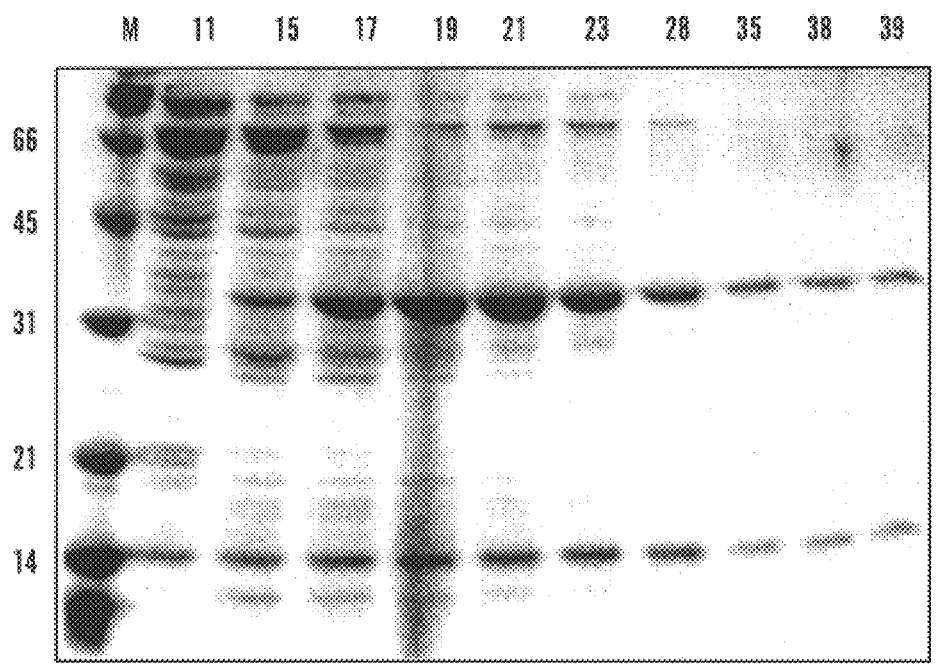
FIGS. 6A and 6B show the purification of Hrad1. Proteins were separated on a 12% SDS-Polyacrylamide gel and stained with Coomassie Blue R-250. Each lane contains 40 µl from the fraction indicated at the top of the gel. The first lane contains molecular weight markers (Biorad).
Figure 6B:
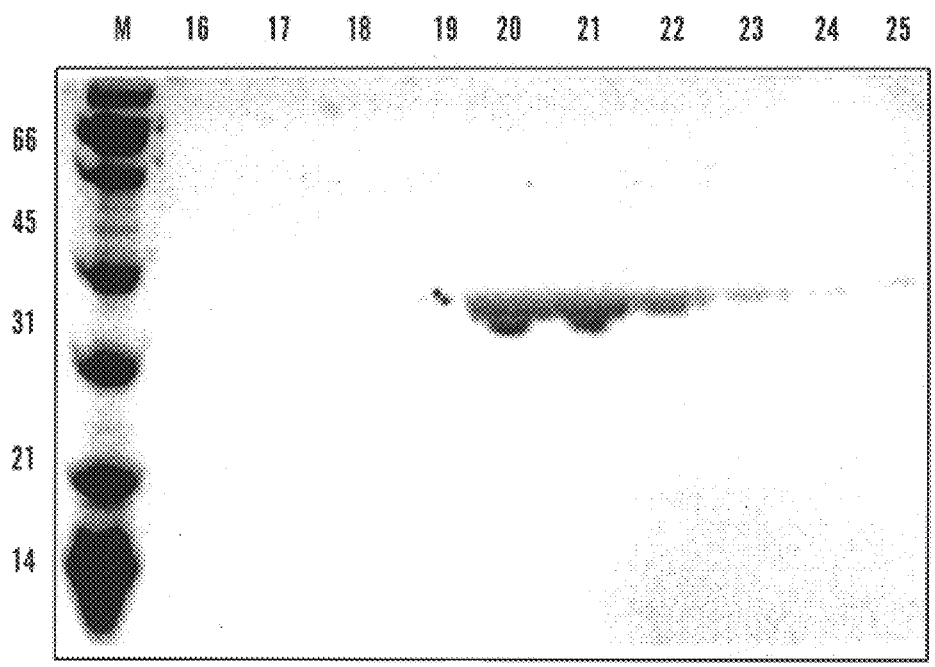

A single colony of *Escherichia coli* was grown in 10 ml LB (Luria Broth plus 200 ug/ml Ampillicin) to mid log phase ($OD_{595}$=0.5) and then used to inoculate a 12L culture for protein expression. Cells were grown at 37° C. to $OD_{595}$=0.5. Following addition of 1 mM IPTG, the temperature was lowered to 15° C. for an overnight induction (16 hrs). In the morning the cells were centrifuged, resuspended in 50 mM Tris-HCl, pH 8.0, 10% sucrose, 0.6% Brij-58, 1 mg/ml lysozyme and lysed by sonication 5×20 sec at 20% power. Cellular debris was removed by centrifugation for 15 min at 4° C. at 15,000 rpm. The cleared lysate was loaded onto a 20 ml chelated $Ni^{+2}$ column. The column was washed with $Ni^{+2}$ column buffer containing 20 mM imidazole to remove most of the non-specifically bound proteins. Hrad1 eluted from the column with a linear gradient of $Ni^{+2}$ column buffer containing 20 mM to 750 mM imidazole. Fractions of 3.1 ml were collected and assayed by electrophoresis on a 12% SDS-PAGE gel. Fractions containing Hrad1 were pooled and dialyzed against buffer A (10 mM Tris-HCl, pH 7.5, 0.5 mM EDTA, 2mM DTT, 10% glycerol) containing 200 mM NaCl, then against buffer A containing 50 mM NaCl. The protein solution was loaded onto an 8 ml MonoQ (H/H 16/10) column. Hrad1 eluted from the column with a 30 ml gradient of buffer A containing 100 mM to 500 mM NaCl. Fractions of 0.5 ml were collected and assayed by electrophoresis on a 12% SDS-PAGE gel. Hrad1 eluted at 200 mM NaCl. This 12L culture yielded 5 mg of soluble Hrad1 protein that was judged to be 95% pure in a Coomassie-stained SDS-PAGE gel, as shown in FIGS. 6A and 6B.

Example 9

Mapping of HRAD17 on Human Chromosomes

Figure 7:
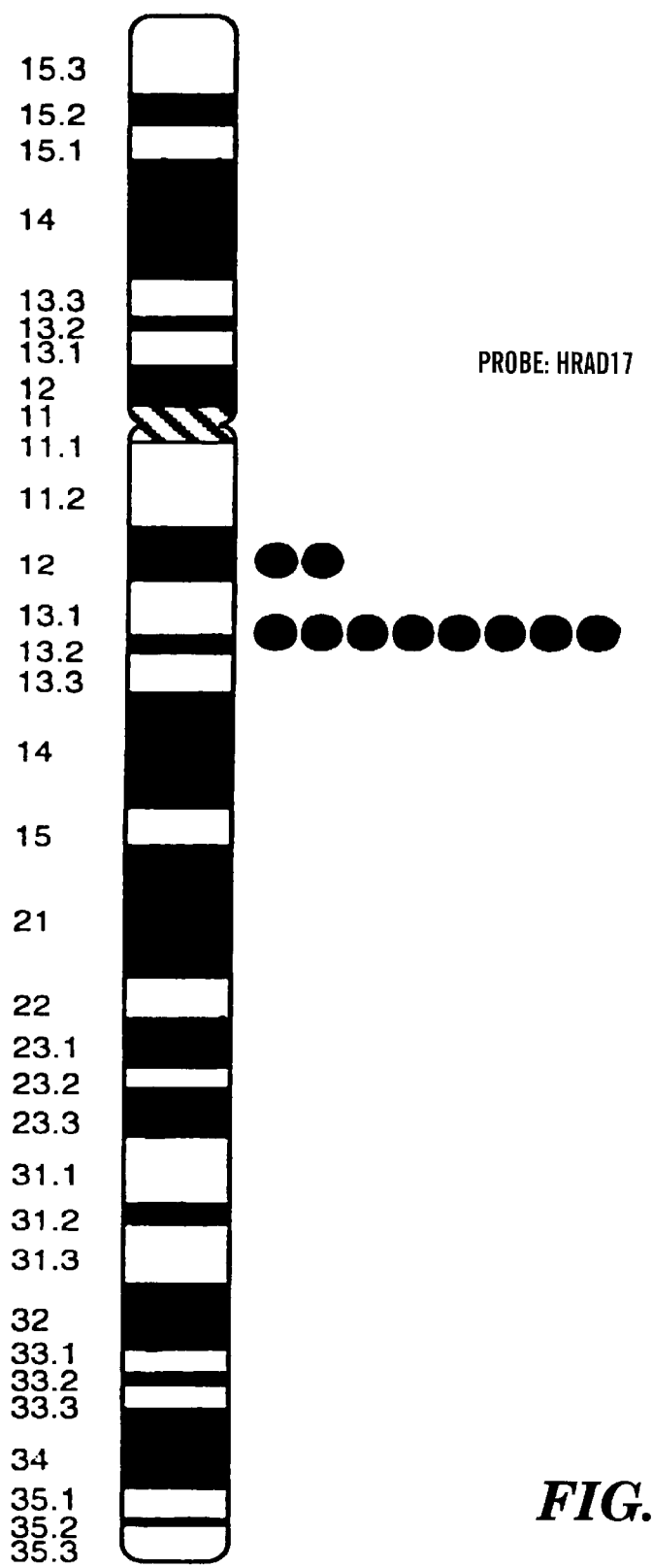
FIG. 7 shows a diagram of the FISH mapping results for HRAD17. Each dot represents a double FISH signal detected on chromosome 5.

Chromosome mapping of HRAD17 was carried out by SeeDNA using fluorescence in situ hybridization (FISH). Heng, H. H. Q., et al., "High Resolution Mapping of Mammalian Genes by in situ Hybridization to Free Chromatin," *Proc. Natl. Acad. Sci. USA*, 89:9509–13 (1992) and Heng, H. H. Q., et al., "Modes of DAPI Banding and Simultaneous in situ Hybridization," *Chromosoma*, 102:325–32 (1993), both of which are incorporated herein by reference. HRAD17 cDNA (clone 586844, 2.5 kilobases) was biotinylated using the BioNick labeling kit (GIBCO/BRL) for use as a probe. The probe hybridized to metaphase chromosomes of human lymphocytes with an efficiency of 73% (among 100 checked mitotic figures, 73 of them showed signals on one pair of the chromosomes). The detailed position was determined based on 10 photographs; genomic HRAD17 is located on human chromosome 5, region q13, as shown in FIG. 7.

Many studies have previously identified human chromosome 5q13 as the location of an unidentified tumor suppressor gene. Translocations, deletions, and inversions involving 5q13 have been found to be associated with hematologic malignancies. Fairman, J., et al., "Translocations and Deletions of 5q13.1 in Myelodysplasia and Acute Myelogenous Leukemia: Evidence for a Novel Critical Locus," *Blood*, 88:2259–66 (1996); Shanske, A. L., et al., "A Myeloproliferative Disorder With Eosinophila Associated With a Unique Translocation (3;5)," *Brit. J. Haematol.*, 95:524–26 (1996); Gogineni, S. K., et al., "A New Translocation, t(5;21) (q13;q22) in Acute Myelogenous Leukemia," *Cancer Genet. Cytogenet.*, 88:167–69 (1996); Morgan, R., et al., "Inversion of Chromosome 5 Long Arm in Region of Cell Growth Gene Cluster in Hematologic Disorders," *Cancer Genet. Cytogenet.*, 32:267–75 (1988), all of which are incorporated herein by reference. Rearrangements of band 5q13 are also associated with chondrosarcomas. Ordnal, C., et al., "Chromosome Aberrations and Cytogenetic Intratumor Heterogeneity in Chondrosarcomas," *J. Cancer Res. Clin. Oncol.*, 120:51–56 (1993); Tarkkanen, M., et al., "Cytogenetic Study of 249 Consecutive Patients Examined for a Bone Tumor," *Cancer Genet. Cytogenet.*, 68:1–21 (1993), both of which are incorporated herein by reference. Losses of 5q13-q21 (Miura, I., et al., "Chromosome Alterations in Human Small Cell Lung Cancer: Frequent Involvement of 5q," Cancer Research, 52:1322–28 (1992), which is incorporated herein by reference) and rearrangement involving 5q13-q132 (Goguel, A. F., et al., "Evolution of Chromosomal Alterations and Biologic Features in Two Small Cell Lung Carcinoma Cell Lines Established From One Patient During the Course of the Disease," *Cancer Genet. Cytogenet.*, 80:47–54 (1995), which is incorporated herein by reference) have been observed in small cell lung cancers. A loss of heterozygosity (LOH) was found at Sq13.1-q21 in ovarian cancer (Tavassoli, M., et al., "Loss of Heterozygosity on Chromosome 5q in Ovarian Cancer is Frequently Accompanied by TP53 Mutation and Identifies a Tumour Suppressor Gene Locus at 5q13.1–21," *Brit. J. Cancer*, 74:115–19 (1996), which is incorporated herein by reference) and a translocation involving 5q13 is a candidate for primary chromosome changes in renal cancer (Berger, C. S., et al., "Chromosomes in Kidney, Ureter, and Bladder Cancer," *Cancer Genet. Cytogenet.*, 23:1–24 (1986), which is incorporated herein by reference). Hrad17 is a candidate for the tumor suppressor gene that has been identified in the 5q13 region.

Example 10

Mapping of HRAD1 on Human Chromosomes

Figure 8:
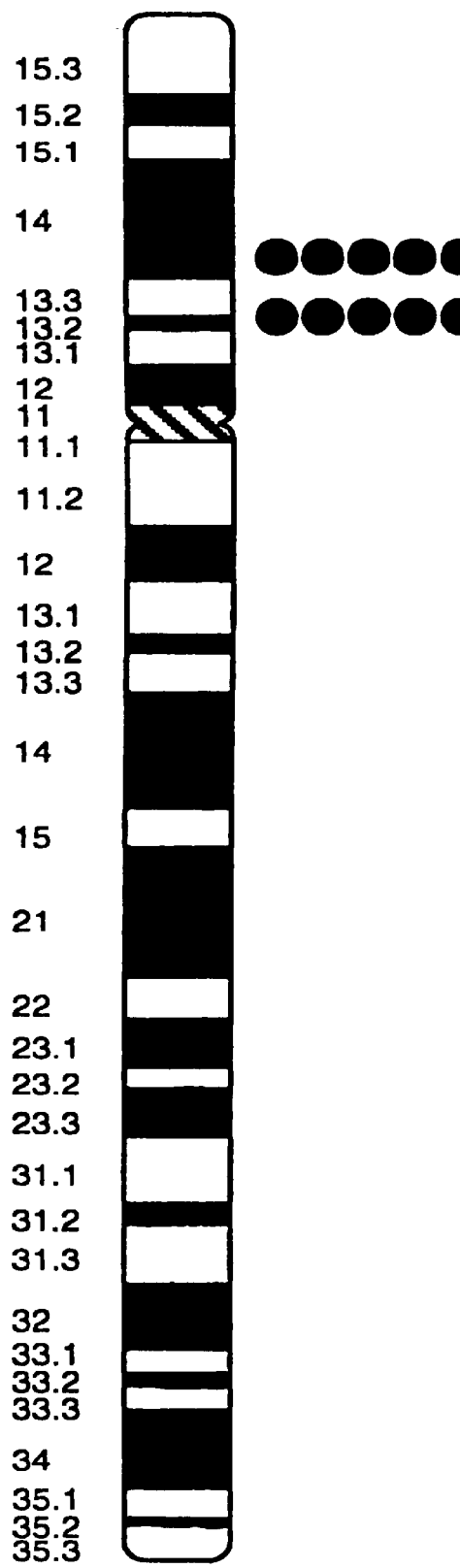
FIG. 8 shows a diagram of the FISH mapping results for HRAD1. Each dot represents a double FISH signal detected on chromsome 5.
Figure 9:
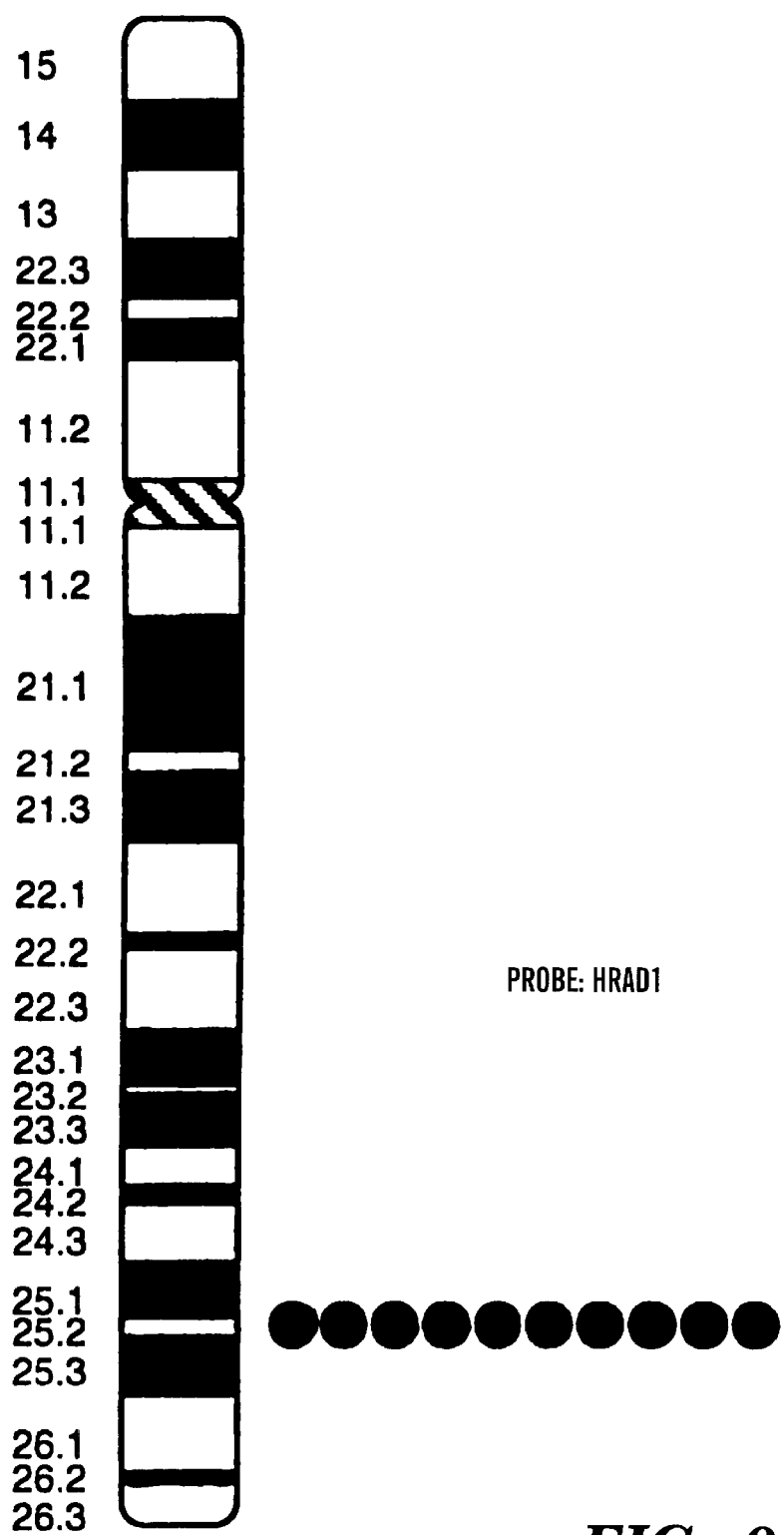
FIG. 9 shows a diagram of the FISH mapping results for the additional locus of HRAD1. Each dot represents a double FISH signal detected on chromosome 10.

Chromosome mapping of HRAD1 was carried out by SeeDNA using fluorescence in situ hybridization. Heng, H. H. Q., et al., "High Resolution Mapping of Mammalian Genes by in situ Hybridization to Free Chromatin," *Proc. Natl. Acad. Sci. USA*, 89:9509–13 (1992); and Heng, H. H. Q., et al., "Modes of DAPI Banding and Simultaneous in situ Hybridization," *Chromosoma*, 102:325–32 (1993), both of which are incorporated herein by reference. HRAD17 cDNA (clone 667461, 1.2 kilobases) was biotinylated using the BioNick labeling kit (GIBCO/BRL) for use as a probe. The probe hybridized to metaphase chromosomes of human lymphocytes with an efficiency of 75% (among 100 checked mitotic figures, 75 of them showed signals on one pair of the chromosomes). The detailed position was determined based on 10 photographs; genomic HRAD1 is located on human chromosome 5, region p14-p13.2, as shown in FIG. 8. One additional locus was detected on chromosome 10, region q25, as shown in FIG. 9. The detection frequency was 45%. Since this frequency was much lower than the frequency for the locus on chromosome 5, it was concluded that the HRAD1 gene resides on chromosome 5, while a related sequence, perhaps a pseudogene, maps to chromosome 10q25.

Human chromosome 5p 13 has been identified previously as the location of an unidentified tumor suppressor gene. Allelic deletion mapping identified a deletion designated del-27 at 5p13-p12 as being associated with small cell lung carcinomas. Wieland, I., et al., "Allelic Deletion Mapping on Chromosome 5 in Human Carcinomas," *Oncogene*, 12:97–102 (1996), which is incorporated herein by reference. Tumor-specific loss of heterozygosity was also detected at del-27 in 10 of 38 (26%) bladder cancers. Bohm, M. et al., "Deletion Analysis at the DEL-27, APC and MTS1 Loci in Bladder Cancer: LOH at the DEL-27 Locus on 5p13-12 is a Prognostic Marker of Tumour Progression," *Int. J. Cancer*, 74:291–95 (1997), which is incorporated herein by reference. Loss of 5p13 is also associated with colon cancer development. Yeatman, T. J., et al., "Identification of Genetic Alterations Associated With the Process of Human Experimental Colon Cancer Liver Metastasis in the Nude Mouse," *Clin. Exn. Metastasis* 14:246–52 (1996), which is incorporated herein by reference. In addition, deletion of 5p13 was identified as causing developmental defects including microcephaly, hypertonia, micrognathia, and mental retardation. Keppen, L. D., et al., "Clinical Phenotype and Molecular Analysis of a Three-Generation Family With an Interstitial Deletion of the Short Arm of Chromosome 5," *Am. J. Med. Genet.*, 44:356–60 (1992), which is incorporated herein by reference. This is reminiscent of the pleiotropic phenotype of ataxia telangiectasia, a multisystem disorder involving ataxia, due to neurodegeneration, telangiectases (patches of dilated blood vessels) in the face, eyes, and ears, and immunodeficiencies. HRAD1 is a candidate for the tumor suppressor gene that resides at 5p13.

Example 11

Mapping of HHUS1 on Human Chromosomes

Figure 10:
FIG. 10 shows a diagram of the FISH mapping results for HHUS1. Each dot represents a double FISH signal detected on chromosome 7.

Chromosome mapping of HHUS1 was carried out by See DNA using fluorescence in situ hybridization (FISH). Heng, H. H. Q., et al., "High Resolution Mapping of Mammalian Genes by in situ Hybridization to Free Chromatin," *Proc. Natl. Acad. Sci. USA*, 89:9509–13 (1992) and Heng, H. H. Q., et al., "Modes of DAPI Banding and Simultaneous in situ Hybridization," *Chromosoma*, 102:325–32 (1993), both of which are incorporated herein by reference. Hhus1 cDNA (clone F1-1279D, 1.8 kilobases) was biotinylated using the BioNick labeling kit (GIBCO/BRL) for use as a probe. The probe hybridized to metaphase chromosomes of human lymphocytes with an efficiency of 67% (among 100 checked mitotic figures, 67 of them showed signals on one pair of the chromosomes). The detailed position was determined based on 10 photographs; HHUS1 is located on human chromosome 7, region p13-p12 (FIG. 10).

Chromosome rearrangements at 7p13, especially translocations, have been noted in non-Hodgkin's lymphoma (Jonveaux, P., et al., "Deletion of (7p13p14) in Non-Hodgkin's Lymphoma," *Cancer Genet. Cytogenet.*, 50:53–56 (1990) and Dyer, M. J. S., et al., "A New Human T-Cell Lymphoma Cell Line (Karpas 384) of the T-Cell Receptor Gamma/Delta Lineage with Translocation t(7:14) (p13;q11.2)," *Leukemia*, 7:1047–53 (1993), both of which are incorporated herein by reference) and acute lymphoblastic leukemia (Uckun, F. M., et al., "Heterogeneity of Cultured Leukemic Lymphoid Progenitor Cells from B Cell Precursor Acute Lymphoblastic Leukemia (ALL) Patients," *J. Clin. Invest.*, 80:639–46 (1987); Uckun, F. M., et al., "Immunophenotype-Karyotype Associations in Human Acute Lymphoblastic Leukemia," *Blood*, 73:271–80 (1989), both of which are incorporated herein by reference). In addition, these translocations occur frequently in the lymphocytes of patients with ataxia-telangiectasia (AT), Nijmegen breakage syndrome (NBS), or related disorders characterized by heightened rates of chromosome breakage. However, in these cases it is felt that the observed chromosome rearrangements are an effect, not a cause, of the syndromes. Conley, M. E., et al., "Chromosomal Breakage Syndrome With Profound Immunodeficiency," *Blood*, 67:1251–56 (1986); Hecht, F., et al., "Chromosome Changes Connect Immunodeficiency and Cancer in Ataxia-Telangiectasia," *Am. J. Pediatr. Hematol. Oncol.*, 9:185–8 (1987); Taalman, R. D. F. M., et al., "Further Delineation of the Nijmegen Breakage Syndrome," *Am. J. Med. Genet.*, 32:425–31 (1989); Barbi, G., et al., "Chromosome Instability and X-Ray Hypersensitivity in a Microcephalic and Growth-Retarded Child," *Am. J. Med. Genet.*, 40:44–50 (1991); Green, A. J., et al., "Severe Microcephaly with Normal Intellectual Development: the Nijmegem Breakage Syndrome," *Arch. Dis. Child.*, 73:431–34 (1995); and Renedo, M., et al., "Cytogenetic and Molecular Studies of Siblings with Ataxia Telangiectasia Followed for 7 Years," *Cancer Genet. Cytogenet.*, 95:178–182 (1997), all of which are incorporated herein by reference. The chromosome rearrangements occur almost exclusively in lymphocytes, primarily at just four sites; 7p13, 7q34, 14q11, and 14q32. These four regions act as though they contain fragile sites limited to lymphocytes. The fragile sites may be the T-cell receptor alpha, beta, and gamma chain and immunoglobulin H genes that map to these sites and undergo recombination during lymphocyte development. Errors in recombination at these loci probably explain the chromosome 7 and 14 rearrangements. Indeed, these rearrangements are not uncommon in normal lymphocytes, occurring with a frequency of $5 \times 10^{-4}$ per metaphase in phytohemagglutinin-stimulated lymphocyte cultures. The consequences of most of these events appear to be benign or of little clinical significance. Dewald, G. W., et al., "T-Lymphocytes with 7;14 Translocations: Frequency of Occurrence, Breakpoints, and Clinical and Biological Significance," *Am. J. Hum. Genet.*, 38:520–32 (1986); Scheres, J. M., et al., "Possible Involvement of Unstable Sites on Chromosomes 7 and 14 in Human Cancer," *Cancer Genet. Cytogenet.*, 19:151–58 (1986); and Hecht, F., et al., "Fragile Sites Limited to Lymphocytes: Molecular Recombination and Malignancy," *Cancer Genet. Cytogenet.*, 26:95–104 (1987b), all of which are incorporated herein by reference.

Due to the high background of benign chromosomal rearrangements at 7p13 in lymphocytes, it is not possible to determine whether potential tumor suppressors for hematologic malignancies lie within this region. However, the region 7p13-p22 has been identified as being rearranged in a number of cases of ovarian cancer (Pejovic, T., "Genetic Changes in Ovarian Cancer," *Ann. Med.*, 27:73–78 (1995), which is hereby incorporated by reference), and so HHUS1 may be a candidate tumor suppressor for ovarian carcinogenesis.

Although the invention has been described in detail for the purposes of illustration, it is understood that such detail is solely for that purpose, and variations can be made therein by those skilled in the art without departing from the spirit and scope of the invention which is defined by the following claims.

What is claimed is:

1. An isolated mammalian DNA molecule
   (i) which encodes a mammalian single strand gap response protein comprising an amino acid sequence of SEQ. ID. No. 4, SEQ. ID. No. 6, SEQ. ID. No. 8, or SEQ. ID. No. 10; or
   (ii) which encodes a mammalian single strand gap response protein and hybridizes, at 42° C. in a hybridization medium which includes 5×SSPE and 50% formamide, to a nucleic acid complementary to a DNA molecule comprising a nucleotide sequence of SEQ. ID. No. 3, SEQ. ID. No. 5, SEQ. ID. No. 7, or SEQ. ID. No. 9.

2. The isolated DNA molecule according to claim 1, wherein the single strand gap response protein is a human protein.

3. The isolated DNA molecule according to claim 2, wherein said DNA molecule encodes a protein comprising an amino acid sequence of SEQ. ID. No. 4 or SEQ. ID. No. 8.

4. The isolated DNA molecule according to claim 3, wherein said DNA molecule comprises a nucleotide sequence of SEQ. ID. No. 3 or SEQ. ID. No. 7.

5. The isolated DNA molecule according to claim 1, wherein the single stand gap response protein is a mouse protein.

6. The isolated DNA molecule according to claim 5, wherein said DNA molecule encodes a protein comprising an amino acid sequence of SEQ. ID. No. 6 or SEQ. ID. No. 10.

7. The isolated DNA molecule according to claim 6, wherein said DNA molecule comprises the nucleotide sequence of SEQ. ID. No. 5 or SEQ. ID. No. 9.

8. An isolated protein or polypeptide encoded by a DNA molecule according to claim 1.

9. The isolated protein or polypeptide according to claim 8, wherein said protein or polypeptide comprises the amino acid sequence of SEQ. ID. No. 4, SEQ. ID. No. 6, SEQ. ID. No. 8, or SEQ. ID. No. 10.

10. A recombinant DNA expression system comprising an expression vector into which is inserted a DNA molecule according to claim 1.

11. The recombinant DNA expression system according to claim 10, wherein said DNA molecule comprises a nucleotide sequence of SEQ. ID. No. 3, SEQ. ID. No. 5, SEQ. ID. No. 7, or SEQ. ID. No. 9.

12. The recombinant DNA expression system according to claim 10, wherein said DNA molecule is inserted into said vector in sense orientation and correct reading frame.

13. A host cell incorporating a DNA molecule according to claim 1, wherein the DNA molecule is heterologous to the host cell.

14. The host cell according to claim 13, wherein said DNA molecule comprises the nucleotide sequence of SEQ. ID. No. 3, SEQ. ID. No. 5, SEQ. ID. No. 7, or SEQ. ID. No. 9.

15. A method of expressing a single strand gap response protein, comprising:
   transforming a host cell in vitro with a recombinant DNA expression system according to claim 10 under conditions effective to achieve expression of the single strand gap response protein in the host cell.

16. A method of detecting in a sample a gene encoding a single strand gap response protein involved in activation of a DNA repair/cell cycle checkpoint pathway, comprising:
   providing an isolated DNA molecule according to claim 1 or a transcript thereof;
   contacting a sample with the isolated DNA molecule or transcript thereof; and
   detecting the presence in the sample of any gene encoding a single strand gap response protein involved in activation of a DNA repair/cell cycle checkpoint pathway using an assay system.

17. The method according to claim 16, wherein said DNA molecule includes a label selected from the group consisting of a radioactive compound, a fluorescent compound, a chemiluminescent compound, and an enzymatic compound.

18. The method according to claim 16, wherein said assay system is selected from the group consisting of a hybridization procedure and a gene amplification procedure.

19. A method of identifying pharmacological agents which disrupt single strand gap response protein activity comprising:

combining a DNA molecule having a single-stranded region, a mammalian single strand gap response protein, and a candidate pharmacological agent as a mixture under conditions effective for the mammalian single strand gap response protein to bind to the DNA molecule in the absence of the candidate pharmacological agent, wherein the mammalian single strand gap response protein is encoded by a DNA molecule which (i) comprises a nucleotide sequence of SEQ. ID. No. 1, SEQ. ID. No. 3, SEQ. ID. No. 5, SEQ. ID. No. 7, or SEQ. ID. No. 9, or (ii) hybridizes, at 42° C. in a hybridization medium including 5×SSPE and 50% formamide, to a nucleic acid complementary to a DNA molecule comprising a nucleotide sequence of SEQ. ID. No. 1, SEQ. ID. No. 3, SEQ. ID. No. 5, SEQ. ID. No. 7, or SEQ. ID. No. 9; and evaluating whether the pharmacological agent inhibits binding of the mammalian single strand gap response protein to the DNA molecule, wherein inhibition of binding indicates the pharmacological agent disrupts activity of the mammalian single strand gap response protein.

20. An isolated Drosophila DNA molecule
   (i) which encodes a *Drosophila melanogaster* single strand gap response protein comprising an amino acid sequence of SEQ. ID. No. 12; or
   (ii) which encodes a Drosophila single strand gap response protein and hybridizes, at 42° C. in a hybridization medium which includes 5×SSPE and 50% formamide, to a nucleic acid complementary to a DNA molecule comprising a nucleotide sequence of SEQ. ID. No. 11.

21. The isolated DNA molecule according to claim 20, wherein said DNA molecule comprises a nucleotide sequence of SEQ. ID. No. 11.

22. An isolated Caenorhabditis DNA molecule
   (i) which encodes a *Caenorhabditis elegans* single strand gap response protein comprising an amino acid sequence of SEQ. ID. No. 14 or SEQ. ID. No. 16; or
   (ii) which encodes a Caenorhabditis single strand gap response protein and hybridizes, at 42° C. in a hybridization medium which includes 5×SSPE and 50% formamide, to a nucleic acid complementary to a DNA molecule comprising a nucleotide sequence of SEQ. ID. No. 13 or SEQ. ID. No. 15.

23. The isolated DNA molecule according to claim 22, wherein said DNA molecule comprises a nucleotide sequence of SEQ. ID. No. 13 or SEQ. ID. No. 15.

* * * * *

SEQUENCE LISTING

<160> NUMBER OF SEQ ID NOS: 27

<210> SEQ ID NO 1
<211> LENGTH: 2013
<212> TYPE: DNA
<213> ORGANISM: Homo sapiens

<400> SEQUENCE: 1

```
atgaatcagg taacagactg ggttgaccca tcatttgatg attttctaga gtgtagtggc      60
gtctctacta ttactgccac atcattaggt gtgaataact caagtcatag aagaaaaaat     120
gggccttcta cattagaaag cagcagattt ccagcgagaa aaagaggaaa tctatcttcc     180
ttagaacaga tttatggttt agaaaattca aaagaatatc tgtctgaaaa tgaaccatgg     240
gtggataaat ataaaccaga aactcagcat gaacttgctg tgcataaaaa gaaaattgaa     300
gaagtcgaaa cctggttaaa agctcaagtt ttagaaaggc aaccaaaaca gggtggatct     360
attttattaa taacaggtcc tcctggatgt ggaaagacaa cgaccttaaa aatactatca     420
aaggagcatg gtattcaagt acaagagtgg attaatccag ttttaccaga cttccaaaaa     480
gatgatttca aggggatgtt taatactgaa tcaagcttcc atatgtttcc ctatcagtct     540
cagatagcag ttttcaaaga gtttctacta agagcgacaa agtataacaa gttacaaatg     600
cttggagatg atctgagaac tgataagaag ataattctgg ttgaagattt acctaaccag     660
```

-continued

| | |
|---|---|
| ttttatcggg attctcatac tttacatgaa gttctaagga agtatgtgag gattggtcga | 720 |
| tgtcctctta tatttataat ctcggacagt ctcagtggag ataataatca aaggttattg | 780 |
| tttcccaaag aaattcagga agagtgttct atctcaaata ttagtttcaa ccctgtggca | 840 |
| ccaacaatta tgatgaaatt tcttaatcga atagtgacta tagaagctaa caagaatgga | 900 |
| ggaaaaatta ctgtccctga caaaacttct ctagagttgc tctgtcaggg atgttctggt | 960 |
| gatatcagaa gtgcaataaa cagcctccag ttttcttctt caaaaggaga aaacaactta | 1020 |
| cggccaagga aaaaggaat gtctttaaaa tcagatgctg tgctgtcaaa atcaaaacga | 1080 |
| agaaaaaaac ctgatagggt ttttgaaaat caagaggtcc aagctattgg tggcaaagat | 1140 |
| gtttctctgt ttctcttcag agctttgggg aaaattctat attgtaaaag agcatcttta | 1200 |
| acagaattag actcacctcg gttgccctct catttatcag aatatgaacg ggatacatta | 1260 |
| cttgttgaac ctgaggaggt agtagaaatg tcacacatgc ctggagactt atttaattta | 1320 |
| tatcttcacc aaaactacat agatttcttc atggaaattg atgatattgt gagagccagt | 1380 |
| gaatttctga gttttgcaga tatcctcagt ggtgactgga atacacgctc tttactcagg | 1440 |
| gaatatagca catctatagc tacgagaggt gtgatgcatt ccaacaaagc ccgaggatat | 1500 |
| gctcattgcc aaggaggagg atcaagtttt cgacccttgc acaaacctca gtggtttcta | 1560 |
| ataaataaaa agtatcggga aaattgcctg gcagcaaaag cacttttttcc tgacttctgc | 1620 |
| ctaccagctt tatgcctcca aactcagcta ttgccatacc ttgctctact aaccattcca | 1680 |
| atgagaaatc aagctcagat ttcttttatc aagatattg aaggctcccc tctgaagcga | 1740 |
| cactttggaa gattgaaaat ggaagccctg actgacaggg aacatggaat gatagaccct | 1800 |
| gacagcggag atgaagccca gcttaatgga ggacattctg cagaggaatc tctgggtgaa | 1860 |
| cccactcaag ccactgtgcc ggaaacctgg tctcttcctt tgagtcagaa tagtgccagt | 1920 |
| gaactgcctg ctagccagcc ccagcccttt tcagcccaag agacatggaa agaaaacata | 1980 |
| ataatagaag actacgagag tgatgggaca tag | 2013 |

<210> SEQ ID NO 2
<211> LENGTH: 670
<212> TYPE: PRT
<213> ORGANISM: Homo sapiens

<400> SEQUENCE: 2

Met Asn Gln Val Thr Asp Trp Val Asp Pro Ser Phe Asp Asp Phe Leu
1               5                   10                  15

Glu Cys Ser Gly Val Ser Thr Ile Thr Ala Thr Ser Leu Gly Val Asn
                20                  25                  30

Asn Ser Ser His Arg Arg Lys Asn Gly Pro Ser Thr Leu Glu Ser Ser
            35                  40                  45

Arg Phe Pro Ala Arg Lys Arg Gly Asn Leu Ser Leu Glu Gln Ile
        50                  55                  60

Tyr Gly Leu Glu Asn Ser Lys Glu Tyr Leu Ser Glu Asn Glu Pro Trp
65                  70                  75                  80

Val Asp Lys Tyr Lys Pro Glu Thr Gln His Glu Leu Ala Val His Lys
                85                  90                  95

Lys Lys Ile Glu Glu Val Glu Thr Trp Leu Lys Ala Gln Val Leu Glu
                100                 105                 110

Arg Gln Pro Lys Gln Gly Gly Ser Ile Leu Leu Ile Thr Gly Pro Pro
            115                 120                 125

Gly Cys Gly Lys Thr Thr Thr Leu Lys Ile Leu Ser Lys Glu His Gly

```
                130              135              140
Ile Gln Val Gln Glu Trp Ile Asn Pro Val Leu Pro Asp Phe Gln Lys
145              150              155              160
Asp Asp Phe Lys Gly Met Phe Asn Thr Glu Ser Ser Phe His Met Phe
                165              170              175
Pro Tyr Gln Ser Gln Ile Ala Val Phe Lys Glu Phe Leu Leu Arg Ala
                180              185              190
Thr Lys Tyr Asn Lys Leu Gln Met Leu Gly Asp Asp Leu Arg Thr Asp
                195              200              205
Lys Lys Ile Ile Leu Val Glu Asp Leu Pro Asn Gln Phe Tyr Arg Asp
210              215              220
Ser His Thr Leu His Glu Val Leu Arg Lys Tyr Val Arg Ile Gly Arg
225              230              235              240
Cys Pro Leu Ile Phe Ile Ile Ser Asp Ser Leu Ser Gly Asp Asn Asn
                245              250              255
Gln Arg Leu Leu Phe Pro Lys Glu Ile Gln Glu Glu Cys Ser Ile Ser
                260              265              270
Asn Ile Ser Phe Asn Pro Val Ala Pro Thr Ile Met Met Lys Phe Leu
                275              280              285
Asn Arg Ile Val Thr Ile Glu Ala Asn Lys Asn Gly Gly Lys Ile Thr
                290              295              300
Val Pro Asp Lys Thr Ser Leu Glu Leu Leu Cys Gln Gly Cys Ser Gly
305              310              315              320
Asp Ile Arg Ser Ala Ile Asn Ser Leu Gln Phe Ser Ser Ser Lys Gly
                325              330              335
Glu Asn Asn Leu Arg Pro Arg Lys Lys Gly Met Ser Leu Lys Ser Asp
                340              345              350
Ala Val Leu Ser Lys Ser Lys Arg Arg Lys Pro Asp Arg Val Phe
                355              360              365
Glu Asn Gln Glu Val Gln Ala Ile Gly Gly Lys Asp Val Ser Leu Phe
                370              375              380
Leu Phe Arg Ala Leu Gly Lys Ile Leu Tyr Cys Lys Arg Ala Ser Leu
385              390              395              400
Thr Glu Leu Asp Ser Pro Arg Leu Pro Ser His Leu Ser Glu Tyr Glu
                405              410              415
Arg Asp Thr Leu Leu Val Glu Pro Glu Val Val Glu Met Ser His
                420              425              430
Met Pro Gly Asp Leu Phe Asn Leu Tyr Leu His Gln Asn Tyr Ile Asp
                435              440              445
Phe Phe Met Glu Ile Asp Ile Val Arg Ala Ser Glu Phe Leu Ser
                450              455              460
Phe Ala Asp Ile Leu Ser Gly Asp Trp Asn Thr Arg Ser Leu Leu Arg
465              470              475              480
Glu Tyr Ser Thr Ser Ile Ala Thr Arg Gly Val Met His Ser Asn Lys
                485              490              495
Ala Arg Gly Tyr Ala His Cys Gln Gly Gly Ser Ser Phe Arg Pro
                500              505              510
Leu His Lys Pro Gln Trp Phe Leu Ile Asn Lys Lys Tyr Arg Glu Asn
                515              520              525
Cys Leu Ala Ala Lys Ala Leu Phe Pro Asp Phe Cys Leu Pro Ala Leu
                530              535              540
Cys Leu Gln Thr Gln Leu Leu Pro Tyr Leu Ala Leu Leu Thr Ile Pro
545              550              555              560
```

```
Met Arg Asn Gln Ala Gln Ile Ser Phe Ile Gln Asp Ile Gly Arg Leu
                565                 570                 575
Pro Leu Lys Arg His Phe Gly Arg Leu Lys Met Glu Ala Leu Thr Asp
            580                 585                 590
Arg Glu His Gly Met Ile Asp Pro Asp Ser Gly Asp Glu Ala Gln Leu
        595                 600                 605
Asn Gly Gly His Ser Ala Glu Glu Ser Leu Gly Glu Pro Thr Gln Ala
    610                 615                 620
Thr Val Pro Glu Thr Trp Ser Leu Pro Leu Ser Gln Asn Ser Ala Ser
625                 630                 635                 640
Glu Leu Pro Ala Ser Gln Pro Gln Pro Phe Ser Ala Gln Gly Asp Met
                645                 650                 655
Glu Glu Asn Ile Ile Ile Glu Asp Tyr Glu Ser Asp Gly Thr
                660                 665                 670

<210> SEQ ID NO 3
<211> LENGTH: 849
<212> TYPE: DNA
<213> ORGANISM: Homo sapiens

<400> SEQUENCE: 3
atgccccttc tgacccaaca gatccaagac gaggatgatc agtacagcct tgtggccagc      60
cttgacaacg ttaggaatct ctccactatc ttgaaagcta ttcatttccg agaacatgcc     120
acgtgtttcg caactaaaaa tggtatcaaa gtaacagtgg aaaatgcaaa gtgtgtgcaa     180
gcaaatgctt ttattcaggc tggaatattt caggagttta agttcaggaa agagtctgtt     240
acttttcgaa ttaatttaac tgtccttta gactgtttat ctattttgg atcaagtcct      300
atgccaggga ctttaactgc acttcgaatg tgttaccaag ttatggtta cctttgatg      360
ctgttcctgg aagaaggagg agtggtgaca gtctgcaaaa tcaatacaca ggaacctgag     420
gagaccctgg actttgattt ctgcagcacc aatgttatta ataaaattat tctgcagtca     480
gagggggctcc gtgaagcatt ttctgaattg gatatgacga gtgaagtcct acaaattacc     540
atgtctcctg acaagcctta tttcaggtta tctactttg gaaatgcagg aagttcccac     600
cttgactatc ccaaagattc tgatttgatg gaagcatttc attgtaatca gacccaagtc     660
aacagataca gatttccctt actgaaaccc tctacaaagg cattagtcct atcttgtaag     720
gtatctattc ggacagataa cagaggcttc ctttcattac agtatatgat tagaaaatgaa     780
gatggacaaa tatgttttgt ggaatattac tgctgccctg atgaagaagt tcctgaatct     840
gagtcttga                                                            849

<210> SEQ ID NO 4
<211> LENGTH: 282
<212> TYPE: PRT
<213> ORGANISM: Homo sapiens

<400> SEQUENCE: 4

Met Pro Leu Leu Thr Gln Gln Ile Gln Asp Glu Asp Asp Gln Tyr Ser
  1               5                  10                  15
Leu Val Ala Ser Leu Asp Asn Val Arg Asn Leu Ser Thr Ile Leu Lys
             20                  25                  30
Ala Ile His Phe Arg Glu His Ala Thr Cys Phe Ala Thr Lys Asn Gly
         35                  40                  45
Ile Lys Val Thr Val Glu Asn Ala Lys Cys Val Gln Ala Asn Ala Phe
     50                  55                  60
```

-continued

```
Ile Gln Ala Gly Ile Phe Gln Glu Phe Lys Val Gln Glu Glu Ser Val
 65                  70                  75                  80

Thr Phe Arg Ile Asn Leu Thr Val Leu Leu Asp Cys Leu Ser Ile Phe
                 85                  90                  95

Gly Ser Ser Pro Met Pro Gly Thr Leu Thr Ala Leu Arg Met Cys Tyr
            100                 105                 110

Gln Gly Tyr Gly Tyr Pro Leu Met Leu Phe Leu Glu Glu Gly Gly Val
        115                 120                 125

Val Thr Val Cys Lys Ile Asn Thr Gln Glu Pro Glu Thr Leu Asp
    130                 135                 140

Phe Asp Phe Cys Ser Thr Asn Val Ile Asn Lys Ile Ile Leu Gln Ser
145                 150                 155                 160

Glu Gly Leu Arg Glu Ala Phe Ser Glu Leu Asp Met Thr Ser Glu Val
                165                 170                 175

Leu Gln Ile Thr Met Ser Pro Asp Lys Pro Tyr Phe Arg Leu Ser Thr
            180                 185                 190

Phe Gly Asn Ala Gly Ser Ser His Leu Asp Tyr Pro Lys Asp Ser Asp
        195                 200                 205

Leu Met Glu Ala Phe His Cys Asn Gln Thr Gln Val Asn Arg Tyr Lys
    210                 215                 220

Ile Ser Leu Leu Lys Pro Ser Thr Lys Ala Leu Val Leu Ser Cys Lys
225                 230                 235                 240

Val Ser Ile Arg Thr Asp Asn Arg Gly Phe Leu Ser Leu Gln Tyr Met
                245                 250                 255

Ile Arg Asn Glu Asp Gly Gln Ile Cys Phe Val Glu Tyr Tyr Cys Cys
            260                 265                 270

Pro Asp Glu Glu Val Pro Glu Ser Glu Ser
        275                 280
```

<210> SEQ ID NO 5
<211> LENGTH: 843
<212> TYPE: DNA
<213> ORGANISM: Mus musculus

<400> SEQUENCE: 5

```
atgcctctcc taacccagta caatgaagag gagtacgaac agtactgctt agtggccagc     60
cttgacaacg ttaggaatct cttcactgtc ttgaaagcca ttcatttcag agaacacgcc    120
acgtgttttg ctaccaaaaa cggaatcaag gttacagtgg agaatgcaaa gtgtgtgcaa    180
gcaaatgcct ttattcaggc tgacgtgttt caggaatttg tcattcagga agaatctgtt    240
acttttcgaa ttaacttaac tatccttttta gactgtttat ctattttttgg atcaagtcct    300
acaccaggga ctttgactgc gcttcggatg tgttaccaag ttatggtca cccactgatg    360
ctatttctag aagaaggagg agtggtgacg gtctgcaaaa ttaccactca ggagcctgag    420
gagacactgg atttttgattt ctgcagcacc aatgttatga ataaaattat cctgcagtca    480
gagggggctcc gggaagcctt ttctgagctg acatgacga gtgatgtcct acagatcact    540
gtgtctcctg acaagcccta tttcaggttg tctacttttg gaaatgcagg aaactcccat    600
cttgactatc ccaaagattc cgacttggtg gaagcctttc actgtgataa gacccaggtc    660
aacagataca gctgtcgct actgaagccc tctacaaagg cactagcttt atcctgtaaa    720
gtgtctatcc ggacagataa ccgaggcttc ctctccttac agtacatgat agaaatgaa    780
gatgggcaga tatgttttgt ggaatattac tgctgccctg atgaagaagt tcctgagtct    840
``` tga                                                                    843

<210> SEQ ID NO 6
<211> LENGTH: 280
<212> TYPE: PRT
<213> ORGANISM: Mus musculus

<400> SEQUENCE: 6

Met Pro Leu Leu Thr Gln Tyr Asn Glu Glu Glu Tyr Glu Gln Tyr Cys
 1               5                  10                  15

Leu Val Ala Ser Leu Asp Asn Val Arg Asn Leu Phe Thr Val Leu Lys
            20                  25                  30

Ala Ile His Phe Arg Glu His Ala Thr Cys Phe Ala Thr Lys Asn Gly
        35                  40                  45

Ile Lys Val Thr Val Glu Asn Ala Lys Cys Val Gln Ala Asn Ala Phe
    50                  55                  60

Ile Gln Ala Asp Val Phe Gln Glu Phe Val Ile Gln Glu Glu Ser Val
65                  70                  75                  80

Thr Phe Arg Ile Asn Leu Thr Ile Leu Leu Asp Cys Leu Ser Ile Phe
                85                  90                  95

Gly Ser Ser Pro Thr Pro Gly Thr Leu Thr Ala Leu Arg Met Cys Tyr
            100                 105                 110

Gln Gly Tyr Gly His Pro Leu Met Leu Phe Leu Glu Glu Gly Gly Val
        115                 120                 125

Val Thr Val Cys Lys Ile Thr Thr Gln Glu Pro Glu Glu Thr Leu Asp
    130                 135                 140

Phe Asp Phe Cys Ser Thr Asn Val Met Asn Lys Ile Ile Leu Gln Ser
145                 150                 155                 160

Glu Gly Leu Arg Glu Ala Phe Ser Glu Leu Asp Met Thr Gly Asp Val
                165                 170                 175

Leu Gln Ile Thr Val Ser Pro Asp Lys Pro Tyr Phe Arg Leu Ser Thr
            180                 185                 190

Phe Gly Asn Ala Gly Asn Ser His Leu Asp Tyr Pro Lys Asp Ser Asp
        195                 200                 205

Leu Val Glu Ala Phe His Cys Asp Lys Thr Gln Val Asn Arg Tyr Lys
    210                 215                 220

Leu Ser Leu Leu Lys Pro Ser Thr Lys Ala Leu Ala Leu Ser Cys Lys
225                 230                 235                 240

Val Ser Ile Arg Thr Asp Asn Arg Gly Phe Leu Ser Leu Gln Tyr Met
                245                 250                 255

Ile Arg Asn Glu Asp Gly Gln Ile Cys Phe Val Glu Tyr Tyr Cys Cys
            260                 265                 270

Pro Asp Glu Glu Val Pro Glu Ser
        275                 280

<210> SEQ ID NO 7
<211> LENGTH: 843
<212> TYPE: DNA
<213> ORGANISM: Homo sapiens

<400> SEQUENCE: 7
atgaagtttc gggccaagat cgtggacggg gcctgtctga accacttcac acgaatcagt      60
aacatgatag ccaagcttgc caaaacctgc accctccgca tcagccctga taagcttaac     120
ttcatccttt gtgacaagct ggctaatgga ggagtgagca tgtggtgtga gctggaacag     180
gagaacttct tcaacgaatt tcaaatggag ggtgtctctg cagaaaacaa tgagatttat     240

```
ttagagctaa catcggaaaa cttatctcga gccttgaaga ctgcccagaa tgccagggct      300
ttgaaaatca aactgactaa taaacacttt ccctgcctca cggtctccgt ggagctgtta      360
tctatgtcaa gcagtagccg cattgtgacc catgacatcc ccataaaggt gattcctagg      420
aaattgtgga aggacttaca agaaccggtg gtcccagatc ctgatgttag tatttattta      480
ccagtcttga agactatgaa gagtgttgtg gaaaaaatga aaacatcag caatcacctt       540 gttattgaag caaacctaga tggagaattg aatttgaaaa tagaaactga attagtatgt      600
gttacaactc attttaaaga tcttggaaat cctccattag cctctgaaag cacccatgag      660
gacagaaacg tggaacacat ggctgaagtg cacatagata ttaggaagct cctacagttt      720
cttgctggac aacaagtaaa tcccacaaag gccttatgca atattgtgaa taacaagatg      780
gtgcattttg atctgcttca tgaagacgtg tcccttcagt atttcatccc tgcgctgtcc      840
tag                                                                    843
```

<210> SEQ ID NO 8
<211> LENGTH: 280
<212> TYPE: PRT
<213> ORGANISM: Homo sapiens

<400> SEQUENCE: 8

```
Met Lys Phe Arg Ala Lys Ile Val Asp Gly Ala Cys Leu Asn His Phe
  1               5                  10                  15

Thr Arg Ile Ser Asn Met Ile Ala Lys Leu Ala Lys Thr Cys Thr Leu
             20                  25                  30

Arg Ile Ser Pro Asp Lys Leu Asn Phe Ile Leu Cys Asp Lys Leu Ala
         35                  40                  45

Asn Gly Gly Val Ser Met Trp Cys Glu Leu Glu Gln Glu Asn Phe Phe
     50                  55                  60

Asn Glu Phe Gln Met Glu Gly Val Ser Ala Glu Asn Asn Glu Ile Tyr
 65                  70                  75                  80

Leu Glu Leu Thr Ser Glu Asn Leu Ser Arg Ala Leu Lys Thr Ala Gln
                 85                  90                  95

Asn Ala Arg Ala Leu Lys Ile Lys Leu Thr Asn Lys His Phe Pro Cys
            100                 105                 110

Leu Thr Val Ser Val Glu Leu Leu Ser Met Ser Ser Ser Arg Ile
            115                 120                 125

Val Thr His Asp Ile Pro Ile Lys Val Ile Pro Arg Lys Leu Trp Lys
        130                 135                 140

Asp Leu Gln Glu Pro Val Val Pro Asp Pro Asp Val Ser Ile Tyr Leu
145                 150                 155                 160

Pro Val Leu Lys Thr Met Lys Ser Val Val Glu Lys Met Lys Asn Ile
                165                 170                 175

Ser Asn His Leu Val Ile Glu Ala Asn Leu Asp Gly Glu Leu Asn Leu
            180                 185                 190

Lys Ile Glu Thr Glu Leu Val Cys Val Thr Thr His Phe Lys Asp Leu
        195                 200                 205

Gly Asn Pro Pro Leu Ala Ser Glu Ser Thr His Glu Asp Arg Asn Val
    210                 215                 220

Glu His Met Ala Glu Val His Ile Asp Ile Arg Lys Leu Leu Gln Phe
225                 230                 235                 240

Leu Ala Gly Gln Gln Val Asn Pro Thr Lys Ala Leu Cys Asn Ile Val
                245                 250                 255
```

Asn Asn Lys Met Val His Phe Asp Leu Leu His Glu Asp Val Ser Leu
        260                 265                 270
Gln Tyr Phe Ile Pro Ala Leu Ser
        275                 280

<210> SEQ ID NO 9
<211> LENGTH: 846
<212> TYPE: DNA
<213> ORGANISM: Mus musculus

<400> SEQUENCE: 9

```
atgaagtttc gcgccaagat cgtggacctg gcttgtctga atcatttcac acgagtcagt      60
aacatgatag ccaagcttgc caaaacctgc accctccgca tcagcccgga gaagctgaac     120
ttcatcctgt gcgacaagct ggccagtgga ggcgtgagca tgtggtgtga gctggagcag     180
gagaactttt ttagtgaatt tcaaatggaa ggagtctctg aagaaaacaa cgagatttat     240
ttagaattaa cgtcggaaaa cttatctcga gccttgaaaa ctgcccagaa ctccagagcc     300
ttgaaaatca agctgactaa caaacacttt ccctgtctta ccgtgtctgt agagctgcag     360
gtgtcttcat cgagcagcag cagaatcgtg gtgcatgata tccccataaa ggttcttccg     420
agaagactgt ggaaggactt acaagaaccc tccatcccag actgtgatgt cagtatttgc     480
ttaccagcct tgaagatgat gaagagtgtt gtggaaaaaa tgagaaacat cagcaatcag     540
cttgtgattg aagcaaacct aaagggagaa ttaaacctaa agatagaaac tgagttagtg     600
tgtgtgacta ctcattttaa ggatcttgaa aaccctctat accctctga cagtgtctct      660
caaaacagac acccagaaga catggccaag gtgcacattg acataaagaa actcctccag     720
tttcttgccg acagcaagt gactcccacc aaggcagtgt gcaatattgt gaataacaga     780
actgttcatt ttgatttgct cctggaagac gtctcccttc agtatttcat cccagccttg     840
tcctag                                                                846
```

<210> SEQ ID NO 10
<211> LENGTH: 281
<212> TYPE: PRT
<213> ORGANISM: Mus musculus

<400> SEQUENCE: 10

Met Lys Phe Arg Ala Lys Ile Val Asp Leu Ala Cys Leu Asn His Phe
 1               5                  10                  15
Thr Arg Val Ser Asn Met Ile Ala Lys Leu Ala Lys Thr Cys Thr Leu
                20                  25                  30
Arg Ile Ser Pro Glu Lys Leu Asn Phe Ile Leu Cys Asp Lys Leu Ala
            35                  40                  45
Ser Gly Gly Val Ser Met Trp Cys Glu Leu Glu Gln Glu Asn Phe Phe
        50                  55                  60
Ser Glu Phe Gln Met Glu Gly Val Ser Glu Glu Asn Asn Glu Ile Tyr
 65                  70                  75                  80
Leu Glu Leu Thr Ser Glu Asn Leu Ser Arg Ala Leu Lys Thr Ala Gln
                85                  90                  95
Asn Ser Arg Ala Leu Lys Ile Lys Leu Thr Asn Lys His Phe Pro Cys
            100                 105                 110
Leu Thr Val Ser Val Glu Leu Gln Val Ser Ser Ser Ser Ser Ser Arg
        115                 120                 125
Ile Val Val His Asp Ile Pro Ile Lys Val Leu Pro Arg Arg Leu Trp
    130                 135                 140

-continued

```
Lys Asp Leu Gln Glu Pro Ser Ile Pro Asp Cys Asp Val Ser Ile Cys
145                 150                 155                 160

Leu Pro Ala Leu Lys Met Met Lys Ser Val Val Glu Lys Met Arg Asn
            165                 170                 175

Ile Ser Asn Gln Leu Val Ile Glu Ala Asn Leu Lys Gly Glu Leu Asn
        180                 185                 190

Leu Lys Ile Glu Thr Glu Leu Val Cys Val Thr Thr His Phe Lys Asp
    195                 200                 205

Leu Glu Asn Pro Leu Leu Pro Ser Asp Ser Val Ser Gln Asn Arg His
210                 215                 220

Pro Glu Asp Met Ala Lys Val His Ile Asp Ile Lys Lys Leu Leu Gln
225                 230                 235                 240

Phe Leu Ala Gly Gln Gln Val Thr Pro Thr Lys Ala Val Cys Asn Ile
            245                 250                 255

Val Asn Asn Arg Thr Val His Phe Asp Leu Leu Leu Glu Asp Val Ser
        260                 265                 270

Leu Gln Tyr Phe Ile Pro Ala Leu Ser
    275                 280
```

<210> SEQ ID NO 11
<211> LENGTH: 1563
<212> TYPE: DNA
<213> ORGANISM: Drosophila melanogaster

<400> SEQUENCE: 11

```
atgaacttga ccaccagtcc tgctccttcg aatccacgc ctgcgaagcg cacaagaagt      60
gcaagcaatg tgagcagctc cagagtatcg aggtcgagaa ctccaagcat aaatacaaag    120
ccaatacaga ttccggacgt ggactcagtc gatcttactg ccatggatga tgaccaggat    180
gcggacatca ctgtgccacc gccagaagtc aaagaaaact ggatggaaag ctttgagcca    240
gccaccagcg acgatttggc ggtgcatcca agaaggtcg gagaactacg cgattggctg     300
cgtcactgcg aagcggtgcg caagaagttc ccggctcaaa tgtgtctact accgggccc     360
actggtgctg gcaaaaccac cacgttgcga gtcctggcca aggagttcgg ctaccagctg    420
caggagtgga tcaatcctat cgattgtgag gtggtcaaca ccttgggtga tcaaacgact    480
ggcgcctcct atgtgggctc ccatctggag cctttaaaa gctttctgct ccgtgcctcg    540
cgatacaaat ccttgctgga ctcgcaaaat aagagactgc ttcttgtcga ggactttccc    600
aacgtcctgc tcagcgataa ggaggtcaac tttgaagagt actagaagaa gtacacggcg    660
tatggcaaat ctccccctgg tgttcatcgtt gccgatgcca atctcgagg attgaatatc    720
agctaccgcc tctttccaga ccaactgaag gccaaacatc gcatcgagca catcagttt    780
aatgctattg catctacaat catgcaaaag tcaatgaaaa ccttctgctc cgtaatgcag    840
cagaataaag ctacttacaa ggtgccctcg accgctgttg ttgactcaat agttgtcggt    900
gcccagggcg acataagaaa tgcgttaatt aatttacatt tgagctcttt aagggagtt    960
tccagcatgc cgaccaaaca gctaaatgtc agtgtgtccg caaaggtcg taagaagaa   1020
atgcaaagta ctttaaagtc aattggtaga gatgaatcaa ttactctgat gcacgcactt  1080
ggaagagtat taaatcctaa gtttaatgag acaaaaacta tgttacacag cccggaggaa  1140
ataaccgaag cctttaatac agagcccagg aattttgtga attttgtata tgccaactat  1200
ctgccgcatt ttaaggaaat cgatgatgtc gtgaccgcca taatgacttt gggcctatca  1260
gattgcatgc tcaacgagta cagagatgat aatttgtctg tgatgggctt aaacgttgcc  1320
```

-continued

```
atacgaggag ttatgatgtc caatacgtgc cctgtcagcg gatggatgcc tgttcgagga      1380
cccaagcgaa tcaatataca gccacaggca actttggccg aacaaagact ggtgggtgtg      1440
ggctacgcgg gcattgccag gacgctctac gccacggagt acagctcatt agttaagtta      1500
atagcaggca agcctgtgga tactacttca agccaaagca cagactcaaa acaagacttt      1560
tag                                                                     1563
```

<210> SEQ ID NO 12
<211> LENGTH: 520
<212> TYPE: PRT
<213> ORGANISM: Drosophila melanogaster

<400> SEQUENCE: 12

```
Met Asn Leu Thr Thr Ser Pro Ala Pro Ser Glu Ser Thr Pro Ala Lys
  1               5                  10                  15

Arg Thr Arg Ser Ala Ser Asn Val Ser Ser Ser Arg Val Ser Arg Ser
             20                  25                  30

Arg Thr Pro Ser Ile Asn Thr Lys Pro Ile Gln Ile Pro Asp Val Asp
         35                  40                  45

Ser Val Asp Leu Thr Ala Met Asp Asp Gln Asp Ala Asp Ile Thr
     50                  55                  60

Val Pro Pro Glu Val Lys Glu Asn Trp Met Glu Ser Phe Glu Pro
 65                  70                  75                  80

Ala Thr Ser Asp Asp Leu Ala Val His Pro Lys Lys Val Gly Glu Leu
                 85                  90                  95

Arg Asp Trp Leu Arg His Cys Glu Ala Val Arg Lys Lys Phe Pro Ala
            100                 105                 110

Gln Met Cys Leu Leu Thr Gly Pro Thr Gly Ala Gly Lys Thr Thr Thr
        115                 120                 125

Leu Arg Val Leu Ala Lys Glu Phe Gly Tyr Gln Leu Gln Glu Trp Ile
    130                 135                 140

Asn Pro Ile Asp Cys Glu Val Val Asn Thr Leu Gly Asp Gln Thr Thr
145                 150                 155                 160

Gly Ala Ser Tyr Val Gly Ser His Leu Glu Ala Phe Lys Ser Phe Leu
                165                 170                 175

Leu Arg Ala Ser Arg Tyr Lys Ser Leu Leu Asp Ser Gln Asn Lys Arg
            180                 185                 190

Leu Leu Leu Val Glu Asp Phe Pro Asn Val Leu Leu Ser Asp Lys Glu
        195                 200                 205

Val Asn Phe Glu Glu Leu Leu Glu Glu Tyr Thr Ala Tyr Gly Lys Ser
    210                 215                 220

Pro Leu Val Phe Ile Val Ala Asp Ala Lys Ser Arg Gly Leu Asn Ile
225                 230                 235                 240

Ser Tyr Arg Leu Phe Pro Asp Gln Leu Lys Ala Lys His Arg Ile Glu
                245                 250                 255

His Ile Ser Phe Asn Ala Ile Ala Ser Thr Ile Met Gln Lys Ser Met
            260                 265                 270

Lys Thr Phe Cys Ser Val Met Gln Gln Asn Lys Ala Thr Tyr Lys Val
        275                 280                 285

Pro Ser Thr Ala Val Val Asp Ser Ile Val Val Gly Ala Gln Gly Asp
    290                 295                 300

Ile Arg Asn Ala Leu Ile Asn Leu His Leu Ser Ser Leu Lys Gly Val
305                 310                 315                 320

Ser Ser Met Pro Thr Lys Gln Leu Asn Val Ser Val Ser Ala Lys Gly
```

```
                      325                 330                 335
Arg Lys Lys Lys Met Gln Ser Thr Leu Lys Ser Ile Gly Arg Asp Glu
                340                 345                 350

Ser Ile Thr Leu Met His Ala Leu Gly Arg Val Leu Asn Pro Lys Phe
            355                 360                 365

Asn Glu Asp Lys Thr Met Leu His Ser Pro Glu Glu Ile Thr Glu Ala
        370                 375                 380

Phe Asn Thr Glu Pro Arg Asn Phe Val Asn Phe Val Tyr Ala Asn Tyr
385                 390                 395                 400

Leu Pro His Phe Lys Glu Ile Asp Asp Val Thr Ala Ile Asn Asp
                405                 410                 415

Leu Gly Leu Ser Asp Cys Met Leu Asn Glu Tyr Arg Asp Asp Asn Leu
            420                 425                 430

Ser Val Met Gly Leu Asn Val Ala Ile Arg Gly Val Met Met Ser Asn
        435                 440                 445

Thr Cys Pro Val Ser Gly Trp Met Pro Val Arg Gly Pro Lys Arg Ile
        450                 455                 460

Asn Ile Gln Pro Gln Ala Thr Leu Ala Glu Gln Arg Leu Val Gly Val
465                 470                 475                 480

Gly Tyr Ala Gly Ile Ala Arg Thr Leu Tyr Ala Thr Glu Tyr Ser Ser
                485                 490                 495

Leu Val Lys Leu Ile Ala Gly Lys Pro Val Asp Thr Thr Ser Ser Gln
            500                 505                 510

Ser Thr Asp Ser Lys Gln Asp Phe
        515                 520

<210> SEQ ID NO 13
<211> LENGTH: 1545
<212> TYPE: DNA
<213> ORGANISM: Caenorhabditis elegans

<400> SEQUENCE: 13
atgaaagccg ctgaacacga tttgctcaca attgagcttg ctccacggcg acgagatgag      60
ctccaaatcc acaataaaaa gattgcagag gtcgatcatt ggctcaaaaa tgtattttct     120
gagtcaaaca agcagctagg agtgatgtac ctcacaggac cagctggctc gggcaaatcg     180
acgactgtcg aagtgatgtg cacagagcag aatatcgaaa tcatcgaata ttcgccagaa     240
tatcttcaca atgaagattt cgagtgtgaa agccggatt tcacccagct gcggaggttt     300
ttgttgcgga gacatggaag cttgcggggt ggtggcttga aaaagcggct tcttctcgtc     360
acagagctgc ctgatcaagc ttatagtgat gctgagaagt tcgagaaga tttgtcagaa     420 gttctgcaac atatttggca tcccgtgata ttctgcctca cgaatagtat tgcatgctgg     480
aatttgaacc ctgatcgatt gtttaccaag gactttaaca ttatgaatgg aatagataca     540
gtaacattca acccagttgc tgactccttc atgaaaaaag cactcgtccg cgcttcaaac     600
tgcctgagct ccccactatc cgatgcaaag ctgaatgtga tcggagagga agctggaggc     660
gatttgagaa tcgctatgaa tatgttacag atgaattcga ttggaccgaa tgctgataga     720
agaagtggaa atagtgtgat atgtgcatcg aaagcgaatc gagaagaagc ttttcatatg     780
attgggcgaa ttttatacgc gaaacgtgtc aatccgaatg ttccgaagcc gagtcgtttc     840
tcgaagcgaa ggcggaagtc tgcaccgatt ccggagccgc tagtgagaac agagctggag     900
catgacccga ctgatattat tacaatgtcg agtatgactt ctgagaagct tctcgacttt     960
ctatttcaaa atgagcccat cttctgctcg aatatatcca aatatcgcta cgtcgcggag    1020
```

-continued

```
actttttcga tgtgtgactt tttaaccgga gactggacga cccgaaaatc tctgccagaa    1080
gattacgtgg cacagatggc tacacgttcg gtgatgtgga ataactacaa agaacctcgc    1140
ccgggaacat tattcgcagt cggacgtccg ttaagaagct cactgaaaaa acacacggct    1200
cgaacgaaat tggaattgca aagacttccg atgattggtg ccaaggatta tgctgctcta    1260
acatgtccgt atataacaat catcaaggat attatcgatc cgcagagaat cgagtatttc    1320
ctctcgagac ccatggatat caactggcaa tggggaaatg ataaaatcga ggagcattta    1380
gagaaacagt atgccctaga ctacaaagga cgtaaaaaac accgtcttcc ccttcataag    1440
gcaccgaagc cttccggaaa gattatcgaa gtggtggatt tggaagagga agaggaaaag    1500
ttcacaatcg aggagtccag tgacgattct tttgaagaat tttga                    1545
```

<210> SEQ ID NO 14
<211> LENGTH: 514
<212> TYPE: PRT
<213> ORGANISM: Caenorhabditis elegans

<400> SEQUENCE: 14

```
Met Lys Ala Ala Glu His Asp Leu Leu Thr Ile Glu Leu Ala Pro Arg
 1               5                  10                  15

Arg Arg Asp Glu Leu Gln Ile His Asn Lys Lys Ile Ala Glu Val Asp
             20                  25                  30

His Trp Leu Lys Asn Val Phe Ser Glu Ser Asn Lys Gln Leu Gly Val
         35                  40                  45

Met Tyr Leu Thr Gly Pro Ala Gly Ser Gly Lys Ser Thr Thr Val Glu
     50                  55                  60

Val Met Cys Thr Glu Gln Asn Ile Glu Ile Ile Glu Tyr Ser Pro Glu
 65                  70                  75                  80

Tyr Leu His Asn Glu Asp Phe Glu Cys Glu Lys Pro Asp Phe Thr Gln
                 85                  90                  95

Leu Arg Arg Phe Leu Leu Arg Arg His Gly Ser Leu Arg Gly Gly Gly
            100                 105                 110

Leu Lys Lys Arg Leu Leu Leu Val Thr Glu Leu Pro Asp Gln Ala Tyr
        115                 120                 125

Ser Asp Ala Glu Lys Phe Arg Glu Asp Leu Ser Glu Val Leu Gln His
    130                 135                 140

Ile Trp His Pro Val Ile Phe Cys Leu Thr Asn Ser Ile Ala Cys Trp
145                 150                 155                 160

Asn Leu Asn Pro Asp Arg Leu Phe Thr Lys Asp Phe Asn Ile Met Asn
                165                 170                 175

Gly Ile Asp Thr Val Thr Phe Asn Pro Val Ala Asp Ser Phe Met Lys
            180                 185                 190

Lys Ala Leu Val Arg Ala Ser Asn Cys Leu Ser Ser Pro Leu Ser Asp
        195                 200                 205

Ala Lys Leu Asn Val Ile Gly Glu Glu Ala Gly Gly Asp Leu Arg Ile
    210                 215                 220

Ala Met Asn Met Leu Gln Met Asn Ser Ile Gly Pro Asn Ala Asp Arg
225                 230                 235                 240

Arg Ser Gly Asn Ser Val Ile Cys Ala Ser Lys Ala Asn Arg Glu Glu
                245                 250                 255

Ala Phe His Met Ile Gly Arg Ile Leu Tyr Ala Lys Arg Val Asn Pro
            260                 265                 270

Asn Val Pro Lys Pro Ser Arg Phe Ser Lys Arg Arg Arg Lys Ser Ala
```

|  | 275 |  |  |  | 280 |  |  |  | 285 |  |  |
|---|---|---|---|---|---|---|---|---|---|---|---|

Pro Ile Pro Glu Pro Leu Val Arg Thr Glu Leu Glu His Asp Pro Thr
        290                         295                    300

Asp Ile Ile Thr Met Ser Ser Met Thr Ser Glu Lys Leu Leu Asp Phe
305                      310                   315                     320

Leu Phe Gln Asn Glu Pro Ile Phe Cys Ser Asn Ile Ser Lys Tyr Arg
                  325                    330                 335

Tyr Val Ala Glu Thr Phe Ser Met Cys Asp Phe Leu Thr Gly Asp Trp
            340                    345                    350

Thr Thr Arg Lys Ser Leu Pro Glu Asp Tyr Val Ala Gln Met Ala Thr
            355                    360                 365

Arg Ser Val Met Trp Asn Asn Tyr Lys Glu Pro Arg Pro Gly Thr Leu
370                      375                   380

Phe Ala Val Gly Arg Pro Leu Arg Ser Ser Leu Glu Lys His Thr Ala
385                      390                   395                     400

Arg Thr Lys Leu Glu Leu Gln Arg Leu Pro Met Ile Gly Ala Lys Asp
            405                    410                 415

Tyr Ala Ala Leu Thr Cys Pro Tyr Ile Thr Ile Lys Asp Ile Ile
            420                    425                    430

Asp Pro Gln Arg Ile Glu Tyr Phe Leu Ser Arg Pro Met Asp Ile Asn
            435                    440                 445

Trp Gln Trp Gly Asn Asp Lys Ile Glu Glu His Leu Glu Lys Gln Tyr
        450                    455                    460

Ala Leu Asp Tyr Lys Gly Arg Lys Lys His Arg Leu Pro Leu His Lys
465                      470                   475                    480

Ala Pro Lys Pro Ser Gly Lys Ile Ile Glu Val Val Asp Leu Glu Glu
                  485                    490                 495

Glu Glu Glu Lys Phe Thr Ile Glu Glu Ser Ser Asp Asp Ser Phe Glu
            500                    505                    510

Glu Phe

```
<210> SEQ ID NO 15
<211> LENGTH: 804
<212> TYPE: DNA
<213> ORGANISM: Caenorhabditis elegans

<400> SEQUENCE: 15
atgatggaat tagaaacggg tcaatgcaca attatggaat tgaaaaaaga aaatgtgaag      60
gagctcgcgc aggtcttcaa aaccgtcgct tttaaggata caggaacgtg gcacgcttcc     120
gaggcgggca tgaagatcac agtcgacgat ggatcctatc agctggccag cgttttatc     180 aatccggcgt tcttctcgag ttttaaagtt cgcgaggaga tagtttcgat gaaaatctcg     240
attaaatcga tttctgaatt cctgagcatt tcggaaaact cgtcgagttc tgtaaaagtc     300
tcgtatccgg gaatgtttca gcctgtgaaa atgcttgttg aagacgcaga cggatgggtg     360
gcacgtggca attttacaac aacgctggca gatcaagagc tcgactttga attcgatgac     420
gctggtgtgc tggcgaccta tctgcttaaa actcaagttc tcaaggagat tatcaaggac     480
ttcgatgaca caagccgaac ggtgagaatt caattcacca agaattcact gtgtttcacg     540
actttcggtg atgttggcga gactacagta tcaataccgt ctcgaagcct tcaaatggaa     600
agtgtaaagt gccttgaaga agttgaattt agctatcttc tgtcgcttat tcaacgaatg     660
actaccgcct ttatactggc tacaaagctc atcctccgtg tcgacgagcg tggcgtcctc     720
tcctgtcaat tttcaatcga tcacggcgag ggaaacgcaa gctacattga atttctgacg     780
```
gtgcccgctg atgaagaaga ataa                                                                                              804

<210> SEQ ID NO 16
<211> LENGTH: 267
<212> TYPE: PRT
<213> ORGANISM: Caenorhabditis elegans

<400> SEQUENCE: 16

Met Met Glu Leu Glu Thr Gly Gln Cys Thr Ile Met Glu Leu Lys Lys
1               5                   10                  15

Glu Asn Val Lys Glu Leu Ala Gln Val Phe Lys Thr Val Ala Phe Lys
            20                  25                  30

Asp Thr Gly Thr Trp His Ala Ser Glu Ala Gly Met Lys Ile Thr Val
        35                  40                  45

Asp Asp Gly Ser Tyr Gln Leu Ala Ser Val Phe Ile Asn Pro Ala Phe
    50                  55                  60

Phe Ser Ser Phe Lys Val Arg Glu Glu Ile Val Ser Met Lys Ile Ser
65                  70                  75                  80

Ile Lys Ser Ile Ser Glu Phe Leu Ser Ile Ser Glu Asn Ser Ser Ser
                85                  90                  95

Ser Val Lys Val Ser Tyr Pro Gly Met Phe Gln Pro Val Lys Met Leu
            100                 105                 110

Val Glu Asp Ala Asp Gly Trp Val Ala Arg Gly Asn Phe Thr Thr Thr
        115                 120                 125

Leu Ala Asp Gln Glu Leu Asp Phe Glu Phe Asp Asp Ala Gly Val Leu
    130                 135                 140

Ala Thr Tyr Leu Leu Lys Thr Gln Val Leu Lys Glu Ile Ile Lys Asp
145                 150                 155                 160

Phe Asp Asp Thr Ser Arg Thr Val Arg Ile Gln Phe Thr Lys Asn Ser
                165                 170                 175

Leu Cys Phe Thr Thr Phe Gly Asp Val Gly Glu Thr Thr Val Ser Ile
            180                 185                 190

Pro Ser Arg Ser Leu Gln Met Glu Ser Val Lys Cys Leu Glu Glu Val
        195                 200                 205

Glu Phe Ser Tyr Leu Leu Ser Leu Ile Gln Arg Met Thr Thr Ala Phe
    210                 215                 220

Ile Leu Ala Thr Lys Leu Ile Leu Arg Val Asp Glu Arg Gly Val Leu
225                 230                 235                 240

Ser Cys Gln Phe Ser Ile Asp His Gly Glu Gly Asn Ala Ser Tyr Ile
                245                 250                 255

Glu Phe Leu Thr Val Pro Ala Asp Glu Glu Glu
            260                 265

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: DNA primer

<400> SEQUENCE: 17
gcgggatccc tatgtcccat cactctcgta gtcttc                                                                                 36

<210> SEQ ID NO 18
<211> LENGTH: 39
<212> TYPE: DNA
<213> ORGANISM: Artificial Sequence

```
<220> FEATURE:
<223> OTHER INFORMATION: Description of Artificial Sequence:  DNA primer

<400> SEQUENCE: 18
agggaattcc atatgcccct tctgacccaa cagatccaa                              39

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence:  DNA primer

<400> SEQUENCE: 19
gcgggatcct caagactcag attcaggaac ttcttc                                 36

<210> SEQ ID NO 20
<211> LENGTH: 606
<212> TYPE: PRT
<213> ORGANISM: Schizosaccharomyces pombe

<400> SEQUENCE: 20
```

Met Arg Arg Gln Leu Ser Phe His Glu Ser Thr Lys Arg Ser Leu Lys
 1               5                  10                  15

Lys Lys Lys Ile Arg Lys Ile Glu Lys Pro Ser Leu Val Ser Lys Thr
            20                  25                  30

Ser Arg Asp Lys Asn Ala Ser Ile Thr Asp Ile His Glu Glu Asp Ile
        35                  40                  45

Glu Ala Phe Ser Asp Glu Glu Asn Lys Ile Val His Leu Asn Asn Leu
    50                  55                  60

Lys Glu Asp Arg Phe Gln Leu Trp Phe Glu Lys Tyr Ile Pro Gln Lys
65                  70                  75                  80

Ala Ala Asp Leu Ala Val His Lys Ser Lys Ile Ser Ala Ile Lys Gln
                85                  90                  95

Trp Met Leu Thr Asp Ser Leu Glu Ser Arg Leu Leu Leu Ile Cys Gly
            100                 105                 110

Pro Ser Gly Cys Gly Lys Ser Thr Ala Val Gln Val Leu Ala Lys Glu
        115                 120                 125

Leu Gly Tyr Ser Leu Ile Glu Trp Leu Asn Pro Met Asn Leu Lys Glu
    130                 135                 140

Pro Ser Asn Gln Glu Ser Asp Thr Leu Ser Leu Thr Glu Lys Phe Ser
145                 150                 155                 160

Arg Phe Met Ser Leu Cys Glu Thr Tyr Pro Glu Leu Glu Leu Met Asp
                165                 170                 175

Ser Asn Asn Ile Gln Lys Arg Gly Lys Asn Ala Gln Gly Lys Lys Lys
            180                 185                 190

Phe Ile Phe Leu Asp Glu Ile Pro His Leu Ser Lys Phe Asn Gly Ser
        195                 200                 205

Leu Asp Ala Phe Arg Asn Val Ile Arg Thr Ala Leu Thr Ser Arg Gly
    210                 215                 220

Ala Phe Ser Ile Ile Met Val Leu Thr Glu Ile Gln Leu Asn Asn Leu
225                 230                 235                 240

Glu Gly Ile Asn Ser Gln Asp Arg Asn Ser Phe Asn Ser Val Gln Ile
                245                 250                 255

Met Gly Asn Asp Leu Leu Gln Asp Pro Arg Val Thr Val Leu Gln Phe
            260                 265                 270

Asn Pro Ile Ala Pro Thr Tyr Met Lys Lys Cys Leu Gly Ser Ile Leu

-continued

```
                    275                 280                 285
Arg Lys Glu Gly Val Pro Lys Ser Pro Lys Leu Leu Ser Leu Val Glu
            290                 295                 300
Asn Ile Cys Ser Ala Ser Glu Gly Asp Leu Arg Ser Ala Ile Asn Ser
305                 310                 315                 320
Leu Gln Leu Ser Ile Ser Gln Ser Phe Glu Lys Lys Gly Thr Lys Asn
                325                 330                 335
Ile Arg Glu Val Lys Glu Gly Lys Gly Lys Gly Asn Asp Phe Ser Leu
            340                 345                 350
Glu Ala Ala Gln Val Leu Glu Arg Leu Ser Lys Ser Asp Ser Glu Ala
                355                 360                 365
Tyr Ala Arg Phe Lys Asn Tyr Lys Ser Ala Tyr Ile Pro Lys Ser Asp
            370                 375                 380
Lys Asn Glu Asn Ser Phe Phe Lys Lys Asp Val Gly Leu Gly Met Met
385                 390                 395                 400
His Ala Ile Gly Lys Val Val Trp Asn Lys Arg Glu Gly Asp Asp Glu
                405                 410                 415
Val Leu Lys Ala Ser Ser Gln Gln Thr Gly Asn Ser Glu Arg Ile Lys
            420                 425                 430
Gly Val Lys Val Ser Lys Ser Gln Glu Asn Lys Asn Cys Ile Ser Leu
                435                 440                 445
Lys Ser Asp Gln Arg Glu Arg Met Leu Asn Val Asp Gln Cys Phe Thr
            450                 455                 460
Ser Lys Arg Arg Ser Leu Val Asp Ile Glu Ser Thr Ile Asn Gln Ser
465                 470                 475                 480
Gly Leu Ser Gly Ser Val Phe Arg Tyr Gly Leu Phe Glu Asn Tyr Val
                485                 490                 495
Asp Ser Cys Val Thr Thr Asp Glu Ala Phe Asn Val Cys Asp Leu Leu
            500                 505                 510
Ser Ile Ser Asp Cys Leu Ser His Asp Phe Pro Tyr Ser Tyr Thr Gly
                515                 520                 525
Asp Glu Ile Ser Thr Trp Phe Ser Val Gln Gly Thr Leu Phe Tyr Leu
            530                 535                 540
Pro Ser Pro Val Pro Arg Lys Trp Arg Gln Leu Arg Phe Gln Gln Trp
545                 550                 555                 560
Asn Asn Glu Gly Ile Val Arg Gly Ile Phe Asp Asp Tyr Met Val Ile
                565                 570                 575
Tyr Gly Lys Arg Ser Val Ser Asp Pro Val Ile Glu Ala His Glu Asp
            580                 585                 590
Gln Val Leu Glu Asp Ile Asp Asp Pro Ile Glu Asp Glu Asp
                595                 600                 605

<210> SEQ ID NO 21
<211> LENGTH: 659
<212> TYPE: PRT
<213> ORGANISM: Saccharomyces cerevisiae

<400> SEQUENCE: 21

Met Asp Ser Thr Asn Leu Asn Lys Arg Pro Leu Leu Gln Tyr Ser Leu
1               5                   10                  15
Ser Ser Leu Gly Ser Gln Ile Thr Lys Trp Ser Ser Ser Arg Pro Thr
                20                  25                  30
Ser Pro Val Arg Lys Ala Arg Ser Thr Glu Asn Asp Phe Leu Ser Lys
            35                  40                  45
```

-continued

```
Gln Asp Thr Ser Ser Ile Leu Pro Ser Ile Asn Asp Gly Gly Glu
     50                  55                  60

Gln Trp Tyr Glu Lys Phe Lys Pro Asn Cys Leu Glu Gln Val Ala Ile
 65                  70                  75                  80

His Lys Arg Lys Leu Lys Asp Val Gln Glu Ala Leu Asp Ala Met Phe
                 85                  90                  95

Leu Pro Asn Ala Lys His Arg Ile Leu Leu Ser Gly Pro Ser Gly
                100                 105                 110

Cys Ser Lys Ser Thr Val Ile Lys Glu Leu Ser Lys Ile Leu Val Pro
             115                 120                 125

Lys Tyr Arg Gln Asn Ser Asn Gly Thr Ser Phe Arg Ser Thr Pro Asn
    130                 135                 140

Glu His Lys Val Thr Glu Phe Arg Gly Asp Cys Ile Val Asn Asp Leu
145                 150                 155                 160

Pro Gln Met Glu Ser Phe Ser Glu Phe Leu Lys Gly Ala Arg Tyr Leu
                165                 170                 175

Val Met Ser Asn Leu Ser Leu Ile Leu Ile Glu Asp Leu Pro Asn Val
            180                 185                 190

Phe His Ile Asp Thr Arg Arg Phe Gln Gln Leu Ile Leu Gln Trp
    195                 200                 205

Leu Tyr Ser Ser Glu Pro Leu Leu Pro Leu Val Ile Cys Ile Thr
    210                 215                 220

Glu Cys Glu Ile Pro Glu Asn Asp Asn Asn Tyr Arg Lys Phe Gly Ile
225                 230                 235                 240

Asp Tyr Thr Phe Ser Ala Glu Thr Ile Met Asn Lys Glu Ile Leu Met
            245                 250                 255

His Pro Arg Leu Lys Arg Ile Lys Phe Asn Pro Ile Asn Ser Thr Leu
            260                 265                 270

Leu Lys Lys His Leu Lys Phe Ile Cys Val Gln Asn Met Lys Met Leu
            275                 280                 285

Lys Glu Lys Asn Lys Trp Asn Lys Arg Gln Glu Val Ile Asp Tyr Ile
    290                 295                 300

Ala Gln Glu Thr Gly Asp Ile Arg Ser Ala Ile Thr Thr Leu Gln Phe
305                 310                 315                 320

Trp Ala Thr Ser Ser Gly Ser Leu Pro Ile Ser Thr Arg Glu Ser Thr
                325                 330                 335

Ile Ser Tyr Phe His Ala Ile Gly Lys Val Ile His Gly Ser His Ser
            340                 345                 350

Thr Asn Asn Asp Asn Glu Met Ile Asn Asn Leu Phe Glu Asn Ser Asn
    355                 360                 365

Asn Leu Leu Ser Lys Glu Asp Phe Lys Leu Gly Ile Leu Glu Asn Tyr
    370                 375                 380

Asn Thr Phe Asn Lys Gly Glu Phe Ser Ile Ser Asp Ala Ser Ser Ile
385                 390                 395                 400

Val Asp Cys Leu Ser Glu Cys Asp Asn Met Asn Gly Leu Pro Glu Ser
                405                 410                 415

Asn Glu Tyr Gly Leu Arg Glu Val Arg Lys Thr Phe Arg Asn Ile Ser
            420                 425                 430

Lys Gln Gly His Asn His Gly Thr Val Tyr Phe Pro Arg Glu Trp Lys
            435                 440                 445

Val Arg Lys Leu Gln Asn Ser Phe Lys Val Gln Ala Glu Asp Trp Leu
    450                 455                 460

Asn Val Ser Leu Tyr Lys Tyr Asn Ala Val His Ser Phe Arg Asn Ile
```

-continued

```
             465                 470                 475                 480
Thr Leu Glu Phe Gly Tyr Tyr Ala Pro Leu Ile Arg Lys Cys Gln Ser
                    485                 490                 495
Tyr Lys Lys Tyr Ile Leu Tyr Tyr Leu Lys Asn Leu Pro Ser Gly
            500                 505                 510
Ser Ser Gly Pro Lys Gln Thr Met Asp Lys Phe Ser Asp Ile Met Lys
            515                 520                 525
Val Glu Asn Gly Ile Asp Val Asp Arg Ile Gly Gly Pro Ile Glu
    530                 535                 540
Ala Leu Ser Val Glu Asp Gly Leu Ala Pro Leu Met Asp Asn Asp Ser
545                 550                 555                 560
Asn Asn Cys Asp His Leu Glu Asp Gln Lys Lys Glu Arg Asp Arg Arg
                565                 570                 575
Leu Arg Met Leu Ile Asp Gln Tyr Glu Arg Asn Val Met Met Ala Asn
                580                 585                 590
Asp Asp Leu Glu Asp Glu Glu Thr Ser Phe Asn Asp Asp Pro Ile Val
            595                 600                 605
Asp Ser Asp Ser Asp Asn Ser Asn Asn Ile Gly Asn Glu Thr Phe Gly
    610                 615                 620
Arg Ser Asp Glu Asp Glu Ser Leu Cys Glu Ile Leu Ser Gln Arg Gln
625                 630                 635                 640
Pro Arg Lys Ala Pro Val Ile Ser Glu Ser Leu Ser Asp Ser Asp Leu
                645                 650                 655
Glu Ile Leu

<210> SEQ ID NO 22
<211> LENGTH: 323
<212> TYPE: PRT
<213> ORGANISM: Schizosaccharomyces pombe

<400> SEQUENCE: 22

Met Phe Gln Ala Glu Thr Val Cys Leu Lys Gln Ile Gln Ser Thr Leu
 1               5                  10                  15
Arg Cys Ile Asp Phe Ser Lys Glu Cys Thr Ile Glu Ile Thr Ser Arg
                20                  25                  30
Gly Leu Arg Phe Ala Val Glu Glu Ser Gln Ser Leu Gln Ala His Ala
            35                  40                  45
Phe Leu Asp Lys Ser Leu Phe Gln Thr Phe Asn Phe Gln Gly Asp Ser
        50                  55                  60
Asp Gly Asp Thr Tyr Met Phe Gln Thr Met Ile Ser Pro Leu Leu Gln
 65                  70                  75                  80
Ser Leu Ser Ile Tyr Thr Asp Gly Lys Glu Arg Ile Ser Thr Ser Ala
                85                  90                  95
Trp Asp Gln Pro Thr Val Asn Ile Met His Lys Arg Gly Val Ile Cys
                100                 105                 110
Lys Val Gln Tyr Asn Gly Pro Gly Cys Pro Phe Ile Trp Glu Val Glu
            115                 120                 125
Glu Met Ala Gly Tyr Ala Thr Ala Cys Glu Leu Leu Thr Met Glu Cys
        130                 135                 140
Glu Asp Asp Val Asp Ile Asn Arg Leu Ala Ser Thr Leu Cys Thr Lys
145                 150                 155                 160
Ile Ile Met Lys Ser Asn Trp Leu Tyr Asp Ala Leu Val Glu Leu Asp
                165                 170                 175
Asn Asn Met Gly Glu Asn Leu Ile Ile His Thr Ser Ser Gln Lys Ser
```

```
Thr Phe Leu Leu Arg Cys Val Gly Ala Leu Ser Thr Thr Glu Ile Glu
            195                 200                 205

Tyr Pro Asn Glu Lys Ser Val Leu Glu Ser Phe Glu Thr Asp Ser Glu
210                 215                 220

Asn Thr Tyr Ser Tyr Arg Phe Ser Leu Ile Arg His Ala Leu Lys Ala
225                 230                 235                 240

Leu Gln Val Gly Ser Lys Val Asn Leu Arg Ile Asp Glu Asn Gly Thr
            245                 250                 255

Leu Ser Ile Gln Ile Met Leu Val Gly Gln Gly Leu Cys Thr Phe
            260                 265                 270

Val Asp Phe Cys Ile Val Pro Leu Asp Leu Val Ser Glu Asp Glu Glu
            275                 280                 285

Glu Asp Glu Glu Glu Pro Ala Glu Ser Asn Gln Ser Asp Asn Asn
290                 295                 300

Val Leu Arg Asn Asp Pro Asn Tyr Arg Gly Asp Ala Glu Thr Glu Asp
305                 310                 315                 320

Glu Asp Ser
```

<210> SEQ ID NO 23
<211> LENGTH: 353
<212> TYPE: PRT
<213> ORGANISM: Ustilago maydis

<400> SEQUENCE: 23

```
Met Pro Ala Glu Gly Ala Cys Asp Ala Ala Ser Leu Met Thr Leu Thr
1               5                   10                  15

Ala Thr Leu Ser Asp Val Thr Gly Leu Ala Asn Leu Leu Lys Ser Val
            20                  25                  30

Ala Ile Gln Thr His Ala Val Val Ile Ala Ser Ser Gly Leu Glu
        35                  40                  45

Ile Ile Thr Glu Leu Asn Arg Thr Leu Gln Ala His Ala Tyr Leu Tyr
    50                  55                  60

Ser His Met Phe Asp Ser Tyr Arg Phe Glu Asn Ala Gln Asp His
65                  70                  75                  80

Asp Glu Pro Asp Ser Val Ser Phe Glu Val Asn Leu Gln Thr Trp Ile
                85                  90                  95

Ser Cys Leu Asn Ile Phe Gly Gly Val Gly Pro Ser Arg Pro His Ser
            100                 105                 110

Ser Ser Ser Gly Leu Pro Gly Phe Arg Pro Glu Gln Gly Thr Arg Met
        115                 120                 125

Lys Leu Ser Tyr Gln Gly His Gly Asn Pro Leu Val Leu Glu Leu Glu
130                 135                 140

Gln Asp Ala Asn Val Leu Thr Arg Val Ser Met Ser Thr Tyr Glu Pro
145                 150                 155                 160

Ser Phe Leu Thr Asp Met Val Phe Glu Pro Gln Asn Met Val Ala Gln
                165                 170                 175

Val Ile Val Ala Ser Glu Leu Met Gln Ser Ala Phe Thr Glu Ile Asp
            180                 185                 190

Ala Ser Cys Lys Lys Leu Ser Ile Leu Ile Thr Ser Pro His Ser Leu
        195                 200                 205

Ser Thr Tyr Asp Gly Asp Gln Arg Thr Glu Ala Pro Ala Pro Thr Lys
    210                 215                 220

Arg Asn Thr Ser Ala Ser Met Leu Lys Phe Arg Ala Ile Ser Asp Thr
```

```
225                 230                 235                 240

Gly Ser Ser Glu Met Glu Phe Pro Ala Ser Leu Thr Ser Ser Asp Pro
                245                 250                 255

Thr Gly Val Ile Glu Lys Phe Val Ala Leu Pro Gly Ser Ser Glu Gln
                260                 265                 270

Trp Tyr Asp Phe Thr Leu Leu Ser Arg Thr Met Ser Val Leu Arg Ser
                275                 280                 285

Ser Ile Lys Thr Ser Leu Arg Met Asp Glu Ala Gly Leu Ile Ser Phe
    290                 295                 300

Gln Phe Met Met Pro Lys Tyr Arg Arg Ala Ala Ala Gly Ala Pro
305                 310                 315                 320

Leu Thr Asn Ala Ala Ala Gly Gln Ala Ala His Glu Asp Glu Gln Asp
                325                 330                 335

Ala Phe Cys Glu Phe Leu Cys Cys Pro Leu Asp Thr Ser Thr Leu Ile
                340                 345                 350

Val

<210> SEQ ID NO 24
<211> LENGTH: 318
<212> TYPE: PRT
<213> ORGANISM: Saccharomyces cerevisiae

<400> SEQUENCE: 24

Met Arg Ile Asn Ser Glu Leu Ala Asn Lys Phe Ser Ala Ser Thr Val
  1               5                  10                  15

His Leu Glu His Ile Thr Thr Ala Leu Ser Cys Leu Thr Pro Phe Gly
                 20                  25                  30

Ser Lys Asp Asp Val Leu Ile Phe Ile Asp Ala Asp Gly Leu Ser Phe
             35                  40                  45

Val Arg Glu Asn His Val Ile Lys Ile Gln Leu Leu Ser Arg
         50                  55                  60

Glu Leu Phe Met Ser Tyr Ser Tyr Arg Asn Glu Thr Glu Asp His Met
 65                  70                  75                  80

Lys Leu Cys Val Lys Ile Asn His Ile Leu Asp Ser Val Ser Val Met
                 85                  90                  95

Asn Arg Asn Ser Asp Asp Ile Val Glu Cys Thr Leu Ser Tyr Asp Gly
                100                 105                 110

His Gly Ser Pro Phe Val Leu Ile Phe Glu Asp Ser Phe Ile Ser Glu
            115                 120                 125

Arg Val Glu Tyr Ser Thr Tyr Leu Ile Lys Asp Phe Asp Thr Asn Gly
        130                 135                 140

Leu Glu Leu Asp Arg Glu Arg Ile Ser Phe Glu Ala Ile Ile Lys Gly
145                 150                 155                 160

Glu Ala Leu His Ser Ala Leu Lys Asp Leu Lys Glu Ile Gly Cys Lys
                165                 170                 175

Glu Cys Tyr Val Tyr Ala Lys Thr Glu Ala Asn Asp Glu Asn Val Phe
            180                 185                 190

Ala Leu Ile Ser Lys Ser Gln Leu Gly Phe Ser Lys Ile Lys Leu Pro
        195                 200                 205

Ser Asn Arg Ser Ile Leu Glu Lys Leu Gln Val Phe Asp Gly Asp Ser
    210                 215                 220

Thr Thr Val Ile Asp Gly Phe Ala Val Ile Gly Phe Asp Phe Thr
225                 230                 235                 240

Ser Phe Asp Lys Ile Arg Lys Ser Thr Lys Ile Ala Ser Lys Val Leu
```

-continued

```
                       245                 250                 255
Phe Arg Met Asp Val His Gly Val Leu Ser Val Asn Ile Leu Ser Gln
                260                 265                 270

Thr Asp Val Ile Ile Thr Asp Thr Thr Arg Pro Ser Asn Asn Arg
            275                 280                 285

Pro Gly Ser Ile Arg Gln Leu Gln Leu Pro Lys Asp Tyr Pro Gly Ile
        290                 295                 300

Val Ile Glu Val Cys Met Leu Glu Lys Glu Ser Ile Asp Glu
305                 310                 315

<210> SEQ ID NO 25
<211> LENGTH: 287
<212> TYPE: PRT
<213> ORGANISM: Schizosaccharomyces pombe

<400> SEQUENCE: 25

Met Arg Phe Lys Thr Arg Ile Ser Asn Leu Tyr Thr Leu Thr Arg Leu
 1               5                  10                  15

Val Gln Ala Leu Asp Lys Ile Gly Arg Phe Cys Trp Leu Arg Leu Met
             20                  25                  30

Pro Glu Thr Val Asn Phe Val Ile Val Pro Asp Phe Arg Met Thr Gln
         35                  40                  45

Val Trp Ser Val Leu Glu Val Glu Thr Ile Phe Glu Asp Tyr Val Val
     50                  55                  60

Gln Ser Asn Ala Asp Asn Val Ile Asn Leu Glu Val Pro Ile Asp Asn
 65                  70                  75                  80

Phe Tyr Lys Ala Leu Arg Ser Ala Ala Asn Ala Ser Asp Ser Thr Val
                 85                  90                  95

Arg Leu Ser Lys Lys Asn Asn Gln Pro Leu Leu Ser Leu Ser Thr Thr
            100                 105                 110

Trp Ser Gly Arg Ala Phe Gly Ser Asn Ile Val Thr His Asn Ile Pro
        115                 120                 125

Val Arg Val Leu Ser Gln Ser Tyr Val Ser Val Ile Lys Glu Pro Thr
    130                 135                 140

Ala Pro Glu Pro Asp Cys His Ile Phe Leu Pro Gln Leu Asn Phe Leu
145                 150                 155                 160

Arg His Val Val Asp Lys Tyr Lys Ser Leu Ser Asp Arg Ile Ile Met
                165                 170                 175

Ser Ala Asn Met Ser Gly Glu Leu Gln Leu Ser Val Asn Ile Pro Ser
            180                 185                 190

Ala Arg Val Ser Thr Lys Trp Lys Gly Leu Glu Asn Pro Glu Leu Asp
        195                 200                 205

Pro Ser Gln Val Glu Asp Ile Ser Arg His Pro Ser Gln Thr Arg Ala
    210                 215                 220

Pro Glu Glu Phe Val His Met Arg Leu Asp Ser Lys Asp Leu Val Asn
225                 230                 235                 240

Met Leu Lys Ile Ser Ser Val Ala Lys Arg Val Ile Ala Cys Phe Cys
                245                 250                 255

Glu Gly His Ala Leu Val Leu Tyr Val Tyr Ile Thr Asp Pro Glu Asp
            260                 265                 270

Glu His Thr Ala Val Leu Thr Tyr Tyr Ile Ser Thr Tyr Val Asp
        275                 280                 285

<210> SEQ ID NO 26
<211> LENGTH: 124
```

```
<212> TYPE: DNA
<213> ORGANISM: Artificial Sequence
<220> FEATURE:
<223> OTHER INFORMATION: Description of Artificial Sequence:  artificial
      vector

<400> SEQUENCE: 26
tctagaaata attttgttta actttaagaa ggagatatac catgggcctt cgaagggctt        60
ctgttcatca tcatcatcat catagcagcg gccatatcga aggtcgtcat atgctcgagg       120
atcc                                                                    124

<210> SEQ ID NO 27
<211> LENGTH: 24
<212> TYPE: PRT
<213> ORGANISM: Artificial Sequence
<220> FEATURE:
<223> OTHER INFORMATION: Description of Artificial Sequence:  leader

<400> SEQUENCE: 27

Met Gly Leu Arg Arg Ala Ser Val His His His His His His Ser Ser
 1               5                  10                  15

Gly His Ile Gly Gly Arg His Met
                20
```